(12) United States Patent
He et al.

(10) Patent No.: US 9,125,814 B2
(45) Date of Patent: Sep. 8, 2015

(54) BIOCOMPATIBLE CROSSLINKED HYDROGELS, DRUG-LOADED HYDROGELS AND METHODS OF USING THE SAME

(75) Inventors: Yuehua He, Surrey (CA); Aniko Takacs-Cox, North Vancouver (CA); Anthony Boey, Coquitlam (CA); Brent Zaluski, Vancouver (CA); Roger A. Smith, North Vancouver (CA); Audrey A. Deschamps, Vancouver (CA); Rui Avelar, Vancouver (CA)

(73) Assignee: Angiotech Pharmaceuticals, Inc. (CA)

( * ) Notice: Subject to any disclaimer, the term of this patent is extended or adjusted under 35 U.S.C. 154(b) by 1289 days.

(21) Appl. No.: 12/428,411

(22) Filed: Apr. 22, 2009

(65) Prior Publication Data

US 2009/0324720 A1 Dec. 31, 2009

Related U.S. Application Data

(60) Provisional application No. 61/046,920, filed on Apr. 22, 2008, provisional application No. 61/046,954, filed on Apr. 22, 2008, provisional application No. 61/046,965, filed on Apr. 22, 2008.

(51) Int. Cl.

| | |
|---|---|
| *A61K 9/10* | (2006.01) |
| *A61K 38/20* | (2006.01) |
| *A61K 38/48* | (2006.01) |
| *A61K 38/16* | (2006.01) |
| *A61K 31/445* | (2006.01) |
| *A61K 31/4025* | (2006.01) |
| *A61K 31/10* | (2006.01) |
| *A61K 31/08* | (2006.01) |
| *C07D 403/14* | (2006.01) |
| *C07C 317/00* | (2006.01) |
| *C07C 43/04* | (2006.01) |
| *A61K 9/06* | (2006.01) |
| *A61K 9/00* | (2006.01) |
| *A61K 47/34* | (2006.01) |
| *A61L 24/00* | (2006.01) |
| *A61L 26/00* | (2006.01) |
| *A61L 31/14* | (2006.01) |
| *A61L 31/16* | (2006.01) |
| *C08G 65/331* | (2006.01) |
| *C08G 65/332* | (2006.01) |
| *C08G 65/333* | (2006.01) |
| *C08G 65/334* | (2006.01) |
| *C08G 65/337* | (2006.01) |

(52) U.S. Cl.
CPC ................. *A61K 9/06* (2013.01); *A61K 9/0024* (2013.01); *A61K 47/34* (2013.01); *A61L 24/0015* (2013.01); *A61L 24/0031* (2013.01); *A61L 24/0042* (2013.01); *A61L 26/008* (2013.01); *A61L 26/009* (2013.01); *A61L 26/0066* (2013.01); *A61L 31/145* (2013.01); *A61L 31/148* (2013.01); *A61L 31/16* (2013.01); *C08G 65/337* (2013.01); *C08G 65/3312* (2013.01); *C08G 65/3324* (2013.01); *C08G 65/3342* (2013.01); *C08G 65/33317* (2013.01); *C08G 65/33337* (2013.01); *C08G 65/33368* (2013.01); *A61L 2300/00* (2013.01); *C08L 2203/02* (2013.01)

(58) Field of Classification Search
CPC A61K 47/34; A61L 24/0015; A61L 24/0031; A61L 24/0042; A61L 26/0066; A61L 26/008; A61L 26/009; A61L 31/145; A61L 31/148; A61L 31/16; C08L 2203/02
See application file for complete search history.

(56) References Cited

U.S. PATENT DOCUMENTS

| | | | |
|---|---|---|---|
| 5,874,500 A | 2/1999 | Rhee et al. | 525/54.1 |
| 6,051,648 A | 4/2000 | Rhee et al. | 525/54.1 |
| 6,458,889 B1 | 10/2002 | Trollsas et al. | 525/54.1 |
| 6,495,127 B1 | 12/2002 | Wallace et al. | 424/78.03 |
| 6,632,457 B1 * | 10/2003 | Sawhney | 424/501 |
| 6,833,408 B2 | 12/2004 | Sehl et al. | 525/54.1 |
| 7,883,693 B2 | 2/2011 | Sehl et al. | 424/78.03 |
| 2004/0219214 A1 * | 11/2004 | Gravett et al. | 424/484 |
| 2004/0220087 A1 * | 11/2004 | Bar-Or | 514/7 |

FOREIGN PATENT DOCUMENTS

| | | |
|---|---|---|
| WO | WO 97/22371 A1 | 6/1997 |
| WO | WO 00/62827 A2 | 10/2000 |
| WO | WO 02/102864 A1 | 12/2002 |
| WO | WO 2004/028547 A1 | 4/2004 |

OTHER PUBLICATIONS

Greenwald et al. "An unexpected amide bond cleavage: poly (ethylene glycol) transport forms of vancomycin. 2" European Journal of Medicinal Chemistry 2005, 40, 798-804.*

* cited by examiner

*Primary Examiner* — Kortney L Klinkel

(57) ABSTRACT

Disclosed are hydrogel compositions formed by the mixture of a tetramethylmethane substituted with one or more polyethylene glycols, and wherein each polyethylene glycol substituent is independently further substituted with one or more electrophilic groups, and a tetramethylmethane substituted with one or more polyethylene glycols, and wherein each polyethylene glycol substituent is independently further substituted with one or more nucleophilic groups. Disclosed are also methods of preparing the above hydrogels. The hydrogel compositions can further comprise pharmaceuticals, such as analgesics or local anesthetics. Disclosed are also methods of sealing a wound, preventing post-surgical adhesion, and reducing post-surgical pain using the disclosed hydrogels.

5 Claims, 5 Drawing Sheets

BIOCOMPATIBLE CROSSLINKED HYDROGELS, DRUG-LOADED HYDROGELS AND METHODS OF USING THE SAME

CROSS-REFERENCE TO RELATED APPLICATIONS

This application claims the benefit under 35 U.S.C. §119(e) of U.S. Provisional Patent Application Nos. 61/046,920, 61/046,954 and 61/046,965, all filed Apr. 22, 2008, which applications are herein incorporated by reference in their entireties.

FIELD OF THE DISCLOSURE

This disclosure relates generally to biocompatible polymer compositions that rapidly crosslink to form a gel, and methods of using the same, including a variety of tissue-related applications in which rapid adhesion to the tissue and gel formation is desired, as well as local delivery of pharmaceutical drugs, such as analgesics, to a site of surgery.

BACKGROUND

The use of polymer compositions in surgical procedures is now widely recognized, particularly those compositions manufactured with synthetic polymers. In contrast to many naturally derived compositions, synthetic polymer compositions can be formulated to exhibit predetermined physical characteristics, such as gel strength, as well as biological characteristics, such as biodegradability.

Several two-part co-polymer systems have been described that can be administered as liquids, or solutions, but which subsequently form gels at the site of administration. See, for example, U.S. Pat. Nos. 5,874,500 (Rhee et al., issued Feb. 23, 1999), 6,051,648 (Rhee et al., issued Apr. 18, 2000), 6,312,725 (Wallace et al., issued Nov. 6, 2001), 6,458,889 (Trollsas et al., issued Oct. 1, 2002), 6,495,127 (Wallace et al., issued Dec. 17, 2002), 6,624,245 (Wallace et al., issued Sep. 23, 2003), 7,176,256 (Rhee et al., issued Feb. 13, 2007), and U.S. Patent Application Publication No. 2005/0281883 A1 (Daniloff et al.), all of which are hereby incorporated by reference herein in their entirety, including any drawings. Such in situ gel-forming compositions are convenient to use since they can be administered as liquids from a variety of different devices, and are adaptable for administration to any site, since they are not preformed.

BRIEF SUMMARY

Disclosed herein are compositions comprising a compound of Formula I or Formula III, as described herein:

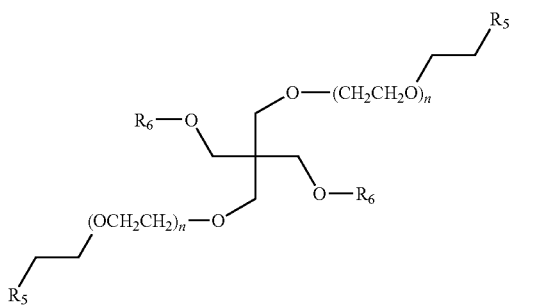

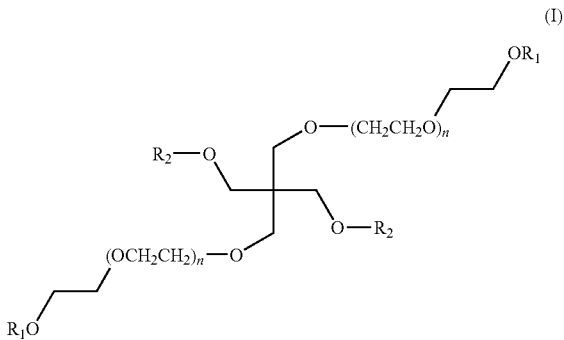

Also disclosed are methods of preparing a biodegradable crosslinked composition comprising: mixing a first compound and a second compound to obtain a first mixture, adding a first aqueous solution to the first mixture to obtain a first solution, adding a second aqueous solution to the first solution, wherein the first compound is a compound of Formula I, as described herein, and the second compound is a compound of Formula III, as described herein. Disclosed herein are also hydrogel compositions produced by the above method. Also disclosed are methods of sealing a wound by adding the above-described hydrogels to the wound. In addition, disclosed are methods of preventing post-surgical adhesion by administering the above-described hydrogels to a tissue.

Further disclosed are compositions comprising a biocompatible hydrogel and an analgesic, where the biocompatible hydrogel is produced by a method comprising: mixing a first compound and a second compound to obtain a first mixture, adding a first aqueous solution to the first mixture to obtain a first solution, adding a second aqueous solution to the first solution, where the first compound is a compound of Formula I:

(I)

and the second compound is a compound of Formula III:

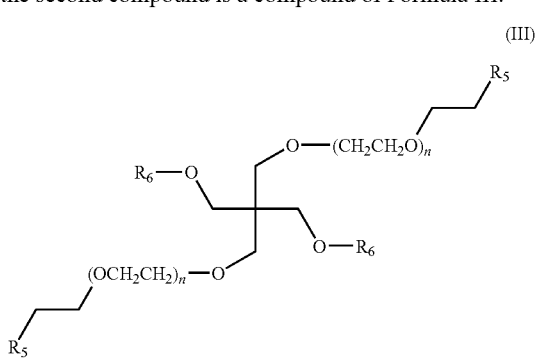

Further disclosed herein are compositions comprising a biocompatible hydrogel and an analgesic, wherein the biocompatible hydrogel is produced by a method comprising
mixing a first compound and a second compound to obtain a first mixture,
adding a first aqueous solution to the first mixture to obtain a first solution,
adding a second aqueous solution to the first solution, wherein
the first compound is a sulfhydryl reactive group-containing compound having the formula Compound$_1$-Y$_n$, wherein Y is a sulfhydryl reactive group and wherein n≥2;
the second compound is a sulfhydryl group-containing compound having the formula Compound$_2$-(SH)$_m$, wherein m≥2; and
wherein at least one of the first or second compounds is a polyalkylene oxide and
wherein the sulfhydryl groups and the sulfhydryl reactive groups react with one another to form covalent bonds therebetween when said components are mixed together to form a gel. In some embodiments, the gel forms in less than one minute.

Also disclosed are methods of reducing post-surgical pain comprising administering to a tissue at a site of surgery (e.g., an inguinal hernia repair or breast augmentation site) the above biocompatible hydrogels, where the biocompatible hydrogel contains an analgesic (e.g., bupivacaine).

DETAILED DESCRIPTION

Figure 1:
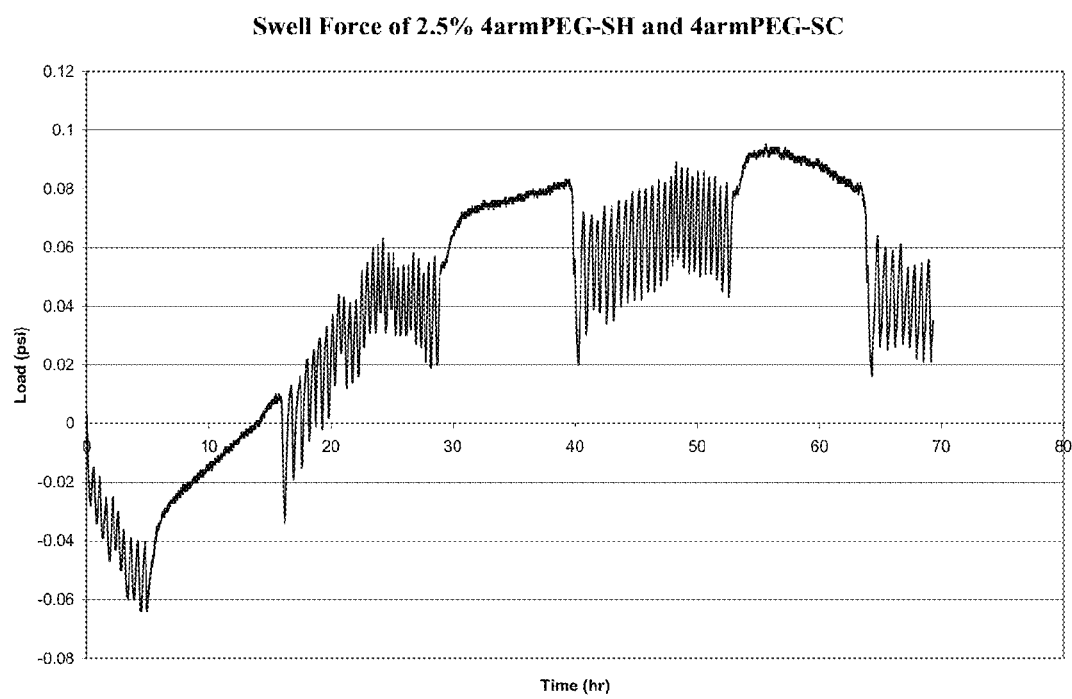
FIG. 1 is a graph showing the results of the swell force conducted on a gel having 2.5% 4-armPEG-SC and 2.5% 4-armPEG-SH.

Disclosed herein are two-component systems that form a biocompatible and biodegradable hydrogel once the two components are mixed together. The system may further comprise one or more drugs, including, e.g., analgesics.

1. Two-Component Hydrogel Systems

Typically, "hydrogel" refers to a network of polymer chains that are water-insoluble. Hydrogels are sometimes found as colloidal gels in which water is the dispersion medium. Hydrogels are superabsorbent (they can contain over 99% water) natural or synthetic polymers. Hydrogels also possess a degree of flexibility very similar to natural tissue, due to their significant water content.

The two-component hydrogel systems are described in detail in, for example, U.S. Pat. Nos. 5,874,500, 6,051,648, 6,312,725, 6,458,889, 6,495,127, 6,624,245, 7,176,256, and U.S. 2005/0281883, which references are incorporated herein by reference in their entireties.

In certain embodiments, each component of the system comprises a tetramethylmethane core, to each of which methyl groups a polyethylene glycol (PEG) arm is connected. The length of the PEG arms can be varied independently to produce components, and therefore hydrogels, of varying molecular weight.

One or more of the PEG arms of one component terminate in an electrophilic group, while one or more of the PEG arms of the second component terminate in a nucleophilic group. When the two components are mixed together at a basic (e.g., alkaline) pH, the electrophilic group of the first component reacts with the nucleophilic group of the second component, thereby forming a covalent bond therebetween. In situations where more than one arm of the components are substituted with electrophilic or nucleophilic groups, the components form a cross-linked hydrogel composition.

The hydrogel compositions disclosed herein are biocompatible. By "biocompatible" it is meant that the hydrogel compositions do not cause toxicity or irritation to the surrounding tissue, to the extent that would prohibit a medical professional from using the hydrogel composition on a patient.

The hydrogel compositions are also biodegradable. By "biodegradable" it is meant that the hydrogel compositions, once formed, slowly, e.g., during a period of days, weeks, or months, degrade and dissolve under normal physiological conditions. The degradation product of the disclosed hydrogels are excreted from the body of the individual patient to whom the hydrogel is applied, for example by entering the blood stream and being secreted through the kidneys and into the urine, or by being metabolized in the liver and being excreted through the intestines. The degradation products of the hydrogel compositions disclosed herein are also biocompatible.

One of the components of the two-component system disclosed herein is a compound having one or more electrophilic substituents. Thus, in one aspect, disclosed herein is a composition comprising a compound of Formula I:

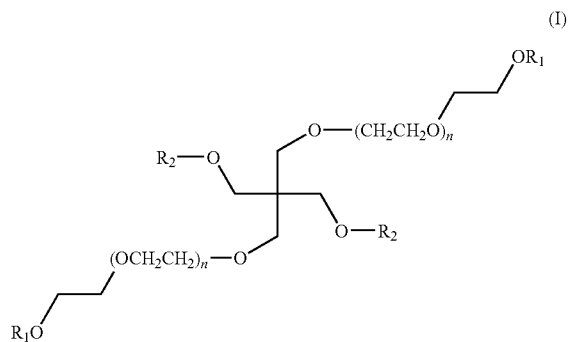

(I)

wherein
each $R_1$ is the same or different and independently hydrogen, alkyl, —C(=O)$R_3$, or —C(=O)O$R_3$;
each $R_2$ is the same or different and independently hydrogen, alkyl, or —(CH$_2$CH$_2$O)$_n$—$R_4$,
$R_3$ is hydrogen, halogen, amino, monoalkylamino, dialkylamino, alkyl, carbocyclyl, or heterocyclyl;
each $R_4$ is the same or different and independently hydrogen, alkyl, —CH$_2$CH$_2$OH, or —CH$_2$CH$_2$O$R_1$;
each n is the same or different and independently an integer greater than 1;

wherein at least one of $R_1$ is not hydrogen or alkyl (i.e., at least one of $R_1$ is —C(=O)$R_3$, or —C(=O)O$R_3$).

As used herein, "alkyl" refers to a straight or branched hydrocarbon chain radical consisting solely of carbon and hydrogen atoms, containing no unsaturation, having from one to fifteen carbon atoms. In certain embodiments, an alkyl may comprise one to eight carbon atoms. In other embodiments, an alkyl may comprise one to six carbon atoms. The alkyl is attached to the rest of the molecule by a single bond, for example, methyl, ethyl, n-propyl, 1-methylethyl (iso-propyl), n-butyl, n-pentyl, 1,1-dimethylethyl(t-butyl), 3-methylhexyl, 2-methylhexyl, and the like. Unless stated otherwise specifically in the specification, an alkyl group may be optionally substituted by one or more of the following substituents: halo (i.e., F, Br, Cl or I), cyano, nitro, oxo, thioxo, trimethylsilanyl, —O$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O $R^a$ (where t is 1 or 2), —S(O)$_p$$R^a$ (where p is 0, 1 or 2), and —S(O)$_t$N($R^a$)$_2$ (where t is 1 or 2) where each $R^a$ is independently hydrogen, alkyl, haloalkyl (i.e., alkyl substituted with one or more halo), carbocyclyl, aryl (e.g., phenyl or naphthyl), aralkyl, or heterocyclyl.

"Carbocyclyl" refers to a stable non aromatic monocyclic or polycyclic hydrocarbon radical consisting solely of carbon and hydrogen atoms, which may include fused or bridged ring systems, having from three to fifteen carbon atoms. In certain embodiments, a carbocyclyl may comprise three to ten carbon atoms. In other embodiments, a carbocyclyl may comprise five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. Unless stated otherwise specifically in the specification, an alkyl group may be optionally substituted by one or more of the following substituents: halo (i.e., F, Br, Cl or I), cyano, nitro, oxo, thioxo, trimethylsilanyl, —O$R^a$, OC(O)—$R^a$, —N($R^a$)$_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O $R^a$ (where t is 1 or 2), —S(O)$_p$$R^a$ (where p is 0, 1 or 2), and —S(O)$_t$N($R^a$)$_2$ (where t is 1 or 2) where each $R^a$ is independently hydrogen, alkyl, haloalkyl (i.e., alkyl substituted with one or more halo), carbocyclyl, aryl (e.g., phenyl or naphthyl), aralkyl, or heterocyclyl.

"Halo" refers to fluoro, chloro, bromo or iodo.

"Heterocyclyl" refers to a stable 3 to 18 membered non-aromatic ring radical that comprises two to twelve carbon atoms and from one to six heteroatoms selected from nitrogen, oxygen and sulfur. Unless stated otherwise specifically in the specification, the heterocyclyl radical may be a monocyclic, bicyclic or tricyclic ring system, which may include fused or bridged ring systems. The heteroatoms in the heterocyclyl radical may be optionally oxidized. One or more nitrogen atoms, if present, may be optionally quaternized. The heterocyclyl radical may be partially or fully saturated. The heterocyclyl may be attached to the rest of the molecule through any atom, including the heteroatom, of the ring(s). Unless stated otherwise specifically in the specification, an alkyl group may be optionally substituted by one or more of the following substituents: halo (i.e., F, Br, Cl or I), cyano, nitro, oxo, thioxo, trimethylsilanyl, —O$R^a$, OC(O)—$R^a$, —N($R^a$)$_2$, —C(O)$R^a$, —C(O)O$R^a$, —C(O)N($R^a$)$_2$, —N($R^a$) C(O)O$R^a$, —N($R^a$)C(O)$R^a$, —N($R^a$)S(O)$_t$$R^a$ (where t is 1 or 2), —S(O)$_t$O $R^a$ (where t is 1 or 2), —S(O)$_p$$R^a$ (where p is 0, 1 or 2), and —S(O)$_t$N($R^a$)$_2$ (where t is 1 or 2) where each $R^a$ is independently hydrogen, alkyl, haloalkyl (i.e., alkyl substituted with one or more halo), carbocyclyl, aryl (e.g., phenyl or naphthyl), aralkyl, or heterocyclyl. In certain embodiments, the heterocyclyl is a succinimidyl group, which is attached to the rest of the molecule through the nitrogen atom.

In some embodiments, each n is a different number. In other embodiments, all n are the same number. In yet other embodiments, two or more n are the same number. In some embodiments, each n is chosen so that every molecule in the mixture comprising the compounds of Formula I is identical. In other embodiments, different compounds in the mixture comprising the compounds of Formula I have different n or combinations of n. In some embodiments, each n is chosen so that the average molecular weight of the compounds of Formula I is about 3000 to about 30,000 g/mol. In certain embodiments, it may be desirable that each n is chosen so that the average molecular weight of the compounds of Formula I is about 10,000 g/mol. In certain embodiments, it may be desirable that each n is chosen so that the average molecular weight of the compounds of Formula I is about 20,000 g/mol.

In some embodiments, n is between 30 and 90. In other embodiments, n is between 40 and 80. In certain embodiments, n is between 50 and 70. In certain embodiments, n is approximately 56, which means that n is 56±10. When n is about 56, the average molecular weight of the compounds of Formula I is about 10,000 g/mol.

In certain embodiments, each —O$R_1$ is an electrophilic substituent that can react with a nucleophilic group such as —SH, —NH$_2$ and —OH. Exemplary —O$R_1$ include, for example, a carbonyl ester (i.e., $R_1$ is —C(=O)$R_3$) or a carbonate ester (i.e., $R_1$ is —C(=O)O$R_3$). In certain embodiments, $R_3$ is a leaving group that facilitates the reaction between the —O$R_1$ and the nucleophilic group. An example of the leaving group is a succinimidyl group.

In some embodiments, each —O$R_1$ is a different substituent. In other embodiments, all —O$R_1$ are the same substituent. In yet other embodiments, two or more —O$R_1$ are the same substituent. In some embodiments, one or more —O$R_1$ is not an electrophilic substituent. In these embodiments, —$R_1$ is preferably a hydrogen or an alkyl group. By selecting a non-electrophilic substituent for some of the arms of the compounds of Formula I, the extent of polymer cross-linking can be controlled. Therefore, if a high degree of cross-linking is desired, all of —O$R_1$ can be chosen as electrophilic substituents. However, if a lower degree of cross-linking is desired, then one or more of —O$R_1$ is selected to be a non-electrophilic substituent.

In other embodiments, the degree of cross-linking is determined by the choice of $R_2$ in the compounds of Formula I. For example, if $R_2$ is chosen such that it is a PEG-O$R_1$, then there are more than two arms (e.g., 3 arms or 4 arms) that are capable of reacting or crosslinking with nucleophilic groups, and the resulting polymer will be cross-linked to a higher degree.

In some embodiments, the compound of Formula I is a compound of Formula I.1 or a compound of Formula I.2:

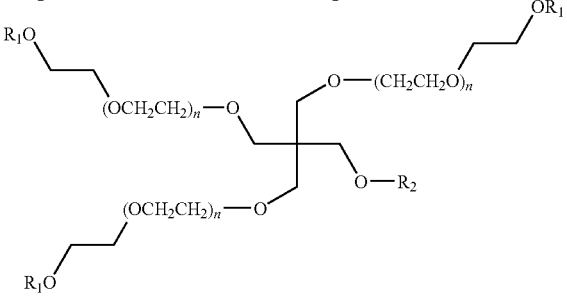

(I.2)
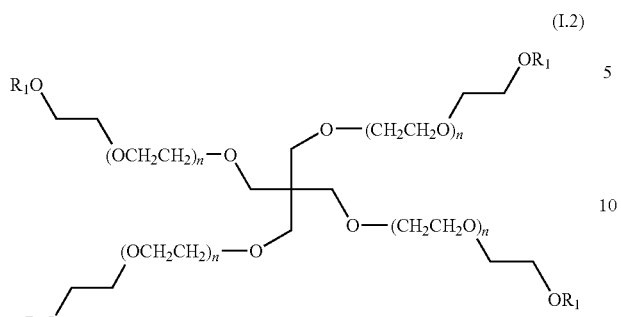
In some embodiments, at least one of —OR$_1$ is
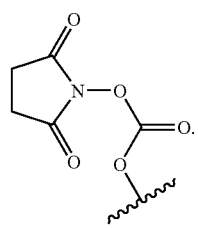 [SMILES: *OC(=O)ON1C(=O)CCC1=O]
In some embodiments, the compound of Formula I is a compound selected from the group consisting of Formulae II.1, II.2, and II.3:
(II.1)
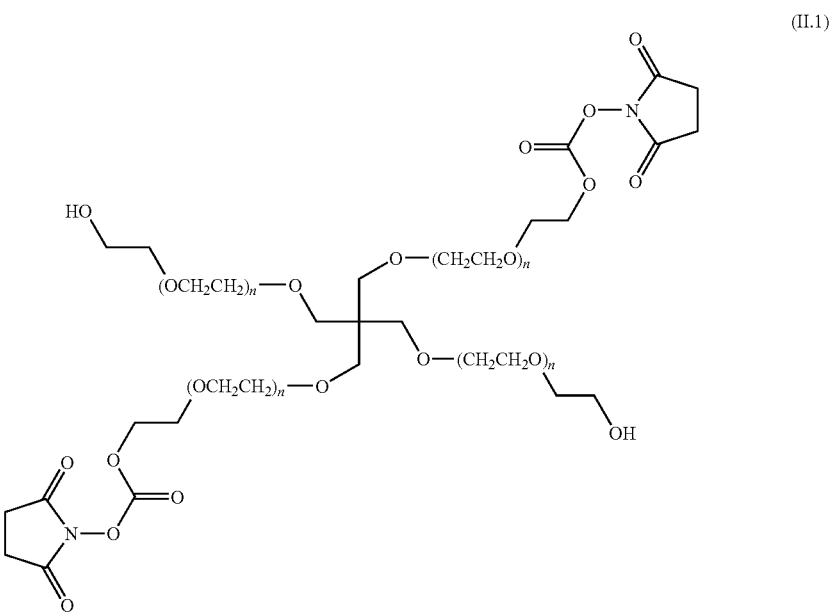
(II.2)
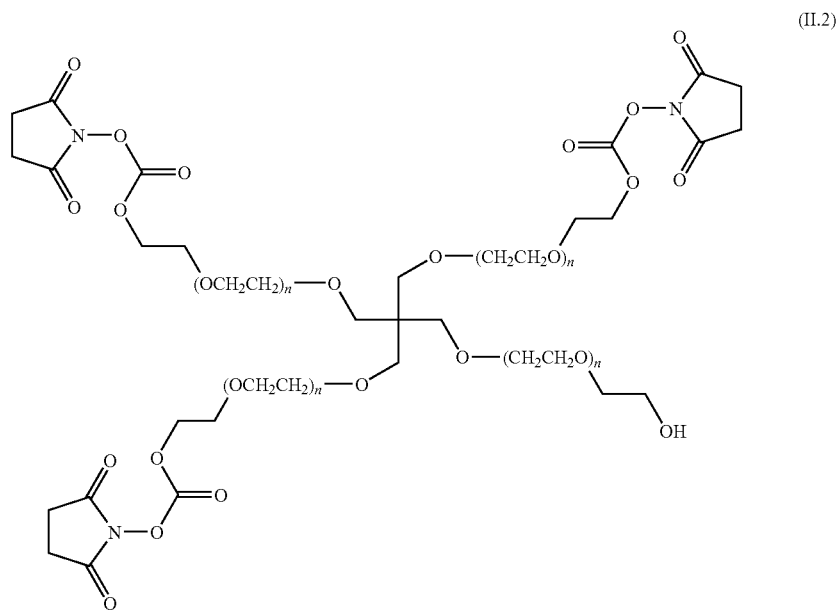

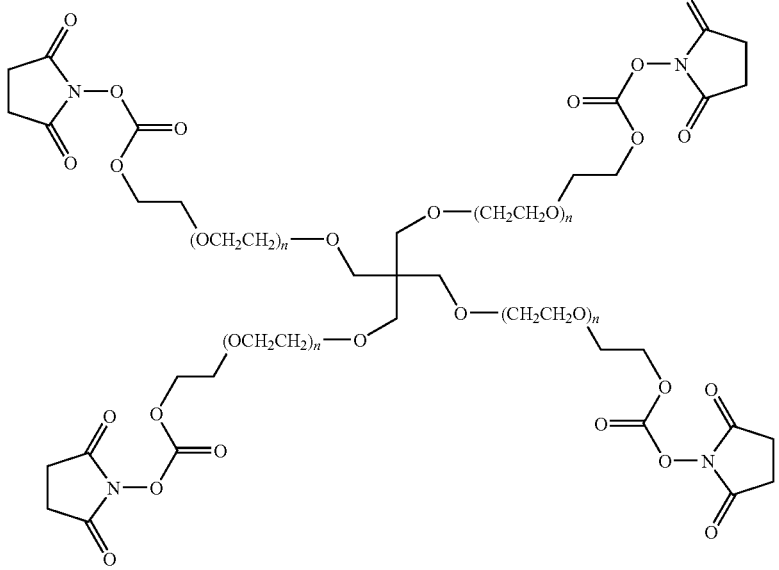

(II.3)

where each n is as defined above.

In some embodiments, when the compound of Formula I.2 is synthesized, the product will contain a mixture of compounds of Formula I, Formula I.1, and Formula I.2. In certain embodiments, these components are not separated and the mixture of all three is further reacted with a compound of Formula III (see below).

The other component of the two-component system disclosed herein is a compound having one or more nucleophilic substituents. Thus, in another embodiment, disclosed herein is a compound of Formula III:

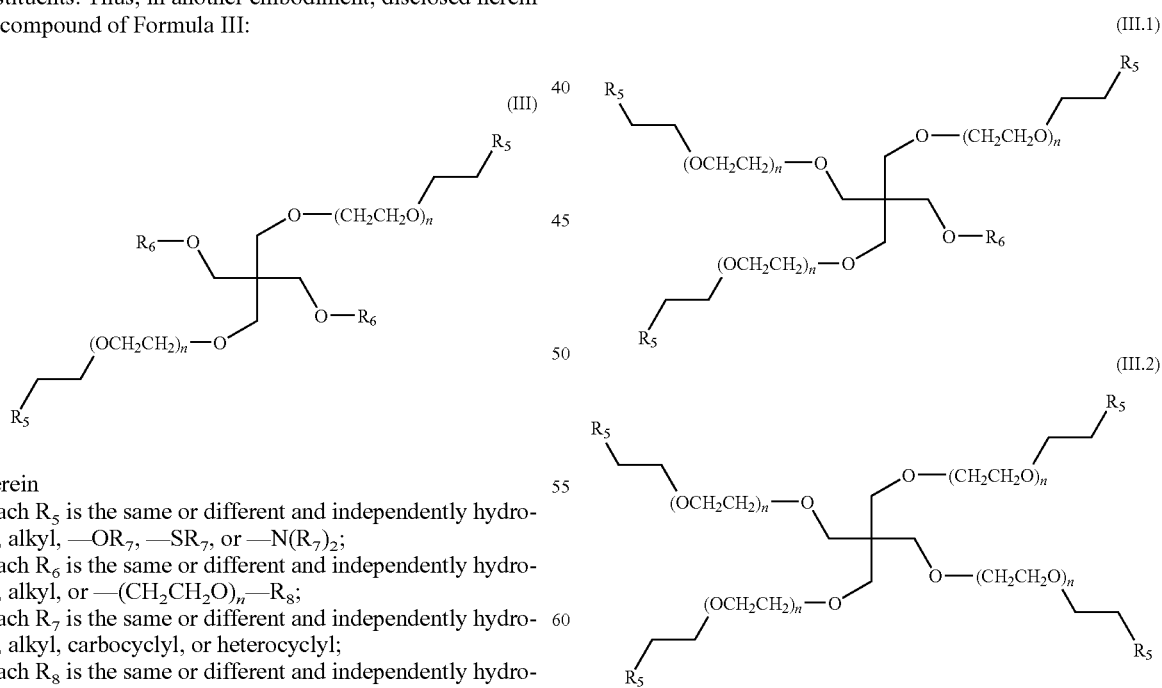

wherein
each $R_5$ is the same or different and independently hydrogen, alkyl, —$OR_7$, —$SR_7$, or —$N(R_7)_2$;
each $R_6$ is the same or different and independently hydrogen, alkyl, or —$(CH_2CH_2O)_n$—$R_8$;
each $R_7$ is the same or different and independently hydrogen, alkyl, carbocyclyl, or heterocyclyl;
each $R_8$ is the same or different and independently hydrogen, alkyl, or —$CH_2CH_2R_5$;
each n is the same or different and independently an integer greater than 1;
wherein at least one of —$R_5$ is not hydrogen or alkyl (i.e., at least one of —$R_5$ is —$OR_7$, —$SR_7$, or —$N(R_7)_2$).

In some embodiments, the degree of cross-linking is also determined by the choice of $R_6$ in the compounds of Formula III. For example, if $R_6$ is chosen such that it is a PEG-$R_5$, then there are more than two arms, for example, 3 arms or 4 arms, to the compound of Formula III and the resulting polymer will be cross-linked to a higher degree.

In some embodiments, the compound of Formula III is a compound of Formula III.1 or a compound of Formula III.2:

In certain embodiments, the following provisos apply: when both $R_6$ are —$(CH_2CH_2O)_n$—$R_8$ and both $R_8$ are —$CH_2CH_2R_5$ (e.g., Formula III.2 above), $R_5$ cannot be —OH in all four arms, or $R_5$ cannot be —$OCH_3$ in all four arms, or $R_5$ cannot be —SH in all four arms, or $R_5$ cannot be —$NH_2$ in all four arms.

In some embodiments, each n is a different number. In other embodiments, all n are the same number. In yet other embodiments, two or more n are the same number. In some embodiments, each n is chosen so that every molecule in the mixture comprising the compounds of Formula III, III.1, or III.2 is identical. In other embodiments, different compounds in the mixture comprising the compounds of Formula III, III.1, or III.2 have different n or combinations of n. In some embodiments, each n is chosen so that the average molecular weight of the compounds of Formula III, III.1, or III.2 is between 10,000-20,000 g/mol.

In certain embodiments, each $R_5$ is a nucleophilic substituent that can react with an electrophilic group. In some embodiments, each $R_5$ is a different substituent. In other embodiments, all $R_5$ are the same substituent. In yet other embodiments, two or more $R_5$ are the same substituent. In some embodiments, one or more $R_5$ is not a nucleophilic substituent. In these embodiments, $R_5$ is preferably a hydrogen or an alkyl group.

By selecting a particular compound of Formula III, III.1, or III.2, or a particular mixture thereof, the extent of polymer cross-linking can be controlled. Therefore, if a high degree of cross-linking is desired, the mixture will have exclusively, or a higher percentage of, the compound of Formula III.2. However, if a lower degree of cross-linking is desired, then the mixture will have exclusively, or a higher percentage of, the compound of Formula III.

Alternatively, or additionally, by selecting a non-nucleophilic substituent for some of the arms of the compounds of Formula III, III.1, or III.2, the extent of polymer cross-linking can be controlled. Therefore, if a high degree of cross-linking is desired, all of $R_5$ can be chosen as nucleophilic substituents. However, if a lower degree of cross-linking is desired, then one or more of $R_5$ is selected to be a non-nucleophilic substituent.

In some embodiments, each $R_5$ is independently selected from the group consisting of —OH, —SH, and —$NH_2$. In certain embodiments, at least one $R_5$ is —SH.

In another aspect, disclosed herein is a compound of Formula IV.1, IV.2, IV.3, IV.4 or IV.5:

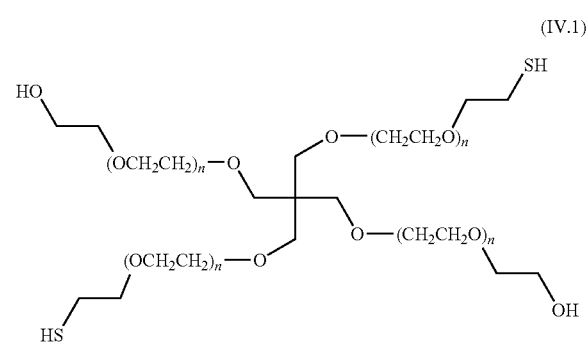

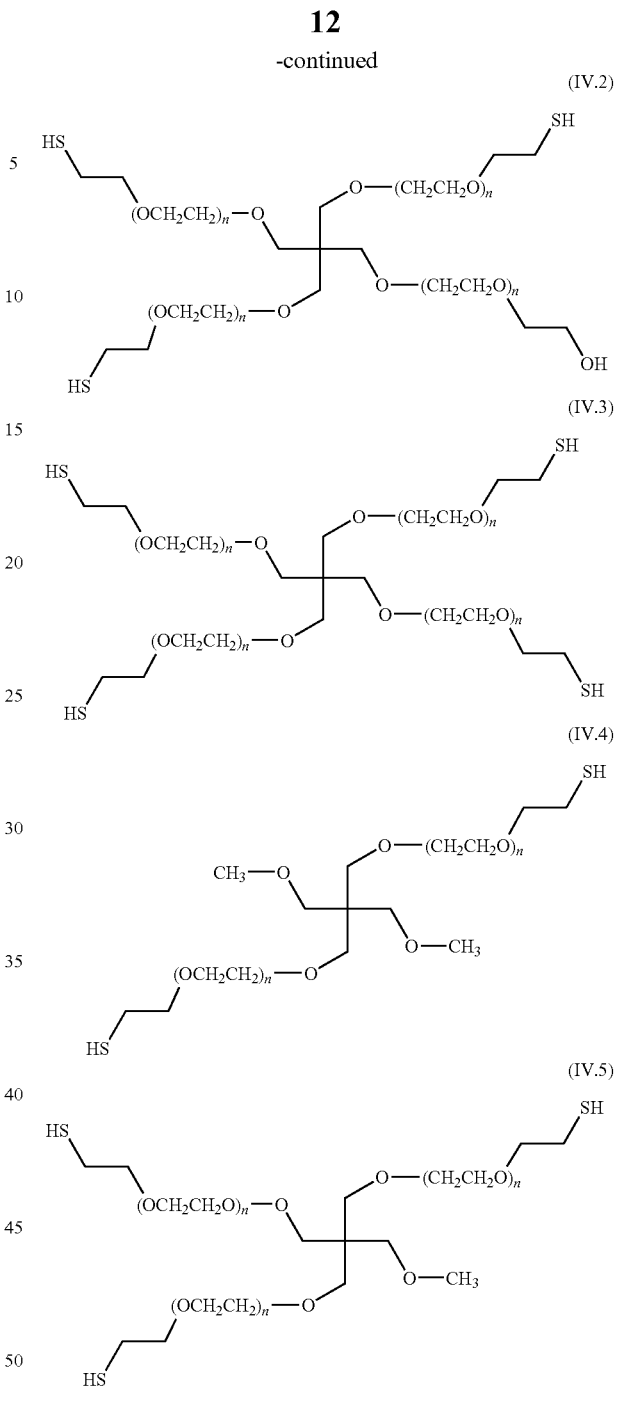

wherein each n is as defined above.

In another aspect, disclosed herein is a compound of Formula V

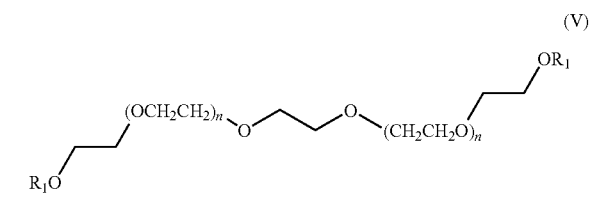

where each $R_1$ is the same or different and independently hydrogen, alkyl, —C(=O)$R_3$, or —C(=O)O$R_3$;

$R_3$ is the same or different and independently hydrogen, halogen, amino, monoalkylamino, dialkylamino, alkyl, carbocyclyl, or heterocyclyl;

each n is the same or different and independently an integer greater than 1;

wherein at least one of $R_1$ is not hydrogen or alkyl (i.e., at least one of $R_1$ is —C(=O)$R_3$, or —C(=O)O$R_3$).

In some embodiments, the compound of Formula V is a compound of Formula V.1

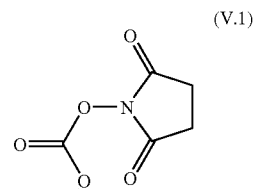

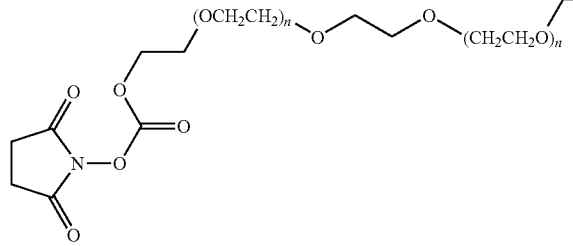

(V.1)

In some embodiments, where the compound of Formula I is in fact a mixture of the compounds of Formula I, I.1, and I.2, the degree of cross-linking can be controlled by the extent of substitution of hydroxyl substituents with NHS (N-hydroxysuccinimide) (see examples below). The more NHS substitution, the more cross-linking will be observed. Greater cross-linking creates a tighter network, which will decrease swelling. This can be advantageous in certain applications, for example the application of the gel (see below) in tight locations where gel swelling can potentially cause adverse effects.

The compositions disclosed herein can comprise two separate parts, or "components", which may be in liquid or solid form. Unless specified otherwise, in certain embodiments, the composition disclosed herein can be a system that includes two separate components prior to being mixed. The system may further include two containers or housing elements which house the two components, respectively. In some embodiments, both components are liquids, such that each can be easily applied separately to the site of administration. One of the components may be in the form of a dry powder that becomes mixed with the second component, which is in a dry powder or a liquid form. The two components are sprayed separately onto the tissue, or by mixing at the tissue site. The components can be applied separately (simultaneously or sequentially) or may first be mixed together and then the mixture applied to the tissue site. It is also possible to have both components delivered to the site as powders, to be mixed with buffer at the site of administration. In further embodiments, the system may further include a third component (e.g., a pharmaceutical compound). The third component is adapted to be mixed with the first and second component, either serially or simultaneously. In some embodiment, the third component may be combined with either the first or the second component or both, e.g., housed with either the first or the second component in the first or second housing element, respectively, or both housing elements. In other embodiments, the third component may be separate from either the first or the second component, e.g., the third component is in a separate third housing element. Unless specified otherwise, the composition or system described herein allows for mixing to the two or more components in any sequence or simultaneously.

The pH of the aqueous buffer solution that is used for each of the two (or more) composition components should be adjusted using routine optimization to achieve a final pH that is conducive to rapid gelation, without causing instantaneous gelation which interferes with the delivery process. The buffer solutions are aqueous and can be any pharmaceutically acceptable basic or acid composition. The term "buffer" is used in a general sense to refer to an acidic or basic aqueous solution, where the solution may or may not be functioning to provide a buffering effect (i.e., resistance to change in pH upon addition of acid or base) in the compositions of the present disclosure.

Low pH buffer solutions having a pH within the range of about 1.0 to 5.5, include by way of illustration and not limitation, solutions of: citric acid, hydrochloric acid, phosphoric acid, sulfuric acid, AMPSO (3-[(1,1-dimethyl-2-hydroxyethyl)amino]2-hydroxy-propane-sulfonic acid), acetic acid, lactic acid, and combinations thereof. In certain embodiments, the acidic buffer solution is a solution of citric acid, hydrochloric acid, phosphoric acid, sulfuric acid, and combinations thereof. Another exemplary acidic buffer is a solution of hydrochloric acid, having a concentration of about 6.3 mM and a pH in the range of 2.1 to 2.3.

Regardless of the precise acidifying agent, the low pH buffer preferably has a pH such that it retards the reactivity of the nucleophilic groups on the first component. For example, a pH of 2.1 is generally sufficient to retard the nucleophilicity of thiol groups. A lower pH is typically preferred when the first component contains amine groups as the nucleophilic groups. In general, the acidic buffer is an acidic solution that, when contacted with nucleophilic groups that are present as part of the first component, renders those nucleophilic groups relatively non-nucleophilic.

High pH buffer solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the basic buffer solution is a solution of carbonate salts, phosphate salts, and combinations thereof.

In general, high pH buffer is an aqueous solution that neutralizes the effect of the acidic buffer, when it is added to the homogeneous solution of the first and second components and the acid buffer, so that the nucleophilic groups of the first component regain their nucleophilic character (that has been masked by the action of the acidic buffer), thus allowing the nucleophilic groups to inter-react with the electrophilic groups of the second component.

An exemplary high pH buffer is an aqueous solution of carbonate and phosphate salts. This buffer may be prepared by combining a base solution with a salt solution. The salt solution may be prepared by combining appropriate quantities of monobasic sodium phosphate monohydrate, sodium carbonate monohydrate, and sufficient water to provide a desired final solution volume. The basic buffer is typically prepared by adding the base solution as needed to the salt solution, ultimately to provide a mixture having the desired pH, e.g., a pH of 9.65 to 9.75.

In general, the basic species present in the high pH buffer should be sufficiently basic to neutralize the acidity provided by the acidic buffer, but should not be so nucleophilic itself that it will react substantially with the electrophilic groups of the second component. For this reason, relatively "soft" bases such as carbonate and phosphate are preferred in this embodiment of the disclosure. For example, certain types of reactions (e.g., nucleophilic substitution reactions) involving sulfhydryl PEG and amino PEG need a higher (e.g., basic) pH to enhance nucleophilicity.

To illustrate the preparation of an exemplary cross-linked matrix, the liquid components of the compositions disclosed herein may each be separately prepared by adding the activated synthetic polymer (in dry form or as a concentrated solution) to a liquid medium. Suitable liquid media include aqueous buffer solutions, such as monobasic sodium phosphate/dibasic sodium phosphate, sodium carbonate/sodium bicarbonate, glutamate or acetate, at a concentration of 0.5 to 300 mM. In general, the sulfhydryl-reactive PEG is prepared in water or a dilute buffer, with a pH of between around 5 to 6. Buffers with pKs between about 8 to 10.5 for preparing the sulfhydryl-PEG component are useful to achieve fast gelation time of compositions containing mixtures of sulfhydryl-PEG/sulfhydryl-reactive PEG (e.g., succinimidyl carbonate PEG). These include carbonate, borate and AMPSO (3-[(1,1-dimethyl-2-hydroxyethyl)amino]2-hydroxy-propane-sulfonic acid).

In an alternative embodiment, both components can be mixed together in a single aqueous medium in which they are both unreactive, i.e. such as in a low pH buffer. Thereafter, they can be applied (e.g., sprayed) onto the tissue site along with a high pH buffer, after which they will rapidly react and form a gel.

In a further embodiment, both components can be combined in a dry powder mixture while in storage. When in use, the dry powder mixture can be first dissolved in a single aqueous medium, e.g., in a low pH buffer, in which they are unreactive to each other. Thereafter, they can be applied (e.g., sprayed) onto the tissue site along with a high pH buffer, after which they will rapidly react and form a gel.

In one aspect, disclosed herein is a hydrogel composition produced by a method comprising mixing a first compound and a second compound, wherein the first compound is a compound of Formula I or Formula V, as described herein, and the second compound is a compound of Formula III, as described herein. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. In some embodiments, the compound of Formula V is a compound of Formula V.1. In various embodiments, disclosed herein are a hydrogel composition produced by any of the above combinations of compound of Formula I and the compound of Formula III.

In another aspect, hydrogel compositions are provided that are produced by a method comprising combining a compound of Formula I or Formula V, as described herein, and a compound of Formula III, as described herein, wherein the compounds are each in a dry form. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. In some embodiments, the compound of Formula V is a compound of Formula V.1. The compounds of Formula I (or V) and Formula III may, for example, both be in the form of a dry powder. The combination of dry compounds is dissolved in an aqueous solution (e.g., an acidic buffer), and the solution is mixed with basic buffer to initiate crosslinking of the compounds.

In yet another aspect, disclosed herein is a method of preparing a biodegradable cross-linked composition comprising mixing, under cross-linking conditions, a first compound and a second compound, wherein the first compound is a compound of Formula I or Formula V, as described herein, and the second compound is a compound of Formula III, as described herein. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. In some embodiments, the compound of Formula V is a compound of Formula V.1.

In some embodiments, the hydrogel is prepared by reacting a compound of Formula I or Formula V with a compound of Formula III, as described herein. In other embodiments, the hydrogel is prepared by reacting a compound of Formula I with a compound of Formula III.1, as described herein. In other embodiments, the hydrogel is prepared by reacting a compound of Formula I with a compound of Formula III.2, as described herein. In some embodiments, the hydrogel is prepared by reacting a compound of Formula I.1 with a compound of Formula III, as described herein. In other embodiments, the hydrogel is prepared by reacting a compound of Formula I.1 with a compound of Formula III.1, as described herein. In other embodiments, the hydrogel is prepared by reacting a compound of Formula I.1 with a compound of Formula III.2, as described herein. In some embodiments, the hydrogel is prepared by reacting a compound of Formula I.2 with a compound of Formula III, as described herein. In other embodiments, the hydrogel is prepared by reacting a compound of Formula I.2 with a compound of Formula III.1, as described herein. In other embodiments, the hydrogel is prepared by reacting a compound of Formula I.2 with a compound of Formula III.2, as described herein. In some embodiments, the hydrogel is prepared by reacting a compound of Formula V.1 with a compound of Formula III, as described herein. In other embodiments, the hydrogel is prepared by reacting a compound of Formula V.1 with a compound of Formula III.1, as described herein. In other embodiments, the hydrogel is prepared by reacting a compound of Formula V.1 with a compound of Formula III.2, as described herein.

In some embodiments, the compounds are mixed in a first solution prior to exposing them to cross-linking conditions. In some embodiments, the first solution is an aqueous solution. In some of these embodiments, the aqueous solution is acidic, which can optionally be buffered. In certain embodiments, the first solution comprises hydrochloric acid. Thus, in some of these embodiments, the first and second compounds are provided in dry, powder form and are then mixed in an aqueous solution, e.g., an acidic solution, to provide the first solution. The first solution, then, comprises both the first compound and the second compound. However, in these embodiments, the first solution does not provide the conditions for cross-linking to occur.

In some embodiments, the first solution comprising the compounds of the disclosure is mixed in with a second solution. In some embodiments, the second solution is an aqueous solution. In some of these embodiments, the second solution is basic, which can optionally be buffered. In certain embodiments, the second solution comprises monobasic sodium phosphate/sodium carbonate buffer at pH 9-11, or pH 9-10, or pH 10-11. In certain embodiments, the second solution comprises a carbonate/bicarbonate buffer having a pH of 9.7 to 10.8. Such buffers can be useful to decrease the gel time, i.e., speed up gel formation. Also, such a buffer has low buffering capacity so that the gel can return to physiological pH more quickly.

After cross-linking has occurred, a hydrogel is formed. Because the first solution is acidic, the final pH of the hydrogel is less than the pH of the second solution. In some embodiments, the final pH of the hydrogel is less than 9. The final pH of the hydrogel may be impacted by the extent of functional group substitution on the reaction components (in particular, the extent of NHS substitution).

In some embodiments, the first solution and the second solution are mixed by simultaneously administering (e.g., spraying) the first and the second solutions into the same space. Simultaneous administration of the two solutions facilitates efficient mixing and rapid gellation.

Spraying the solutions into the desired space has the effect of speeding the reaction time between the compounds of Formula I (or V) and III. When a solution is sprayed, it is turned into aerosols, or small particles or droplets. The surface to volume ratio of the solution is thus increased greatly. Since most of the reaction between the two compounds takes place at the surface of the droplets, where the two compounds come into contact, increasing the surface to volume ratio greatly increases the incidents of contact between the two compounds and therefore increases the reaction rate.

In some embodiments, the first and the second solutions are mixed together immediately prior to the application of the mixture to the site of use. In some embodiments, the first and second solutions are mixed together within a syringe and then injected through a cannula tip or needle to the site of use (e.g., laparoscopically or topically). In other embodiments, one solution is applied to the site of use, whether sprayed, poured, or added dropwise, and shortly thereafter the second solution is applied to the same site, whether sprayed, poured, or added drop-wise. Depending on the nature of the surgical site, it may be more practical to utilize a laparoscopic or pressurized delivery device. Representative examples of devices that may be used to deliver the hydrogels described herein include those described in U.S. 2006/0071025 A1, incorporated herein by reference.

The terms "site of use," "same space," or the like that represent the location where the two solutions come into contact with each other can refer to any location where it is desirable to form the hydrogels disclosed herein. For example, in a laboratory setting, the same space or the site of use represents a laboratory vessel into which the two solutions are introduced and in which the hydrogel is formed. In the context of treatment of patients after surgery, the "site of use" or the "same space" refers to the site of surgery where a surgical incision or cut has been made. The surgeon, at the conclusion of the surgical operation, can apply the two solutions in a manner described herein to the surgical site in order to form a hydrogel layer over the surgical site. The surgeon can choose to apply the hydrogel compositions described herein or for the reasons described in the above-incorporated U.S. Pat. Nos. 5,874,500, 6,051,648, 6,312,725, 6,458,889, 6,495,127, 6,624,245, 7,176,256, and U.S. 2005/0281883 A1.

As noted above, the hydrogel compositions described herein are biocompatible and, therefore, non-immunogenic and exhibit low levels of toxicity and/or antigenicity. In addition, the hydrogel compositions are biodegradable.

The use of the hydrogel compositions disclosed herein is more advantageous under certain circumstances than the hydrogel compositions described heretofore. For instance, the present hydrogel compositions degrade within 14-200 days from the time of application and, therefore, last longer, i.e., decompose and degrade at a slower rate, than other similar hydrogel compositions. The present hydrogel compositions also cause significantly less swelling of the surrounding tissue than other similar hydrogel compositions.

The difference in the properties of the hydrogel compositions disclosed herein and those of the other similar hydrogel compositions is in part due to the type of bond that is formed when the hydrogel is synthesized. In some of the known hydrogel compositions, such as COSEAL (available from Baxter Healthcare Corporation), a thioester bond is formed, as shown in the reaction below.

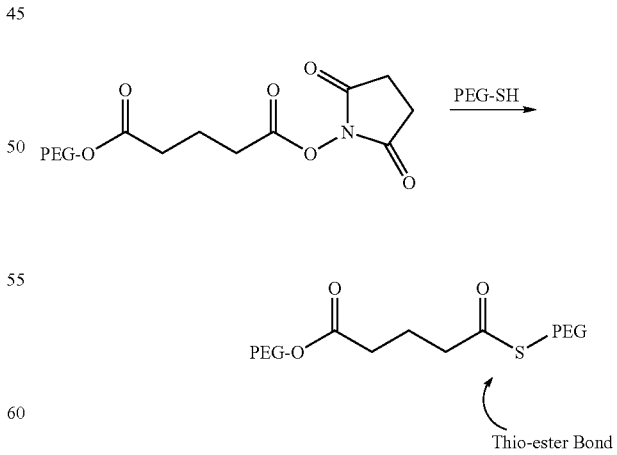

However, the hydrogel compositions described herein are formed when a carbonothionate bond is formed between the compounds of Formula I (or V) and the compounds of Formula III, as shown in the reaction below.

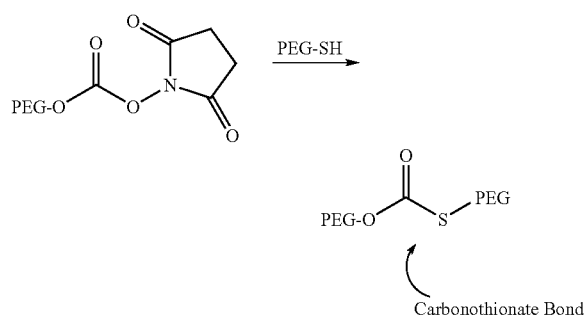

Carbonothionate Bond

The carbonothionate bond undergoes hydrolysis under physiological conditions at a slower rate than the thioester bond, thereby rendering the hydrogel compositions of the present disclosure to degrade at a slower rate in the patient's body than similar hydrogel compositions.

Furthermore, COSEAL utilizes a glutarate linker, such that the electrophilic PEG components contain two ester bonds. The electrophilic PEG component in the compositions disclosed herein does not contain a glutarate linker or any ester bonds. The lack of an ester bond in the linker further contributes to the improved stability of the hydrogels disclosed herein.

In another aspect, disclosed herein is a method of sealing a wound comprising administering to the wound a biocompatible hydrogel, wherein the biocompatible hydrogel is produced by a method comprising mixing a first solution comprising a first compound and a second solution comprising a second compound, wherein the first compound is a compound of Formula I or Formula V, as described herein, and the second compound is a compound of Formula III, as described herein. In some embodiments, the compound of Formula I is a compound of Formula II. In certain embodiments, the compound of Formula III is a compound of Formula IV.

In yet another aspect, a method of sealing a wound is provided comprising administering to the wound a biocompatible hydrogel, wherein the biocompatible hydrogel is produced by a method comprising combining a compound of Formula I or Formula V, as described herein, and a compound of Formula III, as described herein, wherein the compounds are each in a dry form. In some embodiments, the compound of Formula I is a compound selected from the group consisting of Formula IV.1, Formula IV.2, Formula IV.3, Formula IV.4 and Formula IV.5. In certain embodiments, the compound of Formula III is a compound selected from the group consisting of Formula IV.1, Formula IV.2, Formula IV.3, Formula IV.4 and Formula IV.5. The compounds of Formula I and Formula III may, for example, both be in the form of a dry powder. The combination of dry compounds is dissolved in an aqueous solution (e.g., an acidic buffer), and the solution is mixed with basic buffer to initiate crosslinking of the compounds.

The hydrogels, described herein, may inhibit bleeding and/or leakage of body fluids (e.g., serosal fluids) from the wound site. In some embodiments, the hydrogel is administered after the wound has been sutured. In other embodiments, the hydrogel is administered before the wound has been sutured. In some embodiments, the wound is a surgically-induced wound (e.g., an internal wound or a wound to the skin). In other embodiments, the wound is caused by an external trauma.

Another use of the hydrogel compositions described herein is to coat tissues in order to prevent the formation of adhesions following surgery or injury to internal tissues or organs. In a general method for coating tissues to prevent the formation of adhesions following surgery, the first solution and the second solution are mixed and a thin layer of the mixture is then applied to the tissues comprising, surrounding, and/or adjacent to the surgical site before substantial crosslinking has occurred. Application of the mixture to the tissue site may be by extrusion, brushing, spraying, or by any other convenient means.

Following application of the mixture to the surgical site, crosslinking is allowed to continue in situ prior to closure of the surgical incision. Once crosslinking has reached equilibrium, tissues that are brought into contact with the coated tissues will not adhere thereto. The surgical site can then be closed using conventional means (sutures, etc.).

In general, compositions that achieve complete crosslinking within a relatively short period of time (i.e., <15 minutes following admixture of the reactive components) are preferred for use in the prevention of surgical adhesions, so that the surgical site may be closed relatively soon after completion of the surgical procedure.

Thus, in another aspect, disclosed herein is a method of preventing post-surgical adhesion comprising administering to a tissue a biocompatible hydrogel, wherein the biocompatible hydrogel is produced by a method comprising mixing a first solution comprising a first compound and a second solution comprising a second compound, wherein the first compound is a compound of Formula I or Formula V, as described herein, and the second compound is a compound of Formula III, as described herein. In some embodiments, the compound of Formula I is a compound of Formula II. In certain embodiments, the compound of Formula III is a compound of Formula IV.

In another aspect, a method of preventing post-surgical adhesion is provided comprising administering to a tissue a biocompatible hydrogel, wherein the biocompatible hydrogel is produced by a method comprising combining a compound of Formula I or Formula V, as described herein, and a compound of Formula III, as described herein, wherein the compounds are each in a dry form. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. In some embodiments, the compound of Formula V is a compound of Formula V.1. The compounds of Formula I or Formula V and Formula III may, for example, both be in the form of a dry powder. The combination of dry compounds is dissolved in an aqueous solution (e.g., an acidic buffer), and the solution is mixed with basic buffer to initiate crosslinking of the compounds.

In some embodiments, the hydrogel is administered before the skin covering the tissue is apposed and sutured. In other embodiments, the hydrogel is administered after the surgical incision has been sutured.

2. Drug-Loaded Hydrogel Systems

The cross-linked hydrogels formed as described herein comprise interstitial space in which certain molecules can be trapped for later release. In some embodiments, these molecules, such as pharmaceuticals, are mixed with either the low pH solution, or the high pH solution, or both, prior to the mixing of the first and the second solutions. In other embodiments, these pharmaceutical compounds are provided in a dry, powder form and are mixed with the dry first compound (e.g., a compound with a plurality of electrophilic groups) and second compound (e.g., a compound with a plurality of nucleophilic groups) before the addition of the aqueous solution to form the first solution. In other embodiments, pharmaceuticals compounds are provided in a first aqueous solution (e.g., as a suspension of particles in a basic buffer). A mixture of the dry first and second compounds is combined with a second aqueous solution (e.g., an acidic buffer) to form a second solution. Once the first and the second solutions are mixed together and the hydrogel is formed, the molecules are trapped in the interstitial space formed within the hydrogel. As discussed above, the hydrogel compositions described herein are biocompatible and biodegradable. As the hydrogel composition degrades slowly within the physiological environment to which it was applied, the molecules trapped therein are released to the same physiological environment. Alternatively, or in addition, release of the pharmaceutical substance occurs by diffusion through the hydrogel prior to its degradation. In addition, since the hydrogel is formulated in situ and adheres well to tissue, no direct injection into tissue is required for drug release.

Accordingly, in addition to the uses previously contemplated, the hydrogels described herein are particularly well-suited for controlled local delivery of analgesics and local anesthetics for the management of post-operative pain.

Thus, in further embodiments, the hydrogels disclosed herein further comprise an analgesic that can reduce post-surgical pain. More specifically, disclosed herein are compositions comprising a biocompatible hydrogel and an analgesic, where the biocompatible hydrogel is produced by a method comprising: mixing a first compound and a second compound to obtain a first mixture, adding a first aqueous solution to the first mixture to obtain a first solution, adding a second aqueous solution to the first solution, where the first compound is a compound of Formula I or Formula V, and the second compound is a compound of Formula III, as described above. In various embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. Unless specified otherwise, the hydrogels disclosed herein include any and all combinations of the first compound of Formula I (e.g., Formula II.1, Formula II.2, or Formula II.3) or Formula V, and the second compound of Formula III (e.g., IV.1, Formula IV.2, Formula IV.3, Formula IV.4 or Formula IV.5).

In a further embodiment, disclosed herein is a composition comprising a biocompatible hydrogel and an analgesic, where the biocompatible hydrogel is produced by a method comprising mixing a first solution comprising a first compound and a second solution comprising a second compound, where the first compound is a compound of Formula I or Formula V, as described herein, and the second compound is a compound of Formula III, as described herein. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. Unless specified otherwise, the hydrogels disclosed herein include any and all combinations of the first compound of Formula I (e.g., Formula II.1, Formula II.2, or Formula II.3) or Formula V, and the second compound of Formula III (e.g., IV.1, Formula IV.2, Formula IV.3, Formula IV.4 or Formula IV.5).

In yet another aspect, a composition is provided comprising a biocompatible hydrogel and an analgesic, where the biocompatible hydrogel is produced by a method comprising combining a compound of Formula I or Formula V, as described herein, and a compound of Formula III, as described herein, wherein the compounds are each in a dry form; adding a first aqueous solution to the dry mixture to obtain a first solution, adding a second aqueous solution to the first solution to initiate crosslinking. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5. The compounds of Formula I and Formula III may, for example, both be in the form of a dry powder. The combination of dry compounds is dissolved in an aqueous solution (e.g., an acidic buffer), and the solution is mixed with basic buffer to initiate cross-linking of the compounds. Unless specified otherwise, the hydrogels disclosed herein include any and all combinations of the first compound of Formula I (e.g., Formula II.1, Formula II.2, or Formula II.3) or Formula V, and the second compound of Formula III (e.g., IV.1, Formula IV.2, Formula IV.3, Formula IV.4 or Formula IV.5).

In some embodiments, the analgesic is mixed in the first solution prior to the mixing of the first and the second solutions. In other embodiments, the analgesic is mixed in the second solution prior to the mixing of the first and the second solutions. In yet other embodiments, the analgesic is mixed in both the first and the second solutions prior to the mixing of the first and the second solutions. In still other embodiments, the analgesic is provided in a dry form and is mixed with the dry forms of the compounds of Formula I and III before the first solution is prepared.

Furthermore, the hydrogel compositions described herein are a useful and efficient manner for applying pharmaceuticals or drugs to a site of use in a slow-release, or time-release formulation.

As used herein, "pharmaceuticals", "drugs" or "biologically active agents" interchangeably refer to one or more compound (e.g., organic molecules) that exerts biological effects in vivo. The drugs within the scope of this disclosure include but are not limited to those which inhibit one or a combination of processes including but not limited to cell division, cell secretion, cell migration, cell adhesion, cytokine, chemokine (or other inflammatory activator) production and/or release, angiogenesis, and/or free radical formation and/or release, and/or coagulation cascade. In particular, one aspect of the disclosure involves pharmacological alteration of cellular and/or non-cellular processes involved in the development and/or maintenance of surgical adhesions. Another aspect of this disclosure involves pharmacological alteration of cellular and/or non-cellular processes involved in the development and/or maintenance of restenosis. Thus, pharmacological agents (i.e., drugs) within the scope of this disclosure include but are not limited to those which inhibit one or a combination of processes including but not limited to cell division, cell secretion, cell migration, cell adhesion, cytokine, chemokine (or other inflammatory activator) production and/or release, angiogenesis, and/or free radical formation and/or release. Drugs within the scope of this disclosure may inhibit or affect other processes involved in the scarring process. In addition, an aspect of this disclosure involves pharmacological alteration of cellular and/or non-cellular processes which increase the development of fibrosis. Thus, pharmacological agents (i.e., drugs) within the scope of this disclosure include but are not limited to those which increase one or a combination of processes including but not limited to cell division, cell secretion, cell migration, cell adhesion, cytokine, chemokine (or other inflammatory activator) production and/or release, angiogenesis, and/or free radical formation and/or release. Drugs within the scope of this disclosure may increase or affect other processes involved in the scarring process. A further aspect of the disclosure is directed to hemostatic agent and/or adhesion prevention agent, the addition of a drug can effect an increase or decrease in fibrosis, and/or result in tissue augmentation and/or increase or reduction in surgical adhesions depending on the drug mechanism. For example, a drug which decreases fibrosis will be expected to reduce surgical adhesions. Furthermore, the drug-loaded formulation may increase the sealant and/or hemostatic properties of the formulation, especially when the agent acts to increase fibrosis. Yet another aspect of the disclosure involves pharmacological alteration of cellular and/or non-cellular processes involved in the development and/or maintenance of surgical adhesions or restenosis or in more general terms inhibit one or more processes involved in fibrosis. Thus, pharmacological agents within the scope of this disclosure include but are not limited to those which inhibit one or a combination of processes such as cell division, cell secretion, cell migration, cell adhesion, extracellular matrix production, cytokine (e.g., TNF alpha, IL-1, IL-6), or other inflammatory activator, e.g., chemokines (e.g., MCP-1 or IL-8)) production and/or release, angiogenesis, and/or free radical formation and/or release. Suitable fibrosis-, adhesion- or stenosis-inhibiting agents are disclosed in detail in, for example, WO2004/060346, WO 2005/051452, WO 2006/13547, and WO 2007/089878, and are also readily determined based upon the in vitro and in vivo (animal) models such as those provided in, e.g., WO2004/060346. The references are included herein by reference in their entireties.

Within other embodiments, the drugs may include one or more fibrosing agents, fibrosis-inducing agents and/or adhesion-inducing agents, representative examples of which may be found, without limitation, in International Publication Nos. WO 2005/046746, WO 2005/046747, and WO 2006/124021, the entire disclosures of which are included herein by reference.

Thus, in various embodiments, disclosed herein is a composition comprising a biocompatible hydrogel and a drug, where the biocompatible hydrogel is produced by a method comprising mixing a first solution comprising a first compound and a second solution comprising a second compound, where the first compound is a compound of Formula I, as described herein, and the second compound is a compound of Formula III, as described herein. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5.

In more specific embodiments, a variety of drugs may be included in the compositions and methods of the present disclosure. These drugs and drug classes are set forth in detail in, e.g., WO2004/060346. The following are specific aspects of the present disclosure, which are exemplary only: in one aspect, the compositions and methods of the disclosure employ (i.e., include in a composition, or use in a method) a cell cycle inhibitor; in one aspect, the compositions and methods of the disclosure employ paclitaxel; in one aspect, the compositions and methods of the disclosure employ doxorubicin; in one aspect, the compositions and methods of the disclosure employ mitoxantrone; in one aspect, the compositions and methods of the disclosure employ podophyllotoxin (e.g., etoposide); in one aspect, the compositions and methods of the disclosure employ an immunomodulatory agents; in one aspect, the compositions and methods of the disclosure employ rapamycin; in one aspect, the compositions and methods of the disclosure employ everolimus; in one aspect, the compositions and methods of the disclosure employ tacrolimus; in one aspect, the compositions and methods of the disclosure employ biolimus; in one aspect, the compositions and methods of the disclosure employ a heat shock protein 90 antagonist; in one aspect, the compositions and methods of the disclosure employ geldanamycin; in one aspect, the compositions and methods of the disclosure employ a HMG CoA Reductase inhibitor; in one aspect, the compositions and methods of the disclosure employ simvastatin; in one aspect, the compositions and methods of the disclosure employ an IMPDH Inhibitor; in one aspect, the compositions and methods of the disclosure employ mycophenolic acid; in one aspect, the compositions and methods of the disclosure employ 1-alpha-25 dihydroxy vitamin D3; in one aspect, the compositions and methods of the disclosure employ an antimycotic agent; in one aspect, the compositions and methods of the disclosure employ sulconizole; in one aspect, the compositions and methods of the disclosure employ a P38 MAP kinase inhibitor; in one aspect, the compositions and methods of the disclosure employ SB220025; in one aspect, the compositions and method of the disclosure employ talcum powder; in one aspect, the compositions and method of the disclosure employ metallic beryllium and oxides thereof; in one aspect, the compositions and method of the disclosure employ copper; in one aspect, the compositions and method of the disclosure employ silk; in one aspect, the compositions and method of the disclosure employ silica; in one aspect, the compositions and method of the disclosure employ crystalline silicates; in one aspect, the compositions and method of the disclosure employ talc; in one aspect, the compositions and method of the disclosure employ quartz dust; in one aspect, the compositions and method of the disclosure employ ethanol; in one aspect, the compositions and method of the disclosure employ a component of extracellular matrix; in one aspect, the compositions and method of the disclosure employ fibronectin; in one aspect, the compositions and method of the disclosure employ collagen; in one aspect, the compositions and method of the disclosure employ fibrin; in one aspect, the compositions and method of the disclosure employ fibrinogen; in one aspect, the compositions and method of the disclosure employ polylysine; in one aspect, the compositions and method of the disclosure employ poly(ethylene-co-vinylacetate); in one aspect, the compositions and method of the disclosure employ chitosan; in one aspect, the compositions and method of the disclosure employ N-carboxybutylchitosan; in one aspect, the compositions and method of the disclosure employ a RGD protein; in one aspect, the compositions and method of the disclosure employ vinyl chloride; in one aspect, the compositions and method of the disclosure employ a polymer formed from vinyl chloride; in one aspect, the compositions and method of the disclosure employ a cyanoacrylate adhesive; in one aspect, the compositions and method of the disclosure employ an adhesive comprising crosslinked poly(ethylene glycol) derived material and methylated collagen; in one aspect, the compositions and method of the disclosure employ an inflammatory cytokine; in one aspect, the compositions and method of the disclosure employ an inflammatory cytokine selected from the group consisting of TGFb, PDGF, VEGF, bFGF, TNFa, NGF, GM-CSF, IGF-a, IL-1, IL-8, IL-6, and growth hormone; in one aspect, the compositions and method of the disclosure employ a connective tissue growth factor (CTGF); in one aspect, the compositions and method of the disclosure employ a bone morphogenic protein (BMP); in one aspect, the compositions and method of the disclosure employ a BMP selected from BMP-2, BMP-3, BMP-4, BMP-5, BMP-6, or BMP-7; in one aspect, the compositions and method of the disclosure employ bleomycin; in one aspect, the compositions and method of the disclosure employ an analogue or derivative of bleomycin; in one aspect, the compositions and method of the disclosure employ a proliferative agent that stimulates cellular proliferation; in one aspect, the compositions and method of the disclosure employ dexamethasone and analogues and derivatives thereof; in one aspect, the compositions and method of the disclosure employ isotretinoin and analogues and derivatives thereof; in one aspect, the compositions and method of the disclosure employ 17-β-estradiol and analogues and derivatives thereof; in one aspect, the compositions and method of the disclosure employ estradiol and analogues and derivatives thereof; in one aspect, the compositions and method of the disclosure employ diethylstibesterol and analogues and derivatives thereof; in one aspect, the compositions and method of the disclosure employ cyclosporine A and analogues and derivatives thereof; in one aspect, the compositions and method of the disclosure employ All-trans retinoic acid (ATRA) and analogues and derivatives thereof. Additional drugs that may be employed in the present disclosure are set forth in WO 2005/046746, WO 2005/046747, WO 2006/124021, WO2004/060346, WO 2005/051452, WO 2006/13547, and WO 2007/089878, which are incorporated herein by reference in their entireties.

In one specific embodiment, the drug may be one or more hemostatic proteins, including without limitation, thrombin, fibrin, fibrinogen, blood factors, coagulation factors (e.g., Factors VIII and XIII). Thus, in one embodiment, disclosed herein is a composition comprising a biocompatible hydrogel and an analgesic, where the biocompatible hydrogel is produced by a method comprising mixing a first solution comprising a first compound and a second solution comprising a second compound, where the first compound is a compound of Formula I, as described herein, and the second compound is a compound of Formula III, as described herein. In some embodiments, the compound of Formula I is a compound selected from the group consisting of Formula II.1, Formula II.2, and Formula II.3. In certain embodiments, the compound of Formula III is a compound selected from the group consisting of Formula IV.1, Formula IV.2, Formula IV.3, Formula IV.4 and Formula IV.5.

In further embodiments, the two reactive compounds and the gel matrix that forms when they are mixed together can be represented as follows:

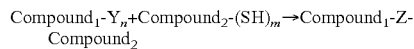

Compound$_2$ has multiple (m≥2) sulfhydryl groups (SH) that react with Compound$_1$, which has multiple (n≥2) sulfhydryl-reactive groups (Y). When mixed together, the two compounds become interconnected (e.g., cross-linked) via formation of a covalent linkage (Z). Compound$_1$ and Compound$_2$ may be directly linked via a covalent bond. Alternatively, Compound$_1$ and Compound$_2$ may be bonded through a linker. However, when m+n≥5, and appropriate ratios of the two components are utilized, the two compounds form multiple attachments to one another resulting in a three-dimensional polymer matrix. In some embodiments n=2. In other embodiments, n=3. In other embodiments, n=4. In some embodiments m=2. In other embodiments, m=3. In other embodiments, m=4. Preferably, both compounds contain at least four functional groups, since such multifunctionality results in a cross-linked gel matrix with greater overall cohesive strength than one formed from compounds having a lower functionality. In a particularly preferred embodiment, the first compound contains four sulfhydryl-reactive groups and the second compound contains four SH groups.

As described above, each of the compounds has multiple functional groups, either sulfhydryl groups or sulfhydryl-reactive groups. The non-reactive remainder of the compound is considered to be its "core". At least one of the two compounds must have a polymer core in order to form an efficient gel matrix. When one of the compounds contains a polymer core, the other compound can be a small organic molecule with multiple sulfhydryl-reactive groups. However, for most applications, both compounds have a polymer core. The polymer cores may be the same or different.

The polymer core may be a synthetic polyamino acid, a polysaccharide, or a synthetic polymer. A preferred polymer core material is a synthetic hydrophilic polymer. Suitable synthetic hydrophilic polymers include, inter alia, polyalkylene oxide, such as polyethylene oxide ($(CH_2CH_2O)_n$), polypropylene oxide ($(CH(CH_3)CH_2O)_n$) or a polyethylene/polypropylene oxide mixture ($(CH_2CH_2O)_n$—$(CH(CH_3)CH_2O)_n$). A particularly preferred synthetic hydrophilic polymer is a polyethylene glycol (PEG) having a molecular weight within the range of about 100 to about 100,000 g/mol, more preferably about 1,000 to about 20,000 g/mol. More preferably still, when the polymer core is polyethylene glycol, it generally has a molecular weight within the range of about 7,500 to about 20,000 g/mol. Most preferably, the polyethylene glycol has a molecular weight of approximately 10,000 g/mol.

In some embodiments, Compound$_1$ and Compound$_2$ each independently include more than one polyethylene glycol chain in the polymer core. The polyethylene glycol chains are connected together by a core moiety. The core moiety may be a straight chain or branched alkyl group. The alkyl group may be substituted by oxy groups such that there is an oxygen linker between the core moiety and the polyethylene glycol chains. In other embodiments, the core moiety is an ether moiety. Examples of a core moiety include, but are not limited to, ethyl, propyl, pentaerythritol (2,2-dihydroxymethyl-propan-1,3-diol) ($HOCH_2C(CH_2OH)_2CH_2OH$), and di(2,2-bishydroxmethylbutyl)ether (($CH_3CH_2C(CH_2OH)_2CH_2$—)$_2$O).

When only one of the reactive compounds comprises a polymer core, the other reactive compound may be a multifunctionally active small organic molecule. Such compounds include the di-functional di-N-hydroxy-succinimidyl esters and di-maleimidyl compounds, as well as others well known commercially available compounds (Pierce Chemical Co., Rockford, Ill.). In addition, low molecular weight multi-functional reactive compounds can be readily synthesized using routine organic chemistry techniques.

One such compound is a pentaerythritol coupled to four glutarates, with each arm capped with N-hydroxy-succinimidyl esters (NHS), shown in Formula VI (also referred to as pentaerythritol poly(ethylene glycol)ether tetra-N-hydroxy-succinimidyl glutarate or SG-PEG). Analogous compounds can be synthesized from inositol (radiating 6 arm), lactitol (9 arm) or sorbitol (linear 6-arm). Alternative end-capped sulfhydryl-reactive groups include sulfhydryl (which may react with another sulfhydryl group under certain conditions), maleimidyl, vinyl-sulfone, and the like. Additional examples of sulfhydryl-reactive compounds include those described in co-pending U.S. application Ser. No. 10/749,123, incorporated herein by reference. The polymer or the small molecule can carry any reactive end group as long as there are reactive pairs in the composition such as NHS and SH, maleimidyl and SH, and the like.

As disclosed herein, the linkage Z comprises the sulfur atom in the sulfhydryl group-containing compound and a covalent bond from that sulfur atom to the carbon or sulfur atom in the sulfhydryl-reactive group-containing compound. Accordingly, the linkage may be a thioester, a thioether, a disulfide, or the like.

A wide variety of sulfhydryl-reactive groups and the types of linkages they form when reacted with sulfhydryl groups are well known in the scientific literature. For example, see Bodanszky, M., Principles of Peptide Synthesis, 2nd ed., pages 21 to 37, Springer-Verlag, Berlin (1993); and Lundbland, R. L., Chemical Reagents for Protein Modification, 2nd ed., Chapter 6, CRC Press, Boca Raton, Fla. (1991).

For most applications, sulfhydryl reactive groups that react with sulfhydryl groups to form thioester linkages are preferred. Such compounds are described in U.S. Pat. No. 6,312,725 (depicted in FIG. 1 therein) and include, inter alia, the following compounds, with the numbers in parentheses corresponding to the structures shown in FIG. 1: mixed anhydrides, such as PEG-glutaryl-acetyl-anhydride (1), PEG-glutaryl-isovaleryl-anhydride (2), PEG-glutaryl-pivalyl-anhydride (3) and related compounds as presented in Bodanszky, p. 23; Ester derivatives of phosphorus, such as structures (4) and (5); ester derivatives of p-nitrophenol (6) of p-nitrothiophenol (7), of pentafluorophenol (8), of structure (9) and related active esters as presented by Bodanszky, pp. 31-32, and Table 2; esters of substituted hydroxylamines, such as those of N-hydroxy-phthalimide (10), N-hydroxy-succinimide (11), and N-hydroxy-glutarimide (12), as well as related structures in Bodanszky; Table 3; esters of 1-hydroxy-benzotriazole (13), 3-hydroxy-3,4-dihydro-benzotriazine-4-one (14) and 3-hydroxy-3,4-dihydro-quinazoline-4-one; derivatives of carbonylimidazole; and isocyanates. With these compounds, auxiliary reagents can also be used to facilitate bond formation, such as 1-ethyl-3-[3-dimethylaminopropyl]carbodiimide can be used to facilitate coupling of carboxyl groups (i.e., glutarate and succinate) with sulfhydryl groups.

In addition to the sulfhydryl reactive compounds that form thioester linkages, various other compounds can be utilized that form other types of linkages. For example, compounds that contain methyl imidate derivatives form imido-thioester linkages with sulfhydryl groups.

Alternatively, sulfhydryl reactive groups can be employed that form disulfide bonds with sulfhydryl groups, such as ortho pyridyl disulfide, 3-nitro-2-pyridenesulfenyl, 2-nitro-5-thiocyanobenzoic acid, 5,5'-dithio-bis(2-nitrobenzoic acid), derivatives of methane-thiosulfate, and 2,4-dinitrophenyl cysteinyl disulfides. In such instances, auxiliary reagents, such as the hydrogen peroxide or di-tert-butyl ester of azodicarboxylic acid, can be used to facilitate disulfide bond formation.

Yet another class of sulfhydryl reactive groups form thio-ether bonds with sulfhydryl groups. Such groups include, inter alia, iodoacetamide, N-ethylmaleimide and other maleimides, including dextran maleimides, mono-bromo-bimane and related compounds, vinylsulfones, epoxides, derivatives of O-methyl-isourea, ethyleneimines, aziridines, and 4-(aminosulfonyl-)7-fluoro-2,1,3-benzoxadiazole.

Functional groups may be directly attached to the compound core, or they may be indirectly attached through a chain extender. Such chain extenders are well known in the art. See, for example, PCT WO 97/22371, which describes "linking groups" that would be suitable for use as chain extenders in the compositions of the present disclosure. Chain extenders are useful to avoid steric hindrance problems that are sometimes associated with the formation of direct linkages between molecules. Alternatively, chain extenders may be used to link several multifunctionally activated compounds together to make larger molecules. In a particularly preferred embodiment, the chain extender can also be used to alter the degradative properties of the compositions after administration and resultant gel formation. For example, chain extenders can be incorporated into one or both of the multifunctionally activated polymers to promote hydrolysis, to discourage hydrolysis, to promote oxidation and/or to provide a site for enzymatic degradation. Chain extenders can also activate or suppress activity of sulfhydryl and sulfhydryl-reactive groups. For example, for certain types of reactions, electron-withdrawing groups within one or two carbons of the sulfhydryl group would be expected to diminish its effectiveness in coupling, due to a lowering of nucleophilicity. Double-bond carbon and carbonyl carbon would be anticipated to have this effect. Bulky nearby groups for either partner are anticipated to diminish coupling rates, due to steric hindrance. Electron-withdrawing groups adjacent to the reactive carbonyl of glutaryl-N-hydroxy-succinimidyl would be anticipated to make this carbonyl carbon even more reactive with the sulfhydryl partner.

Chain extenders may provide sites for degradation, i.e., hydrolysable sites. Examples of hydrolysable chain extenders include, inter alia, alpha-hydroxy acids such as lactic acid and glycolic acid; poly(lactones) such as caprolactone, valerolactone, gamma butyl lactone and p-dioxanone; poly (amino acids); poly(anhydrides) such as glutarate and succinate; poly(orthoesters); poly(orthocarbonates) such as trimethylene carbonate; and poly(phosphoesters). Examples of non-degradable chain extenders include, inter alia, succinimide, propionic acid and carboxymethylate. See, for example, PCT WO 99/07417. Examples of enzymatically degradable chain extenders include Leu-Gly-Pro-Ala, which is degraded by collagenase; and Gly-Pro-Lys, which is degraded by plasmin.

In some embodiments, the sulfhydryl-reactive group (Y) is selected from the group consisting of esters (e.g., NHS-activated esters, such as N-hydroxy-succinimidyl esters), amides, and acid chlorides. In some embodiments, the sulfhydryl-reactive group is N-hydroxy-succinimidyl glutarate (also referred to herein as succinimidyl glutarate).

In some embodiments, the combination of activated polymers is as follows: the sulfhydryl-reactive group-containing compound, i.e., Compound$_1$-Y$_n$, is the tetrafunctional PEG, pentaerythritol poly(ethylene glycol) ether tetra-N-hydroxysuccinimidyl glutarate (10,000 g/mol) of Formula VI

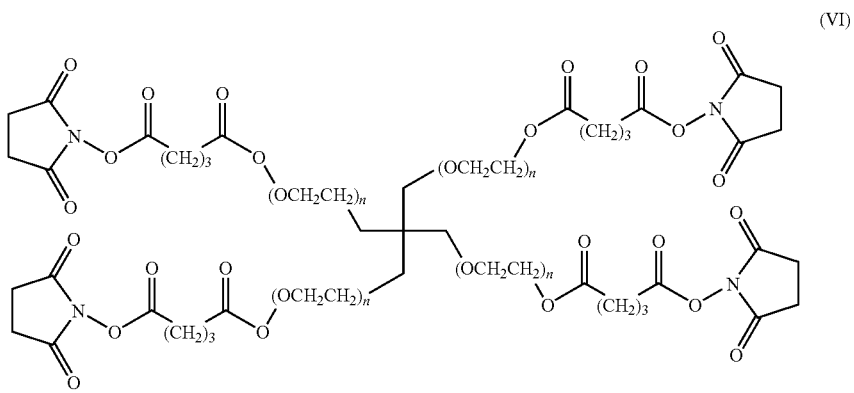

(VI)

and the sulfhydryl group-containing compound, i.e., Compound$_2$-(SH)$_m$, is the tetrafunctional PEG, pentaerythritol poly(ethylene glycol) ether tetra-sulfhydryl (10,000 g/mol) of Formula IV.3

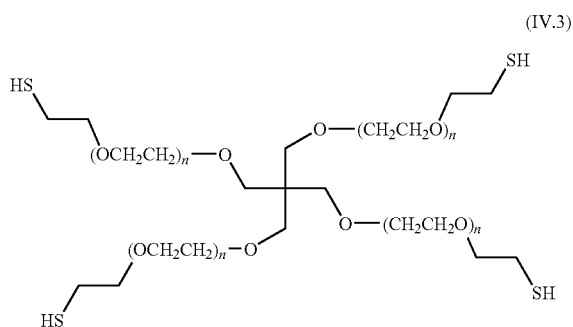

(IV.3)

In both cases, these "four-arm" PEGs are formed by ethoxylation of pentaerythritol, where each of the four chains is approximately 2,500 g/mol, and then derivatized to introduce the functional groups onto each of the four arms. Also preferred are analogous poly(ethylene glycol)-like compounds polymerized from di-glycerol instead of pentaerythritol.

Compounds of Formulae VI and IV.3 may be prepared to have differing levels of functional group substitution. The type and level of substitution may impact the gelation efficiency and gel time, final properties of the cross-linked matrix (e.g., gel strength and elastic properties of the hydrogel), cross-linking density (which also impacts swelling), and persistence of the gel in vivo. Further, the percentage substitution can affect the conditions required to achieve rapid cross-linking of the gel in use. For example, if the extent of NHS substitution is very low, the component will carry a higher percentage of uncapped carboxylic acid groups, thus potentially decreasing the pH of the aqueous cross-linking mixture. It is well known that the reaction of an NHS-capped material with a sulfhydryl group is best carried out at a relatively basic pH. A potentially detrimental effect of lowering the pH (e.g., below about pH 9) of the reaction mixture is that the rate of reaction between the thiol and NHS groups may be slower, thereby increasing gelation time. If the extent of NHS substitution is relatively low (e.g., below about 60%), it may become necessary to utilize buffers of higher pH (e.g., pH>10) to initiate reaction between the SH and NHS groups. Formulations for use as in situ forming hydrogels require that the pH be sufficiently high to facilitate rapid gelation, yet low enough to avoid hydrolysis of the hydrogel once cross-linked.

In certain embodiments, the extent of NHS substitution of compounds of Formula VI can range from about 40-100% (as measured by titration methods known to those in the art). In certain of these embodiments, the extent of NHS substitution of compounds of Formula VI can range from about 65% to about 100%, or about 75% to about 90% or about 65% to about 75%. In certain embodiments, the extent of NHS substitution of compounds of Formula VI can range from about 40-75%. In certain of these embodiments, the extent of NHS substitution of compounds of Formula VI can range from about 40-55%. In certain of these embodiments, the extent of NHS substitution of compounds of Formula VI can range from about 55-65%.

As noted above, variation in % SH substitution also may affect the overall network physical properties. Typically, the extent of SH substitution of compounds of Formula IV.3 can range from about 70-100%. The extent of SH substitution of compounds of Formulation II can be determined spectroscopically by the reaction of 5,5-dithiobis(2-nitrobenzoic acid) with a thiol functional group (SH) to form a highly colored anion which is measured by UV at 410 nm.

In certain preferred embodiments, the level of NHS substitution of compounds of Formula VI is about 70-90% and the level of SH substitution of compounds of Formula IV.3 is about 70-90%. In certain preferred embodiments, the level of NHS substitution of compounds of Formula VI is about 75-85% and the level of SH substitution of compounds of Formula IV.3 is about 75-85%. In one preferred embodiment, the level of NHS substitution of compounds of Formula VI is about 80% and the level of SH substitution of compounds of Formula IV.3 is about 80%

The compositions disclosed herein comprise at least two separate parts, or "components", which may be in liquid or solid form. The compositions disclosed herein typically comprise two separate components, which may be in liquid or solid form. In some embodiments, both components are liquids, such that each can be easily applied separately to the site of administration. One of the components may be in the form of a dry powder that becomes mixed with the second component, which is in a dry powder or a liquid form. The two components are sprayed separately onto the tissue, or by mixing at the tissue site. The components can be applied separately (simultaneously or sequentially) or may first be mixed together and then the mixture applied to the tissue site. It is also possible to have both components delivered to the site as powders, to be mixed with buffer at the site of administration.

The pH of the aqueous buffer solution that is used for each of the two (or more) composition components should be adjusted using routine optimization to achieve a final pH that is conducive to rapid gelation, without causing instantaneous gelation which interferes with the delivery process. The buffer solutions are aqueous and can be any pharmaceutically acceptable basic or acid composition. The term "buffer" is used in a general sense to refer to an acidic or basic aqueous solution, where the solution may or may not be functioning to provide a buffering effect (i.e., resistance to change in pH upon addition of acid or base) in the compositions of the present disclosure.

Low pH buffer solutions having a pH within the range of about 1.0 to 5.5, include by way of illustration and not limitation, solutions of: citric acid, hydrochloric acid, phosphoric acid, sulfuric acid, AMPSO (3-[(1,1-dimethyl-2-hydroxyethyl)amino]2-hydroxy-propane-sulfonic acid), acetic acid, lactic acid, and combinations thereof. In certain embodiments, the low pH buffer solution is a solution of citric acid, hydrochloric acid, phosphoric acid, sulfuric acid, and combinations thereof. An exemplary low pH buffer is a solution of hydrochloric acid, having a concentration of about 6.3 mM and a pH in the range of 2.1 to 2.3.

Regardless of the precise acidifying agent, the low pH buffer preferably has a pH such that it retards the reactivity of the nucleophilic groups on the first component. Low pH buffers can a pH of less than about 6.0. For example, an acidic buffer having a pH of 2.1 is generally sufficient to retard the nucleophilicity of thiol groups. A lower pH is typically preferred when the first component contains sulfhydryl groups as the nucleophilic groups. In general, the acidic buffer is an acidic solution that, when contacted with nucleophilic groups that are present as part of the first component, renders those nucleophilic groups relatively non-nucleophilic.

High pH buffer solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the buffer solution is a basic buffer solution of carbonate salts, phosphate salts, and combinations thereof.

In general, the high pH buffer is an aqueous solution that neutralizes the effect of the acidic buffer, when it is added to the homogeneous solution of the first and second components and the acid buffer, so that the nucleophilic groups of the first component regain their nucleophilic character (that has been masked by the action of the acidic buffer), thus allowing the nucleophilic groups to react with the electrophilic groups of the second component.

An exemplary high pH buffer is an aqueous solution of carbonate and phosphate salts. This buffer may be prepared by combining a base solution with a salt solution. The salt solution may be prepared by combining appropriate quantities of monobasic sodium phosphate monohydrate, sodium carbonate monohydrate, and sufficient water to provide a desired final solution volume. The basic buffer is typically prepared by adding the base solution as needed to the salt solution, ultimately to provide a mixture having the desired pH, e.g., a pH of 9.65 to 9.75.

In general, the basic species present in the high pH buffer should be sufficiently basic to neutralize the acidity provided by the acidic buffer, but should not be so nucleophilic itself that it will react substantially with the electrophilic groups of the second component. For this reason, relatively "soft" bases such as carbonate and phosphate are preferred in this embodiment of the disclosure. For example, certain types of reactions (e.g., nucleophilic substitution reactions) involving sulfhydryl PEG and amino PEG need a higher (e.g., basic) pH to enhance nucleophilicity.

To illustrate the preparation of an exemplary cross-linked matrix, the liquid components of the compositions disclosed herein may each be separately prepared by adding the activated synthetic polymer (in dry form or as a concentrated solution) to a liquid medium. Suitable liquid media include aqueous buffer solutions, such as monobasic sodium phosphate/dibasic sodium phosphate, sodium carbonate/sodium bicarbonate, glutamate or acetate, at a concentration of 0.5 to 300 mM. In general, the sulfhydryl-reactive PEG is prepared in water or a dilute buffer, with a pH of between around 2 to 6. In some embodiments, the sulfhydryl-reactive PEG is prepared in a pH 2.2 buffer. Buffers with pKs between about 8 to 10.5 for preparing the sulfhydryl-PEG component are useful to achieve fast gelation time of compositions containing mixtures of sulfhydryl-PEG and SG-PEG. These include carbonate, borate and AMPSO (3-[(1,1-dimethyl-2-hydroxyethyl)amino]2-hydroxy-propane-sulfonic acid). In contrast, using a combination of maleimidyl PEG and sulfhydryl-PEG, a pH of around 5 to 9 is preferred for the liquid medium used to prepare the sulfhydryl PEG.

In an alternative embodiment, both components can be mixed together in a single aqueous medium in which they are both unreactive, i.e. such as in a low pH buffer. Thereafter, they can be applied (e.g., sprayed) onto the tissue site along with a high pH buffer, after which they will rapidly react and form a gel.

In another exemplary method, one may combine an admixture of a first component (e.g., a polyethyleneglycol core with four nucleophilic thiol groups, such as pentaerythritol tetrakis [mercaptoethyl poly(oxyethylene) ether, also known as pentaerythritol poly(ethylene glycol) ether tetra-sulfhydryl] (4-arm PEG-SH) available from Aldrich Chemical Co. (Milwaukee, Wis.), and a second component (e.g., a polyethyleneglycol core with four electrophilic N-hydroxysuccinimide groups, such as pentaerythritol tetrakis [1-(1'-oxo-5-succinimidylpentanoate)-2-poly(oxyethylene)ether, also known as 4-arm PEG-N-hydroxy-succinimidyl glutarate ester] (4-arm PEG-NHS, 10,000 MW, available from Aldrich Chemical Co.), with a first, low pH, buffer (e.g., an acid solution, e.g., a dilute hydrochloric acid solution) to form a homogeneous solution. This homogeneous solution is mixed with a second, high pH, buffer (e.g., a basic solution, e.g., an aqueous solution containing phosphate and carbonate salts) whereupon the first and second components substantially immediately react with one another to form a cross-linked matrix. In certain embodiments, the gel is formed in less than one minute.

While some specific compounds and methods are discussed above, it is understood that the compositions and methods disclosed in any of the above-incorporated patents (U.S. Pat. Nos. 5,874,500, 6,051,648, 6,312,725, 6,458,889, 6,495,127, 6,624,245, 7,176,256, and U.S. 2005/0281883A1), whether specific or generic, are suitable to carry out the objects of the disclosure as disclosed herein.

In another aspect, disclosed herein is a hydrogel composition produced by a method comprising mixing a first compound, a second compound, and an analgesic, wherein the first compound is Compound$_1$-Y$_n$, as described herein, and the second compound is Compound$_2$-(SH)$_m$, as described herein. Compound$_1$-Y$_n$ and Compound$_2$-(SH)$_m$ may, for example, both be in the form of a dry powder. The combination of dry compounds is dissolved in an aqueous solution (e.g., an acidic buffer), and the solution is mixed with basic buffer to initiate cross-linking of the compounds. In some embodiments, the Compound$_1$-Y$_n$ is a compound of Formula VI. In certain embodiments, the Compound$_2$-(SH)$_m$ is a compound of Formula IV.3.

In yet another aspect, disclosed herein is a hydrogel composition produced by a method comprising mixing a first compound, a second compound, a third compound, and an analgesic, wherein the first compound is Compound$_1$-Y$_n$, as described herein, the second compound is Compound$_2$-(SH)$_m$, as described herein, and the third compound is a N-hydroxy-succinimidyl carbonate compound (e.g., a N-hydroxy-succinimidyl carbonate PEG compound of Formulae II.1, II.2 or II.3, also referred to as "SC-PEG"), as described herein. Compound$_1$-Y$_n$, Compound$_2$-(SH)$_m$, and the SC-PEG compound may, for example, all be in the form of dry powders. All three components may be in admixture. The combination of dry compounds is dissolved in an aqueous solution (e.g., a first, acidic buffer), and the solution is mixed with a second, basic buffer to initiate cross-linking of the compounds. The analgesic (e.g., bupivacaine in a particulate form) may be incorporated in the basic buffer, as described herein. In some embodiments, the Compound$_1$-Y$_n$ is a compound of Formula VI. In some embodiments, the Compound$_2$-(SH)$_m$ is a compound of Formula IV.3. In some embodiments, the SC-PEG compound is a 4-arm SC-PEG compound of Formula II.3. The addition of a 4-arm SC-PEG compound to formulations containing a mixture of Compound$_1$-Y$_n$, Compound$_2$-(SH)$_m$ can yield hydrogels that are capable of gelling rapidly and adhere well to tissue. The addition of an SC-PEG component can cause the hydrogel to degrade more slowly (e.g., 7-200 days from the time of application, depending on the proportion of SC-PEG included in the formulation) and, therefore, can last longer, i.e., decompose and degrade at a slower rate, than other similar hydrogel compositions. Further, the addition of a third SC-PEG component can produce hydrogel compositions which swell less than other similar hydrogel compositions.

In some embodiments, the compounds are mixed in a first solution prior to exposing them to cross-linking conditions. In some embodiments, the first solution is an aqueous solution. In some of these embodiments, the aqueous solution is acidic, which can optionally be buffered. In certain embodiments, the first solution comprises hydrochloric acid. Thus, in some of these embodiments, the first and second compounds are provided in dry, powder form and are then mixed in an aqueous solution, e.g., an acidic solution, to provide the first solution. The first solution, then, comprises both the first compound and the second compound. However, in these embodiments, the first solution does not provide the conditions for cross-linking to occur.

In some embodiments, the first solution comprising the compounds of the disclosure is mixed in with a second solution. In some embodiments, the second solution is an aqueous solution. In some of these embodiments, the second solution is basic, which can optionally be buffered. In certain embodiments, the second solution comprises monobasic sodium phosphate/sodium carbonate buffer at about pH 9-11. In other embodiments, the pH of the monobasic sodium phosphate/sodium carbonate buffer is about 9-10. In other embodiments, monobasic sodium phosphate/sodium carbonate buffer is about 10-11.

After cross-linking has occurred, a hydrogel is formed. Because the first solution is acidic, the final pH of the hydrogel is less than the pH of the second solution. In some embodiments, the final pH of the hydrogel is less than 9. The final pH of the hydrogel may be impacted by the extent of functional group substitution on the reaction components (in particular, the extent of NHS substitution).

In some embodiments, the first solution and the second solution are mixed by simultaneously administering (e.g., spraying) the first and the second solutions into the same space. Simultaneous administration of the two solutions facilitates efficient mixing and rapid gelation.

Spraying the solutions into the desired space has the effect of speeding the reaction time between Compound$_1$-Y$_n$ and Compound$_2$-(SH)$_m$. When a solution is sprayed, it is turned into aerosols, or small particles or droplets. The surface to volume ratio of the solution is thus increased greatly. Since most of the reaction between the two compounds takes place at the surface of the droplets, where the two compounds come into contact, increasing the surface to volume ratio greatly increases the incidents of contact between the two compounds and therefore increases the reaction rate.

In some embodiments, the first and the second solutions are mixed together immediately prior to the application of the mixture to the site of use, as described above.

As noted above, the hydrogel compositions described herein are biocompatible and, therefore, non-immunogenic and exhibit low levels of toxicity and/or antigenicity. In addition, the hydrogel compositions are biodegradable. Biodegradable segments and blocks may be either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, amide linkages, and the like. Larger biodegradable "blocks" will generally be composed of oligomeric or polymeric segments incorporated within the polymer core. Illustrative oligomeric and polymeric segments that are biodegradable include, by way of example, poly(amino acid) segments, poly(orthoester) segments, and the like. Biodegradable segments may be introduced into the polymer core by using a linker to couple the electrophilic or nucleophilic functional group to the polymer core. For example, a PEG core can be reacted with one or more glutarate molecules to introduce a biodegradable ester linkage into the reaction product.

Typically, the polymers described herein will be degraded in vivo over a period of days to months, depending on the nature of the bond formed by the cross-linking reaction. In vivo degradation of the hydrogels described herein can be affected by the extent of functional group substitution and the total amount of polymer (e.g., PEG) solids in the formulation. Certain cross-linked hydrogels (e.g., hydrogels formed form the reaction of compounds of Formula I and Formula II) begin to degrade fairly quickly in vivo and are substantially bioresorbed within about 1 month or less after administration to a tissue site, depending on the type of tissue and the physiological environment in the area of the tissue site. In some embodiments, the hydrogel may be substantially degraded within about 14 days. In certain embodiments, it can take between 7-14 days for the hydrogel to completely degrade.

As noted above, the cross-linked hydrogels formed as described herein contain interstitial space in which certain molecules can be trapped for later release. Therefore, the hydrogel compositions described herein are a useful and efficient manner for applying pharmaceuticals to a site of use in a slow-release, or time-release formulation.

In addition to the uses previously contemplated, the hydrogels described herein are particularly well-suited for controlled local delivery of analgesics and local anesthetics for the management of post-operative pain.

Thus, in another aspect, disclosed herein is a composition comprising a biocompatible hydrogel and an analgesic, where the biocompatible hydrogel is produced by a method comprising combining (e.g., mixing) a first solution comprising a first compound and a second solution comprising a second compound, where the first compound is $Compound_1$-$Y_n$, as described herein, and the second compound is $Compound_2$-$(SH)_m$, as described herein. In some embodiments, both the first and second compounds are combined into one solution. In some embodiments, $Compound_1$-$Y_n$ is the compound of Formula VI. In certain embodiments, $Compound_2$-$(SH)_m$ is the compound of Formula IV.3.

In yet another aspect, a composition is provided that includes a biocompatible hydrogel and an analgesic, where the biocompatible hydrogel is produced by a method that involves combining $Compound_1$-$Y_n$, as described herein, and $Compound_2$-$(SH)_m$, as described herein, wherein the compounds are each in a dry form. In some embodiments, $Compound_1$-$Y_n$ is the compound of Formula VI. In certain embodiments, $Compound_2$-$(SH)_m$ the of Formula IV.3. $Compound_1$-$Y_n$ and $Compound_2$-$(SH)_m$ may, for example, both be in the form of a dry powder. The combination of dry compounds is dissolved in an aqueous solution (e.g., an acidic buffer), and the solution is mixed with basic buffer to initiate cross-linking of the compounds.

In yet other embodiments, the analgesic is mixed in both the first and the second solutions prior to the mixing of the first and the second solutions. In still other embodiments, the analgesic is provided in a dry form and is mixed with the dry forms of the compounds of Formula VI and IV.3 before the first solution is prepared.

The analgesic may be contained in either of the first or the second solutions, depending on the stability, solubility, pKa, and/or reactivity or other properties of the compound in the solution(s). In some embodiments, the analgesic is mixed in the first solution (e.g., an acidic buffer) prior to the mixing of the first and the second solutions. In other embodiments, the analgesic is mixed in the second solution (e.g., basic buffer) prior to the mixing of the first and the second solutions. Depending on the form of the analgesic (e.g., free base or a salt), it may be beneficial to alter the type and pH of the basic (e.g., alkaline) buffer. For example, if a basic solution of a salt form of an analgesic (e.g., an analgesic that contains acid group(s), such as carboxylic) is combined with a mixture of reactive components as described herein in an acidic buffer, the pH of the combined solutions may be lower than if a free base is used. The lower pH may slow the rate of gelation of the hydrogel. Thus, it may be necessary to increase the pH of the basic buffer in order to still achieve rapid gelation of the hydrogel when a salt form of the analgesic is used.

Since sustained release of the analgesic may occur by a combination of degradation of the gel and dissolution of the drug particulates, analgesic release from the hydrogel also may be controlled by manipulating the composition of the gel itself (e.g., by selecting the composition of the individual reactive components, and/or functional group type and/or percentage of substitution of functional groups). Alternatively, or in addition, the gel composition may be altered by varying the molecular weight of the PEG components used. Alternatively, or in addition, the hydrogel composition may be altered by manipulating the concentration of reactive components used to form the hydrogel (i.e., solids content). For example, the concentration of total reactive components (e.g., PEG components) in the final, reaction mixture (i.e., the mixture formed by the addition of aqueous solutions and electrophilic and nucleophilic components) may be varied from about 5% to about 30%. In some embodiments, the combination of reactive components in the final reaction mixture may be varied from about 5% to about 10% (weight per volume of reaction mixture), or about 10% to about 15%, or about 15% to about 20%, or about 20% to about 30%. In one embodiment, the weight of combined reactive components in the final volume of hydrogel is about 5-15%. In one embodiment, the weight of combined reactive components in the final volume of hydrogel is about 10%. In one embodiment, the weight of combined reactive components in the final volume of hydrogel is about 15-25%. In one embodiment, the weight of combined reactive components in the final volume of hydrogel is about 20%.

Applicants have recognized that particularly effective sustained release formulations of certain analgesics can be produced by incorporating the analgesic in a particulate form into the hydrogels described herein. Accordingly, in some embodiments, the biocompatible hydrogel is loaded with an analgesic that is in a particulate form. In certain embodiments, the particulate analgesic may be substantially insoluble in the hydrogel. Hydrogels containing particulate analgesics can provide a significant advantage over standard solution-based post-surgery pain relief formulations in which an analgesic (e.g., bupivacaine dissolved in pH adjusted saline) is administered via a local infiltration procedure (e.g., subcutaneously or intrathecally). Saline-based formulations typically provide pain relief for a period of 4-6 hours. To assist in localizing the drug at the target site, saline-based bupivacaine-HCl formulations (e.g., MARCAINE available from Sterling Drug Inc., New York, N.Y.) are frequently co-administered with epinephrine. Incorporation of analgesic (e.g., bupivacaine) particulates in the present hydrogels can provide sustained release of an effective amount of the drug from the hydrogel for many days, thus extending the duration of pain relief for up to a week or more. The local analgesic delivery systems provided herein minimize systemic exposure and obviate the need for concomitant epinephrine treatment. Further, unintended intravascular injection associated with traditional systemic and local analgesic treatments may be minimized.

The term "effective amount" refers to the amount of composition required in order to obtain the effect desired. For example, a "pain relieving amount" or "pain treating amount" of a composition refers to the amount needed in order to relieve pain in a patient to a detectable degree. The actual amount that is determined to be an effective amount will vary depending on factors such as the size, condition, sex and age of the patient and can be more readily determined by the caregiver.

Hydrogels may be used to deliver analgesics to treat pain associated with a variety of medical procedures, including but not limited to, for example, hernia repair, vasovasotomy, appendectomy, arthroscopic procedures, laparoscopic procedures, myomectomys, cosmetic and wound procedures, and excision of masses and biopsies.

The extent of analgesic release from the hydrogel can be adjusted by manipulating the particle size and amount of drug in the hydrogel (i.e., concentration). The drug concentration also may vary depending on the method used to incorporate the drug into the hydrogel, as discussed below. In certain embodiments, the analgesic (e.g., bupivacaine) may be incorporated into the hydrogel at a concentration of about 1 mg/mL to about 500 mg/mL; or about 10 mg/mL to about 100 mg/mL. In certain embodiments, the concentration of analgesic may be about 1 mg/mL to about 10 mg/mL. In certain embodiments, the concentration of analgesic may be about 30 mg/mL to about 90 mg/mL. In certain embodiments, the concentration of analgesic may be about 40-60 mg/mL. In certain embodiments, concentration of analgesic is about 45-55 mg/mL. In certain embodiments, concentration of analgesic (e.g., bupivacaine) is about 50 mg/mL.

The total dose of drug also depends on the total volume of hydrogel delivered to the treatment site. In some embodiments, the total volume of gel delivered to the treatment site is about 5-15 mL. In some embodiments, the total volume of gel delivered to the treatment site is about 10 mL. Depending on the total volume delivered, the delivered dose of the analgesic may be about 200 to about 700 mg. In certain embodiments, the delivered dose is about 300 to about 600 mg. In certain embodiments, the delivered dose is about 400 to about 500 mg.

The particulates may take any shape and may have a cross-sectional diameter that ranges in size from micrometers to nanometers. The particulates may be homogenously sized or may have a distribution of sizes and may contain drug that is in solid form which can be a crystalline and/or amorphous state.

In some preferred embodiments, the analgesic is in a crystalline state. The crystalline form of the analgesic may contain one crystalline form or a combination of crystalline forms. The analgesic may exist as two or more crystalline phases (i.e., polymorphs), each phase having a different arrangement and/or conformation of molecules in the crystal lattice. A crystalline adduct, in contrast, may be formed if a certain amount of solvent is incorporated within the crystal lattice. If the solvent is water, the adduct may be referred to as a hydrate. The extent of crystallinity may be evaluated using standard analytical methods such as DSC (Differential Scanning Calorimetry) and XRD (X-ray diffraction).

Polymorphs and solvates of the analgesic can have different physical and chemical properties (e.g., melting point, chemical reactivity, solubility, optical properties, vapor pressure, and density). Further, differences in chemical and physical properties can impact the stability, dissolution, aqueous solubility, and bioavailability of the analgesic. For example, a solid compound may have a metastable crystalline structure that evolves over time in response to environmental and processing conditions. A solvate may desolvate in response to environmental and processing conditions, as well.

Phase conversion of some analgesics may occur during the manufacturing process. For example, milling or micronization processes may cause conversion of one polymorphic form into another polymorphic form.

The analgesic may be in an amorphous state. Amorphous solids consist of disordered arrangements of molecules and do not have a discernible crystal lattice structure. Amorphous forms of the analgesic may be prepared using various techniques known to those skilled in the art (including spray drying processes). Analgesics in an amorphous state may readily dissolve and dissipate from the hydrogels described herein under physiological conditions. Once dissolved, the analgesic is available for uptake by the tissue. Analgesics in a crystalline form may take longer to dissolve, making them relatively less bioavailable than if in an amorphous form. Although amorphous forms of the analgesic may be utilized with the hydrogels described herein, formulations containing amorphous dosage forms may be not be stable when stored for long periods of time (either as a powder or in solution). Lower solubility may be particularly valuable when extremely rapid dissolution of the analgesic is undesirable and/or when it is preferred to deliver the dissolved (i.e., bioavailable) form of the drug to the tissue over longer periods of time. Further, crystalline forms of the analgesic may be advantageously used when long-term stability is required, and certain crystalline polymorphs may be particularly stable and well-suited for use in the preparation of pharmaceutical formulations. Those of skill in the art can choose the proper form of the analgesic for the particular need and the particular degree of bioavailability desired.

In certain embodiments, hydrogel compositions are provided that include particulates having a mean particle size of less than one micrometer. In other embodiments, particulates range in size from about 500 nanometers to 5 micrometer. In other embodiments, particulates range in size from about 500 nanometers to 2 micrometers. In other embodiments, the particulates have a size of less than 500 nanometers; or less than 400 nanometers; or less than 300 nanometers; or less than 200 nanometers, or less than 100 nanometers; or less than 50 nanometers.

In certain embodiments, hydrogel compositions are provided that include particulates having a size of less than 5 micrometers. In other embodiments, particulates range in size from about 700 nanometers to 3 micrometer. In other embodiments, the particulates have a size of less than 2 micrometers; or less than 1.5 micrometer. In certain embodiments, the particulates have size of about 0.5 to about 1.5 micrometers or a mean particle size of about 1 micrometer.

Analgesic particles may be provided as a suspension in aqueous medium. A given suspension may utilize particles ranging in size from several nanometers to several micrometers and may contain particles having a narrow size distribution or a large distribution of sizes. Suspensions prepared using particles of similar size, however, may be more stable than those prepared using particles having a large distribution of sizes. Particles with a narrow particle size distribution typically are less prone to increase in size over time due to recrystallization. Particles having a size distribution that spans less than one order of magnitude (i.e., less than 10-fold distribution of sizes) may have similar dissolution rates in aqueous solutions and, therefore, can produce more stable suspensions. Suspensions prepared using a particles with a narrow distribution of sizes can remain as homogeneous dispersions (or can be easily re-suspended with agitation) for a period of many months and up to several years, making them particularly useful when long term shelf stability is required. In certain embodiments, suspensions remain stable for up to about 6 months, or up to about 1 year, or up to about 2 years.

The stability of the suspensions may be further improved by including a surfactant, suspending agent, and/or viscosity modifier into formulation (e.g., PLURONIC F127 (BASF), PLURONIC F68 (BASF), TWEEN (POLYSORBATE 80) (Spectrum Chemicals) poly(ethylene glycol) 3350 (Spectrum Chemicals), and/or hydroxypropyl methylcellulose (Spectrum Chemicals)).

In certain embodiments, combinations of surfactants or other additives may be used for producing suspensions of sub-micron or micron-sized particles that remain stabile for several months or more at room temperature. An exemplary combination of additives is PLURONIC F127 and PEG 3350 can be used to form suspensions of analgesic particles that remain stable for about one month.

Particulate analgesic may be formed in various manners. A method of preparing a hydrogel that contains a spontaneously precipitated analgesic is provided. In some embodiments, the analgesic (e.g., bupivacaine) is loaded into the gel by spontaneously precipitating the drug into the hydrogel as it is being formed. An analgesic (e.g., bupivacaine) is combined with electrophilic and nucleophilic components, as described herein in a low pH buffer (e.g., pH 2.2 HCl buffer). To this solution is added a high pH carbonate buffer (for example, pH ~9.5-11). The higher pH causes two different reactions to occur. First, a hydrogel is formed when the two component system, i.e., compounds of Formula I and compounds of Formula III, or Compound$_1$-Y$_n$ and Compound$_2$-(SH)$_m$, react. Second, the analgesic precipitates during the mixing. Thus, a hydrogel is formed containing a homogenous dispersion of precipitated analgesic in particulate form. Spontaneously precipitated formulations typically comprise particles of analgesic that range in size from about 1-50 microns, however spontaneously precipitated formulations containing particles sized outside of this range also may be formed using the methods described herein.

Hydrogels prepared by the described precipitation process can be loaded with analgesic (e.g., bupivacaine) in concentrations of up to about 30 mg/mL of final hydrogel volume, depending on the particular analgesic used. In one embodiment, the hydrogel contains analgesic in a concentration of up to about 20 mg/mL; or about 5 mg/mL to about 20 mg/mL of final hydrogel volume. In yet another embodiment, the analgesic concentration is about 10 mg/mL to about 15 mg/mL of final hydrogel volume.

In another exemplary method, particulate analgesic is combined as a suspension of particles into one or both of the hydrogel precursor components. A method of preparing a particulate analgesic involves combining an analgesic (e.g., bupivacaine or a salt thereof, such as bupivacaine-HCl) with a high pH (about 9.7) buffer and micronizing the analgesic using high-shear homogenization. Optionally, a surfactant, (e.g., PLURONIC F68 or F127 or TWEEN 20 or TWEEN 80, or a mixture thereof) may be used to improve the stability of the suspension (e.g., be minimizing settling and/or coagulation and/or agglomeration of the particles over time). A suspending agent and/or viscosity modifier (e.g., PEG or methylcellulose additives) also may optionally be included into the formulation to minimize sedimentation and/or caking of the particles. The pH of the micronized suspension is adjusted to about 9.3-9.7 (depending on which cross-linkable components will be combined with the nanosuspension), and the particle size is reduced via high pressure homogenization. High pressure homogenization can be used to reduce the size of the particles such that the cross-sectional diameter ranges from about 0.3 to about 3 microns.

Suspensions may be formed using either amorphous or crystalline forms of a particular analgesic or a mixture of amorphous and crystalline forms. Depending on the analgesic, homogenization may alter the morphology of the starting material. For example, an analgesic in a crystalline form may be transformed into an amorphous state or another crystalline form during the homogenization process.

Although suspensions may be formed using any amorphous or crystalline form of a particular analgesic, it may be preferable to utilize a relatively stable form (e.g., polymorph) to ensure that the morphology of the analgesic does not change during the homogenization process, during subsequent formation of the cross-linked hydrogel, and/or during storage of the final product.

In certain embodiments, the suspension contains bupivacaine in particulate form. Suspensions formed using bupivacaine as the starting material may utilize bupivacaine in a salt form (e.g., HCl) or bupivacaine in a free base form.

Incorporation of a salt form of an analgesic into the hydrogel may be achieved in different ways. The salt form of the analgesic may be added to the low pH component of the buffer system. In this case, the pH of the basic buffer component would have to be adjusted to ensure that the hydrogel will gel. Alternatively, the salt form may first be converted to the free base form and then suspended in the high pH component of the buffer system. In the case of certain analgesics, such as bupivicaine-HCl, the potential for generating a metastable polymorph of the drug may increase using this route. To improve stability, it may be preferable to prepare the suspension using a free base of bupivacaine that is synthetically prepared instead of by in situ precipitation with a basic buffer.

If a bupivacaine salt, such as bupivacaine-HCl is used as the starting material, the in-situ precipitated base material typically adopts a metastable, or transiently stable polymorphic form (Form II: T$_m$=97.6±0.2° C.), which may revert to a more stable polymorphic form (Form I: T$_m$=105.6±0.0° C.) over time. Given the transient nature of Form II, it may be preferable to utilize a more stable form of bupivacaine in a pharmaceutical formulation.

A more stable form of bupivacaine may be generated by using bupivacaine free base with melting point @ 105-107° C. (Form I) as the starting material. Use of an analgesic free base to prepare the nanosuspension also may avoid subsequent dilution with 5M NaOH, further simplifying the manufacturing process.

Suspensions prepared by the described process can be loaded to high levels with particulate analgesic due to the extremely small size (e.g., sub-micron) of the particles. For example, aqueous solutions can be prepared according to the processes described herein containing up to about 20% analgesic by weight. In certain embodiments, the analgesic may be loaded to about 18% by weight. In other embodiments, the analgesic (e.g., a crystalline form of bupivacaine free base) may be loaded to about 10-15% by weight. Higher loadings of analgesic may be achievable by using an appropriate surfactant, viscosity modifier, or combination thereof.

The suspension of analgesic particles may subsequently be combined with cross-linkable components and additional buffer(s) and/or other reagents. For example, the homogenized suspension is loaded into a first syringe. The contents of the first syringe are mixed with a low pH (pH 2.2 HCl buffer) solution of electrophilic (e.g., Compound$_1$-Y$_n$) and nucleophilic (e.g., Compound$_2$-(SH)$_m$) components, as described herein, housed in a second syringe to form a hydrogel containing a homogenous dispersion of particulate analgesic (also referred to herein as a "nanosuspension"). As noted above, hydrogels prepared by the described process can be loaded to high levels with particulate analgesic due to the extremely small size (e.g., sub-micron) of the particles. In one embodiment, the hydrogel contains analgesic in a concentration of greater than about 15 mg/mL of final hydrogel volume. In yet another embodiment, the analgesic concentration is about 20 mg/mL to about 70 mg/mL of final hydrogel volume. In yet another embodiment, the analgesic concentration is about 40 mg/mL to about 60 mg/mL of final hydrogel volume.

In the context of the present disclosure, an analgesic is a compound or a composition that reduces the pain in an individual. The term "analgesic" encompasses anesthetics as well. The analgesic used in the compositions and methods described herein can be an over-the-counter analgesic, such as a salicylate (e.g., acetylsalicylic acid), acetaminophen, and ibuprofen, or an opioid analgesic, such as codeine and morphine.

In some embodiments, the analgesic is a local anesthetic (i.e., an anesthetic intended for localized, rather than systemic, delivery at a treatment site). The analgesic may be a water-soluble or gel-soluble analgesic. Alternatively, the analgesic may be relatively lipophilic (e.g., lipid solubility of more than about 1). Lipophilic analgesics will not readily dissolve in the hydrogels described herein and will typically release from the hydrogel more slowly than would a gel/water soluble analgesic, depending on the polymer used to prepare the gel and its interaction with the analgesic.

Representative examples of anesthetics that may be combined with the hydrogel compositions described herein include those selected from the amino ester and amino amide classes of anesthetics.

The local anesthetic may be in an ionized or a non-ionized form. The proportion of ionized and non-ionized forms varies with the pH of the environment. As the non-ionized form is capable of diffusing across nerve membranes and blocking sodium channels, formulations having a larger amount of material in non-ionized form will typically have a faster onset of action. Conversely, a decrease in pH shifts equilibrium toward the ionized form, delaying onset of action.

Local anesthetics differ in respect to the pH at which the ionized and non-ionized forms are present at equilibrium. This pH is generally in the range of about 7.6-8.9. The onset of action may be more rapid when the equilibrium pH for a given anesthetic approximates the physiologic pH of tissues (i.e., 7.35-7.45).

The pKa can be expressed as the pH at which 50% of the molecules are free base and 50% of the molecules have a positive charge (i.e., ionized). Analgesics having $pK_a$'s below about 8.5 may be particularly compatible with certain hydrogel formulations, since such analgesics can suit the physicochemical properties of the gel under the conditions and pH's used to carry out cross-linking.

In certain embodiments, the anesthetic may be an amino amide local anesthetic. In certain embodiments, the analgesic is a local anesthetic (e.g., amino amide or amino ester anesthetic) having a $pK_a$ below about 8.5. Amino amide anesthetics contain an amide linkage between an aromatic nucleus and an amino, or piperidine group. In certain embodiments, the anesthetic is a member of the 1-alkyl-2',6'-pipecoloxylidide family of compounds. Representative examples of amino amide local anesthetics that may be combined with the hydrogel compositions described herein include, for example, bupivacaine, levobupivacaine, ropivacaine, lidocaine, mepivacaine, prilocaine, cinchocaine, etidocaine and articaine and salts and hydrates thereof. Further examples of amino amide local anesthetics that may be used with the described hydrogels include carticaine, trimecaine and salts and hydrates thereof.

In other embodiments, the local anesthetic may be an amino ester local anesthetic. The amino ester anesthetic may be an ester of aminobenzoic acid anesthetic. Although similar structurally to the amino amide local anesthetics, members of this class of anesthetics include an ester linkage rather than an amide linkage. Representative examples of amino ester local anesthetics that may be combined with the hydrogel compositions described herein include, for example, procaine, tetracaine and chloroprocaine. Further examples of amino ester type local anesthetics that may be used with the described hydrogels include amylocaine, benzocaine, butacaine, dimethocaine, meprylcaine, metabutozycaine, orthocaine, propoxycaine, procaine, proparacaine, and risocaine.

The choice of analgesic will depend on the intended use of the hydrogel and the properties (e.g., lipophilicity and $pK_a$) of the anesthetic. For example, if the intended use requires a potent form of the drug that readily crosses the cell membrane, it may be desirable to use a lipophilic amino amide compound, such as bupivacaine or a salt thereof. However, if a less potent form of analgesic is needed (e.g., to minimize toxicity), it may be preferable to use a less lipid soluble analgesic, such as Ropivacaine, or Mepivacaine or a salt thereof.

The local anesthetic may be in the form of a racemic mixture of enantiomers or may be a single enantiomeric form.

The local anesthetic may be in the form of an amorphous powder or may be in a crystalline form that includes one or more polymorphs of the anesthetic.

In certain embodiments, it may be preferable to combine the hydrogel composition with bupivacaine. "Bupivacaine", as used herein, refers to any form of bupivacaine, including free base, salt, hydrate, solvate, or enantiomer of bupivacaine. Bupivacaine (1-butyl-N-(2,6-dimethylphenyl)piperidine-2-carboxamide) may be in the form of a free base represented by the following chemical structure:

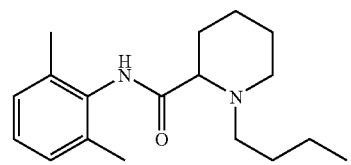 [SMILES: CCCCN1CCCCC1C(=O)Nc1c(C)cccc1C]

In certain embodiments, it may be preferable to combine the hydrogel composition with a salt of bupivacaine (i.e., bupivacaine-HCl). In one embodiment, the analgesic is 2-piperidinecarboxamide, 1-butyl-N-(2,6-dimethylphenyl)-monohydrochloride, monohydrate, represented by the following chemical structure:

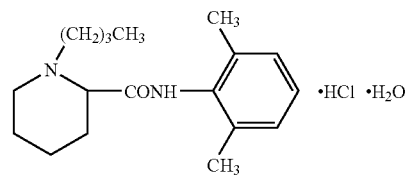

In certain embodiments, the hydrogel composition is combined with bupivacaine (e.g., bupivacaine free base, salt, hydrate, solvate, or enantiomer thereof) that is in a crystalline form. The crystalline form may a single polymorph or pseudopolymorph or a combination of polymorphs or pseudopolymorphs. In one embodiment, bupivacaine is in the polymorphic form (Form I). In another embodiment, bupivacaine is in the polymorphic form (Form II).

Bupivacaine has stereoisometric properties due to the presence of a chiral center in the molecule. Bupivacaine is available commercially as a racemic mixture of two isomers: levobupivacaine, L (−) isomer, and dextrobupivacaine D (+) isomer. A racemic mixture of bupivacaine may be used in the compositions described herein. Alternatively, it may be preferable to combine the hydrogel composition with a single enantiomer of bupivacaine, such as levobupivacine, an S(−)-enantiomer of bupivacaine, or a salt thereof (e.g., levobupivacaine hydrochloride). Although the pKa of levobupivacaine is 8.1, similar to the pKa of the racemic bupivacaine, levobupivacaine may be preferred in certain situations since this enantiomer may be associated with less vasodilation and cardiotoxicity and has a longer duration of action than racemic bupivacaine.

The compositions of the disclosure can also be packaged in kits and used in a variety of medical applications (e.g., in management of pain associated with hernia repair or breast augmentation procedures).

The described hydrogels may be applied directly to the tissue or may be introduced into a patient laparoscopically or arthroscopically, depending on the location of the treatment site. The components may be mixed using a dual syringe spray tip applicator well known to those skilled in the art.

However, in certain applications, it may be preferred to utilize an air-assisted spray tip to ensure that the acidic and basic components are efficiently mixed during application of the gel.

Kits are provided that include compositions and devices configured for use in various surgical settings. The kit would include buffer solutions, as well as written or otherwise illustrated instructions for use. In certain embodiments, a kit for use in medical applications (e.g., hernia repair or breast augmentation procedures), comprises: (a) a homogeneous dry powder composition comprised of: (i) a first component of Formula I, as described herein, and (ii) a second component that is a compound having the Formula III, as described herein, wherein the reactive groups are non-reactive in a dry environment but are rendered reactive upon exposure to an aqueous environment such that the components react in the aqueous environment to form a cross-linked matrix; (b) a first buffer solution having a pH within the range of about 1.0 to 5.5; (b) a second buffer solution having a pH within the range of about 9.0 to 11.0 that further comprises an analgesic (e.g., bupivacaine in a sub-micron or micron size particulate form); wherein each component is packaged separately and admixed immediately prior to use.

In other embodiments, a kit for use in medical applications, comprises: (a) a homogeneous dry powder composition comprised of: (i) a first component of formula $Compound_1\text{-}Y_n$, wherein Y is a sulfhydryl reactive group and wherein $n \geq 2$, and (ii) a second component that is a sulfhydryl group-containing compound having the formula $Compound_2\text{-}(SH)_m$, wherein $m \geq 2$; wherein the sulfhydryl and sulfhydryl-reactive groups are non-reactive in a dry environment but are rendered reactive upon exposure to an particular aqueous environment such that the components react in this particular aqueous environment to form a cross-linked matrix; (b) a first buffer solution having a pH within the range of about 1.0 to 5.5; (c) an analgesic (e.g., bupivacaine in a sub-micron or micron size particulate form); and (d) a second buffer solution having a pH within the range of about 6.0 to 11.0; wherein each component is packaged separately and admixed immediately prior to use. The analgesic can be added as a powder with the polymeric components or can be added in the first buffer solution (b).

Another exemplary kit would include buffer solutions, as well as written or otherwise illustrated instructions for use. A typical kit for use in medical applications (e.g., hernia repair or breast augmentation procedures), comprises: (a) a homogeneous dry powder composition comprised of: (i) a first component of formula $Compound_1\text{-}Y_n$, wherein Y is a sulfhydryl reactive group and wherein $n \geq 2$, and (ii) a second component that is a sulfhydryl group-containing compound having the formula $Compound_2\text{-}(SH)_m$, wherein $m \geq 2$; wherein the sulfhydryl and sulfhydryl-reactive groups are non-reactive in a dry environment but are rendered reactive upon exposure to an particular aqueous environment such that the components react in this particular aqueous environment to form a cross-linked matrix; (b) a first buffer solution having a pH within the range of about 1.0 to 5.5; and (c) a second buffer solution having a pH within the range of about 9.0 to 11.0 that further comprises an analgesic (e.g., bupivacaine in a sub-micron or micron size particulate form); wherein each component is packaged separately and admixed immediately prior to use.

In another embodiment, the kit can further comprise a delivery system that will allow the composition to be delivered as a gel or spray. The spray can be generated by manually mixing the components and passing them through a spray nozzle. The spray generation can also be accomplished by using a flow of gas (for example, air, nitrogen, carbon dioxide). Delivery devices that may be included in the kits will preferably be one of the multi-component syringe device and/or the pressurized delivery devices and devices adapted for laparoscopic delivery, such as those described in, for example, U.S. Patent Application Publication No. 2006/0071025 A1, incorporated herein by reference in its entirety.

In one embodiment of the kit, a multi-component syringe device is included in the kit. As previously described, the multi-component spray device may be a multiple-compartment syringe system having multiple barrels, a mixing head, and an exit orifice, wherein the dry powder composition, the first buffer containing analgesic, and the second buffer are housed separately in the multiple-compartment syringe system.

FIG. 1 of U.S. 2006/0071025 A1 shows an exemplary embodiment of the multi-compartment device. In an exemplary embodiment, when provided in a kit, the device is provided with three pouches. The first pouch is a liquid components pouch, which consists of two syringes that are pre-assembled into a housing. A transfer port closure is attached to the housing assembly to allow mixing of the dry powders into the correct syringe. A clip is attached to the plunger rod of the syringe that does not require mixing with the dry powders. The second pouch is a powder component pouch, which consists of a syringe containing the dry powder(s) and a desiccant package. The third pouch is an applicator pouch, which contains two applicators.

To use the kit, each pouch is opened using aseptic techniques and the contents of each pouch are transferred into a sterile field. In the sterile field, the liquid and powder components are prepared as follows. Without removing the syringe clip, the luer cap on the transfer port closure is removed. The cap is removed from the powder syringe and the powder syringe is connected to the opening of the transfer port closure. The liquid is transferred into the powder by forcefully depressing the plunger. The contents between the two syringes are mixed back and forth between the two syringes until the solid is completely dissolved (e.g., 18-20 times). The entire content is then pushed into the syringe contained in the syringe housing. The powder syringe is disengaged by detaching the transfer port closure by grasping the powder syringe barrel; pressing the levers on the syringe housing; and pulling both the empty powder syringe and transfer port closure from the housing. To expel all air from the syringe, the syringe tips are held up, the syringe plungers are leveled, the syringe clip is rotated to connect to the other plunger; and holding the syringe upright, all air is expelled from the syringe. As a final step, the applicator is snapped onto the end of the syringe housing making the composition ready to use. A gel containing a suspension of analgesic should be seen approximately three minutes following the mixing of the components.

Whether packaged together or separately, each of the components and the analgesic should be in sterile packages prior to use. Kits contemplated under the present disclosure are not limited to the devices described herein and may also include any other suitable delivery device known in the art of drug delivery.

The analgesic-containing hydrogels described herein can be used in a variety of medical and surgical situations. Exemplary medical applications involve delivery of analgesics to treat pain associated with various medical procedures, including but not limited to, for example, hernia repair, vasovasotomy, appendectomy, arthroscopic procedures, laparoscopic procedures, cosmetic procedures (e.g., breast augmentation), wound closure procedures, and excision of masses and biopsies.

Surgery is a common cause of acute pain. Following major surgical procedures, patients typically complain of pain at rest for two or three days. In some cases, the duration may be greater. Pain evoked by coughing, movement, and pressure is also present and may persist for a week or more after surgery and may continue until the healing process has progressed substantially. Hyperalgesia after surgery limits recovery and when poorly controlled, is associated with perioperative complications.

During these periods, a variety of different analgesics and pain killers may be administered to the patient. These analgesics are administered systemically and can result in adverse or unwanted side effects, such as dizziness, drowsiness, weakness, fatigue, nausea, constipation, and other adverse gastrointestinal effects. Opioids are routinely used for treating acute postoperative pain; however, dosage is limited by opioid side effects such as sedation, respiratory depression, nausea, and vomiting. Other than local anesthetics, few drugs are known to markedly reduce pain produced by coughing and movement after surgery. Local anesthetics also are desirable since the detrimental side effects associated with systemic treatments can be minimized or even eliminated. Unfortunately, the currently used local anesthetic treatments allow the anesthetic to quickly dissipate from the treatment site and such formulations typically offer relief from pain for several hours at most.

The hydrogels described herein can be used to slowly deliver local anesthetics or analgesics to the site of surgery or a wound, such that the pain at the site of the surgery or wound is reduced for a period of days, without generating a substantial systemic concentration of the analgesic in the patient. As discussed above, the hydrogel compositions described herein are well-suited for the slow-release application of pharmaceuticals, such as analgesics or local anesthetics, to a site of surgery. The analgesic-containing hydrogel is formed as described herein. When the hydrogel is formed and locally applied (e.g., to the tissue), the analgesic is slowly released to the tissue either by diffusion through the gel matrix and/or degradation of the hydrogel. For certain types of analgesics or local anesthetics (e.g., anesthetics which are hydrophilic at pH<8), as tissue fluids (e.g., plasma) infuse into the gel, the change in pH may cause the agent to become protonated, further increasing their solubility. For such agents, the agent may dissolve and diffuse out of the gel matrix at a rapid rate initially, leading to a "burst" effect. Additional drug also may be released during degradation of the gel to provide extended, sustained release.

In one embodiment, the described hydrogels may be used to reduce pain associated with hernia repair surgery. Herniorrhaphy, or hernia repair, is one of the most common surgical procedures performed by general surgeons, so a variety of methods have been developed for this procedure.

Hernias occur when a weakened abdominal muscle tears open, permitting the organs inside to push through. The most common is an inguinal hernia (75%) which occurs when a small portion of the bowel bulges out through the inguinal canal into the groin. The bulge usually contains tissue lining the inside of the abdomen as well as fatty tissue from inside the abdomen or a loop of intestine. The majority of hernias occur in males. Nearly 25% of men and 2% of women will develop inguinal hernias. Symptoms of an inguinal hernia may come on gradually or suddenly and may include a bulge in the groin or scrotum and discomfort, pain, or a feeling of heaviness. Other symptoms may develop if tissue in the hernia becomes trapped (incarcerated) or if the blood supply to the trapped tissue is cut off (strangulated). Mesh patches of synthetic material (GORE-TEX, TEFLON, DACRON, MARLEX, or PROLENE) are now being used to repair hernias. Patches are sewn over the weakened area in the abdominal wall after the hernia is pushed back into place. The patch decreases the tension on the weakened abdominal wall, reducing the risk that a hernia will recur. Nevertheless, a large number of herniorrhaphies performed are performed for recurrent hernias.

Inguinal hernias are a common medical condition and herniorrhaphy is a routine surgical procedure. Herniorrhaphies can be closed or opened procedures, with advantages and disadvantages for both. In both laparotomies and laparoscopic procedures a large closed space is formed, suitable for the infusion of an anesthetic-loaded gel, although special devices for application might be required.

Herniorrhaphies can be preformed using a laparotomy (open) or a laparoscopic (closed) procedure. In an open herniorrhaphy the doctor makes a single long incision over the hernia, removes the protruding sac (reduction) and sews the torn muscle close. A mesh patch is applied to the inside of the muscle wall to further strength it. An anesthetic gel, of a volume from 2-10 mL can be applied over the muscle wall, once it has been repaired, as there would be sufficient space between muscle layers, or between the muscle and the skin of the abdomen, to accommodate the material. After the muscle layers and the skin are sutured, the gel would remain in place. The anesthetic could easily diffuse from the surgical site itself, to affect the nerves in the area, thus providing extended pain relief. An open herniorrhaphy has several advantages in that it is a faster surgical procedure with less cost and can be done under local anesthetic. Its disadvantages are that is less favorable cosmetically, and is associated with greater pain, and hence longer hospitalization time.

The laparoscopic inguinal herniorrhaphy has several advantages over the open procedure. It requires approximately four small incisions instead of one large one with open surgery, so it is more favorable cosmetically, has a shorter hospitalization time and is usually associated with less pain. However it requires general anesthetic and a longer OR time and is riskier in patients with prior laparotomies. There are two main laparascopic techniques for hernia repair, the transabdominal preperitoneal (TAP) repair and the totally extraperitoneal (TEP) repair. In the TAP repair the surgeon inserts a trocar (hollow tube) and fills the abdomen (peritoneum) with carbon dioxide gas to allow visualization of the abdominal organs. The laparoscope, connected to a tiny video camera, is inserted to provide an up-close view of the patient's internal organs, which are displayed on a monitor. An incision is made in the peritoneal lining which covers the inside of the abdominal cavity, to permit dissection of the lining away from the abdominal wall to expose the defect. The repair mesh is rolled like a cigarette and is inserted through a trocar, and is sutured, tacked or stapled into place on the internal aspect of the muscle of the abdominal wall, under the peritoneal lining. The anesthetic-loaded gel could be applied at this point to cover the mesh and the surrounding muscle. The peritoneal lining is then pulled over the mesh and sutured closed, therefore keeping the anesthetic gel in place and permitting slow diffusion of the drug for effective pain relief.

The abdominal cavity is not entered in TEP procedure. Instead, a space is made between the peritoneal lining and the muscles of the abdominal wall. An incision is made just below the umbilicus and using a finger and blunt dissection the surgeon creates a tunnel and inserts a dilating trocar. The balloon of the dilating trocar is inflated forming a properitoneal space in which the site is visualized. The balloon is deflated and withdrawn and a structural trocar is inserted and carbon dioxide is infused to maintain the space, called a pneumo-pro-peritoneum. The hernia sac is reduced and the rolled surgical mesh is introduced into the properitoneal space and tacked into place. Once this is accomplished, an anesthetic-loaded gel could be applied into the properitoneal space prior to the removal of the structural trocar. As this is a closed space, once the incision is sutured, the gel would remain in place at the surgical site until degraded, providing extended pain relief.

In one aspect, a method of reducing post-surgical pain is provided that involves administering to a tissue at a site of surgery a biocompatible hydrogel, wherein the biocompatible hydrogel comprises an analgesic, and wherein the biocompatible hydrogel is produced by a method comprising mixing a first solution comprising a first compound and a second compound, wherein the first compound is a compound of Formula I, as described herein, and the second compound is compound of Formula III, as described herein, with a solution containing analgesic (e.g., bupivacaine in particulate form). In certain embodiments, the first solution is prepared by addition of an aqueous solution to a homogenous mixture of the first and second compounds, where these compounds are in a dry powder form. In one embodiment, the described method is utilized in conjunction with a hernia repair surgery. In another embodiment, the described method is utilized in conjunction with a breast augmentation surgery. In some embodiments, the hydrogel is administered before the skin covering the tissue is apposed and sutured. In other embodiments, the hydrogel is administered after the surgical incision has been sutured.

In another aspect, a method of reducing post-surgical pain is provided that involves administering to a tissue at a site of surgery a biocompatible hydrogel, wherein the biocompatible hydrogel comprises an analgesic, and wherein the biocompatible hydrogel is produced by a method comprising mixing a first solution comprising a first compound and a second compound, wherein the first compound is Compound$_1$-Y$_n$, as described herein, and the second compound is Compound$_2$-(SH)$_m$, as described herein with a solution containing analgesic (e.g., bupivacaine in particulate form). In some embodiments, Compound$_1$-Y$_n$ is the compound of Formula VI. In certain embodiments, Compound$_2$-(SH)$_m$ the of Formula IV.3. In certain embodiments, the first solution is prepared by addition of an aqueous solution to a homogenous mixture of the first and second compounds, where these compounds are in a dry powder form. In one embodiment, the described method is utilized in conjunction with a hernia repair surgery. In another embodiment, the described method is utilized in conjunction with a breast augmentation surgery. In some embodiments, the hydrogel is administered before the skin covering the tissue is apposed and sutured. In other embodiments, the hydrogel is administered after the surgical incision has been sutured.

In a further aspect, disclosed herein is a method of sealing a wound comprising administering to the wound a biocompatible hydrogel comprising an analgesic, wherein the biocompatible hydrogel is produced by a method comprising mixing a first solution comprising a first compound and a second solution comprising a second compound, wherein the first compound is a compound of Formula I, as described herein, and the second compound is a compound of Formula III, as described herein. In some embodiments, the compound of Formula I is a compound of Formula II. In certain embodiments, the compound of Formula III is a compound of Formula IV.

In yet another aspect, the hydrogels disclosed herein may be used in a method of sealing a wound comprising administering to the wound a biocompatible hydrogel comprising an analgesic, wherein the biocompatible hydrogel is produced by a method comprising mixing a first solution comprising a first compound and a second compound, wherein the first compound is Compound$_1$-Y$_n$, as described herein, and the second compound is Compound$_2$-(SH)$_m$, as described herein with a solution containing analgesic (e.g., bupivacaine in particulate form). In some embodiments, Compound$_1$-Y$_n$ is the compound of Formula VI. In certain embodiments, Compound$_2$-(SH)$_m$ the of Formula IV.3. In certain embodiments, the first solution is prepared by addition of an aqueous solution to a homogenous mixture of the first and second compounds, where these compounds are in a dry powder form.

The analgesic-containing hydrogels described herein can be applied to an internal, e.g., subcutaneous, site of surgery to provide a time-release form of analgesic or anesthetic until the internal site heals. The hydrogels can also be applied to a cutaneous injury to seal the wound while providing analgesic or anesthetic benefit. In some of these embodiments, the hydrogel is administered after the wound has been sutured. In other embodiments, the hydrogel is administered before the wound has been sutured. In some embodiments, the wound is a surgically-induced wound. In other embodiments, the wound is caused by an external trauma. Further, the analgesic-containing hydrogels can be used to prevent surgically-induced tissue adhesion.

EXAMPLES

The following examples are representative of several aspects of the disclosure disclosed herein, and are not intended to limit the scope of what the inventors regard as their disclosure.

Throughout these examples, and throughout the specification, the term "4-armPEG" refers to the following structure

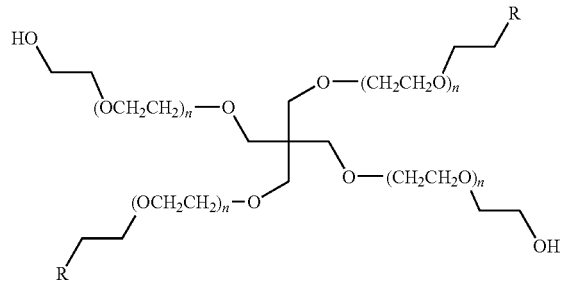

or the following structure

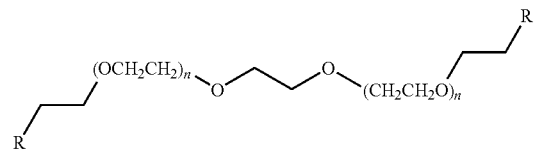

Throughout these examples, and throughout the specification, the term "4-armPEG" refers to the following structure

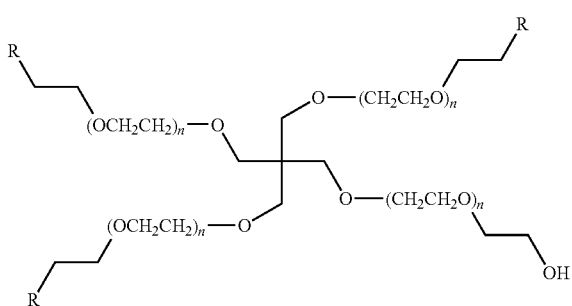

Throughout these examples, and throughout the specification, the term "4-armPEG" refers to the following structure

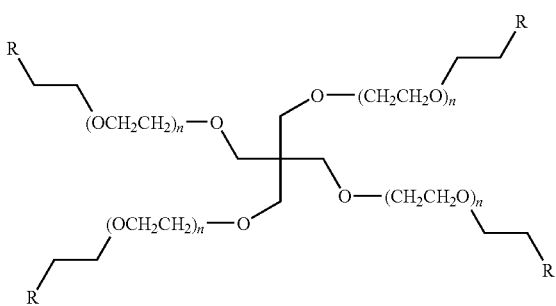

The following compound names are defined as follows:

"4-armPEG-OH" is a 4-armPEG where the two R groups are OH. Alternatively, "4-armPEG-OH" is a compound of Formula I, where $R_1$ is hydrogen.

"4-armPEG-OH" is a 4-armPEG where all three R groups are OH. Alternatively, "4-armPEG-OH" is a compound of Formula I.1, where $R_1$ is hydrogen.

"4-armPEG-OH" is a 4-armPEG where all four R groups are OH. Alternatively, "4-armPEG-OH" is a compound of Formula I.2, where $R_1$ is hydrogen.

"4-armPEG-SC," also referred to as "4-armPEG succinimidyl carbonate," is a compound of Formula II.1.

"4-armPEG-SC," also referred to as "4-armPEG succinimidyl carbonate," is a compound of Formula II.2.

"4-armPEG-SC," also referred to as "4-armPEG succinimidyl carbonate," is a compound of Formula II.3.

"4-armPEG-SH," also referred to as "4-armPEG sulfhydryl," is a compound of Formula IV.1.

"4-armPEG-SH," also referred to as "4-armPEG sulfhydryl," is a compound of Formula IV.2.

"4-armPEG-SH," also referred to as "4-armPEG sulfhydryl," is a compound of Formula IV.3.

Example 1

Synthesis of 4-ArmPEG Succinimidyl Carbonate

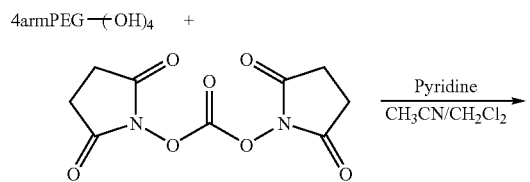

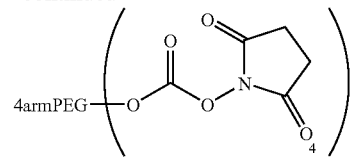

To 1.54 g (6.0 mmol) N,N'-disuccinimidyl carbonate (DSC) in 40 mL anhydrous acetonitrile was added 5 g of dry 4-armPEG-OH (2 mmol —OH group) (MW=~10 kg/mol) in 10 mL dry $CH_2Cl_2$. To the mixture 0.5 mL of dry pyridine was added. 4-(dimethylamino)pyridine (DMAP) may optionally be added to increase the rate of reaction. The reaction mixture was stirred at room temperature overnight under argon. The reaction mixture was then concentrated on a rotary evaporator, and the crude product was precipitated from diethyl ether. The resulting white solid was suspended in 15 mL of dichloromethane, and was subsequently filtered to obtain a clear solution. The clear solution was further diluted with 10 mL acetonitrile anhydrous. A white solid was then precipitated in 375 mL diethyl ether, and filtered through a filter paper. The solid was further purified by dissolution in 15 mL dry acetonitrile and precipitation in 225 mL diethyl ether three times. The final yield was about 45-75%. The purity of final product was confirmed by $^1H$ NMR. The degree of substitution was around 70-80% measured by NHS (N-hydroxysuccinimide) titration methods.

Example 2

Synthesis of 2-ArmPEG Succinimidyl Carbonate 10 g dry 4-armPEG (MW 8 kDal) in 20 mL dry $CH_2Cl_2$ was added into 2.56 g DSC in 40 mL anhydrous acetonitrile, followed by adding 1 mL dry pyridine and 100 mg of 4-(dimethylamino)pyridine (DMAP). The reaction mixture was stirred at room temperature for overnight under argon. Then the reaction mixture was concentrated on a rotary evaporator, and the crude product precipitated from diethyl ether. The white solid was then dissolve in 20 ml acetonitrile, and precipitated in 300-400 mL diethyl ether (repeat 3-5 more times). Filtrate to get white solid. The final yield was around 60-80%. The purity of final product was monitored by $^1H$-NMR. The degree of substitution was around ~80% measured by NHS titration method.

Example 3

Synthesis of 3-ArmPEG Succinimidyl Carbonate 10 g dry 3-armPEG (MW 10 kDal) in 20 mL dry $CH_2Cl_2$ was added into 2.31 g DSC in 40 mL anhydrous acetonitrile, followed by adding 1 mL dry pyridine and 100 mg of DMAP. The reaction mixture was stirred at room temperature for overnight under argon. Then the reaction mixture was concentrated on a rotary evaporator, and the crude product precipitated from diethyl ether. The white solid was then dissolve in 20 mL acetonitrile, and precipitated in 300-400 mL diethyl ether (repeat 3-5 more times). Filtrate to get white solid. The final yield was around 60-80%. The purity of final product was monitored by $^1$H-NMR. The degree of substitution was around ~80% measured by NHS titration method.

Example 4

Preparation of Hydrogel 1 ("TC gel")

To a 1 mL syringe 25-100 mg of 4-armPEG sulfhydryl (4-armPEG-SH) were added and mixed with 0.5 mL of pH 9.6 buffer. To another 1 mL syringe 25-100 mg of 4-armPEG succinimidyl carbonate (4-armPEG-SC) were added and mixed with 0.5 mL of 6.3 mM HCl solution. Both solutions were sprayed into a 20 mL scintillation vial through a Micromedics 5 cc Aerosol Applicator (Ref. SA-6105) under compressed $CO_2$ at 10 psi to form a gel.

The reaction was performed five times, each time varying the percentage of the two 4-armPEG reactants. The time, in seconds, it took for the gel to form and the gel aspect in air was recorded each time. The results are shown in Table 1, below.

Example 5

Preparation of Hydrogel 2

To a 1 mL syringe 25-100 mg of 4-armPEG sulfhydryl (4-armPEG-SH) were added and mixed with 0.5 mL of pH 9.6 buffer. To another 1 mL syringe 80-160 mg of 2-armPEG succinimidyl carbonate (2-armPEG-SC) were added and mixed with 0.5 mL of 6.3 mM HCl solution. Both solutions were sprayed into a 20 mL scintillation vial through a Micromedics blending Applicator (Ref. SA-3673).

The reaction was performed three times, each time varying the percentage of the two PEG reactants. The time, in seconds, it took for the gel to form, swelling ratio and degradation time were recorded. The results are shown in Table 2, below.

Example 6

Hydrogel Degradation Test 0.5 g of hydrogel, prepared by the procedure of Example 4 or Example 5, was immersed into 20 mL of PBS buffer and incubated at 37° C. in an air forced oven. The time, in days, it took for the gel to dissolve was recorded. The results are shown in Table 1 and Table 2, below.

Example 7

Hydrogel Swelling Test

The weight of about 2 g of hydrogel, prepared by the procedure of Example 4 or Example 5, was recorded. The hydrogel was then immersed into 20 mL of PBS buffer and incubated for 24 hours at 37° C. in an air forced oven. The gel was then dried with paper towel and weighed. Swelling percent was calculated based on the following formula:

$$\text{Swelling \%} = (W_t - W_0)/W_0 \times 100$$

where:

$W_0$ is the pre-incubation weight of the hydrogel; and $W_t$ is the post-incubation weight of the hydrogel.

The results are shown in Table 1 and Table 2, below.

TABLE 1

| 4-armPEG-SC (%) | 4-armPEG-SH (%) | Gel Time (sec) | Gel Aspect in Air | Swelling (%) | Degradation (days) |
| --- | --- | --- | --- | --- | --- |
| 2.5 | 2.5 | <30 | clear, firm | 27 | 16 |
| 3 | 3 | <30 | clear, firm | N/A | 20 |
| 3.75 | 3.75 | <30 | clear, firm | N/A | 75 |
| 5 | 5 | instant | clear, firm | 60 | 132 |
| 10 | 10 | instant | clear, firm | 120 | 210 |

TABLE 2

| 4-armPEG-SC (%) | MW g/mol | 4-armPEG-SH (%) | MW g/mol | Gel Time (sec) | Swelling (%) | Degradation (days) |
| --- | --- | --- | --- | --- | --- | --- |
| 2.5 | 10,000 | 10 | 20,000 | 120-180 | N/A | 4 |
| 10 | 10,000 | 16 | 8,000 | 10 | 390 | >30 |
| 5 | 10,000 | 8 | 8,000 | 20 | 280 | 30 |

Example 8

Swell Force Test 4-armPEG sulfhydryl was weighed into a 1 mL syringe and mixed with 1 mL of pH 9.6 buffer. 4-armPEG succinimidyl carbonate was weighed into another 1 mL syringe and mixed with 1 mL of 6.3 mM HCl solution. Both solutions were sprayed into a 2 mL test container through a Micromedics 5 cc Aerosol Applicator under compressed $CO_2$. The formed gel in the test container was put onto a Test Resources Electromechanical Test System for swell force test.

Figure 2:
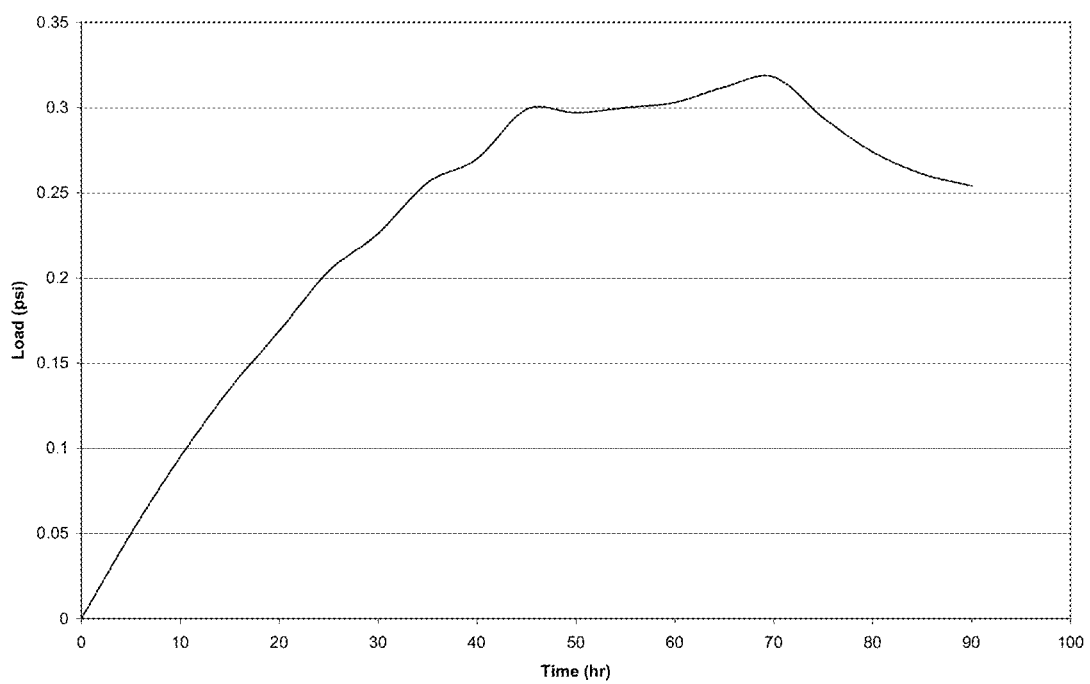
FIG. 2 is a graph showing the results of the swell force conducted on a gel having 5% 4-armPEG-SC and 5% 4-armPEG-SH.

The test was first conducted with a gel formed having 2.5% 4-armPEG-SC and 2.5% 4-armPEG-SH. The test was then repeated with a gel formed having 5% 4-armPEG-SC and 5% 4-armPEG-SH. The results are shown in FIGS. 1 and 2. The low pressure produced by swelling allows the gel to be applied safely into a confined area such as spinal cord.

Example 9

Biocompatibility Testing for the Polymer

The hydrogel may be in prolonged contact (24 hours to 30 days) with tissue. Therefore, the following biological effects are evaluated: cytotoxicity, sensitization, genotoxicity, and implantation.

Preparation of Extracts

Extraction is performed using both polar and non-polar solvents. The most commonly used extraction media are physiological saline, vegetable oil, dimethylsulfoxide, and ethanol. Other extraction media such as polyethylene glycol or aqueous dilutions of ethanol can be selected. For in vitro cytotoxicity testing, complete cell-culture medium is most often employed.

A weight-to-volume ratio (4 g per 20-mL extraction vehicle) is utilized for extraction at a specific temperature and period of time if the surface area of the device or material cannot be determined. A common extraction procedure is to incubate the test device or material at 37° C. for 24 hours.

Exaggerated extraction may be useful for hazard identification (e.g., 50, 70 or 121° C. for 72, 24 or 1 h, respectively). However, extraction conditions are chosen so as not to initiate significant degradation of the material. Samples are exposed to the planned sterilization procedure prior to extraction.

Cytotoxicity

Three main types of cell-culture assays have been developed: the elution test, the direct-contact test, and the agar diffusion test. In the elution test, an extract (eluate) of the material is prepared and added in varied concentrations to the cell cultures. Growth inhibition is a widely used parameter, but others may also be used. In the direct-contact test, pieces of test material are placed directly on top of the cell layer, which is covered only by a layer of liquid cell-culture medium. Toxic substances leaching from the test material may depress the growth rate of the cells or damage them in various ways. In the agar diffusion test, a piece of test material is placed on an agar layer covering a confluent monolayer of cells. Toxic substances leaching from the material diffuse through the thin agar layer and kill or disrupt adjacent cells in the monolayer. After the tests are conducted, the extent of the cytotoxicity of the material is determined.

Sensitization

One of the most recognized and validated assays is the guinea pig maximization test (GPMT). A test design very similar to the GPMT is widely used for assessing the sensitizing potential of medical devices (ASTM F720). After a challenge period, the skin reactions are graded on a ranking scale according to the degree of erythema and edema.

Genotoxicity

Several tests are available to assess genotoxic potential, since no single test can detect all types of mutagens. The Ames reverse mutation, chromosomal aberration and mouse lymphoma forward mutation tests are all common. After the tests are conducted, the results are noted.

Implantation

Tissue response after implantation in relevant tissue in rats is graded for up to 7 days and the results are noted.

Additional Tests

Testing for Delay of or Prevention of Healing—Inflammation and the replacement of soft tissue with fibrous tissue is an expected outcome of the normal healing process. Reducing the formation of adhesions may also delay or prevent healing. This is tested in animal studies. Adhesion barriers placed at suture lines or at anastomotic sites are tested and are determined not to reduce tissue-holding strength after suture removal.

Infectivity Testing—The enhancement of sepsis following challenge with a bacterial inoculums is tested. This test determines whether the hydrogel causes infection by, for example, the stimulation of bacterial growth, the inhibition of antibiotic diffusion to the infection site, a device-related increase in the entrance of infecting organisms into the systemic circulation from the surgical site, or unknown mechanisms. The animals are challenged with a mixture of gut organisms in the presence and absence of the adhesion barrier, and mortality and abscess formation are scored. Studies are conducted with the appropriate sample size and design so as to be statistically valid.

Example 10

In Vivo Biocompatibility Model

To determine the in vivo biocompatibility of the hydrogel produced by the methods described herein, the following animal protocol is used. In this model two 2-cm incisions are made over the dorsal midline, at the level of the scapulae and the sacrum, to expose the right and left cervical trapezius and gluteal muscles, respectively. An incision is made in the muscle, near its origin on the vertebral column and then blunt dissection is used to form a tunnel, approximately 1 cm long, through the muscle. The hydrogel (approximately 250 µL) is administered by placing the end of the delivery catheter at the distal end of the tunnel. The tunnel is sutured closed, and then the contralateral muscle is treated in the same manner. Once the right and left muscles have been treated, the incision is closed. The same procedure is followed for both cervical trapezius and gluteal muscles, thus allowing four sites for evaluation in each rat.

Two, four and eight weeks later at least 3 rats are sacrificed, and the 4 muscles excised and place in formalin for histological processing. Each slide will be evaluated for inflammation, edema and necrosis using a standard histopathology rating system.

Example 11

Protocol for Surgical Adhesion Study

This example is a protocol for determining the efficacy of hydrogels on the inhibition of adhesions using the cecal-sidewall model for surgical adhesion disease in the rat.

Surgical Procedure

Animals will be weighed and anesthetized with isoflurane gas. The abdomen will be shaved and cleaned with a skin-antibacterial cleanser and wiped with a chlorohexane soaked gauze. An antibiotic, 40,000 IU/kg of depo-penicillin will be injected into the right thigh and an analgesic, 0.01 mg/kg of buprenorphine, into the left thigh. A 4 cm incision will be made in the skin beginning approximately 2 cm caudal to the linea alba. The cecum will be located, exteriorized and the ventral and dorsal surfaces abraded by stroking with a number 10 scalpel at a 45 degree angle relative to the cecal surface until the presence of petechial hemorrhage is observed. The scraped cecum will be wrapped in saline-soaked gauze. Blunt-nosed forceps will be used to separate the peritoneal wall from the skin and the peritoneal wall inverted using small doynes to expose the inside of the wall. A rectangular cut approximately 1.2×1.8 cm will be made by shallow incisions to the peritoneal wall. The top membrane and a layer of muscle tissue will be removed using forceps. The lateral aspect of the cacum will be sutured to the lateral edge of the abraded rectangle using two stitches, one at each lower corner. After injury, the rats will be randomly assigned to the treatment or control groups. For the treatment group approximately 250 mL of COSEAL or a hydrogel, as described herein, will be placed between the abraded site and the cecum and the two remaining sutures placed at the medial corners to contain the gel between the cecum and the abraded sidewall.

The control group will consist of sham-operated rats which will be subjected to the same surgical procedure, but without application of a gel to the abraded site. The exposed organ will be replaced in the abdomen in such a manner as to prevent torsional stress on the intestines. The musculoperitoneal layer will be closed with 5-0 Polysorb sutures and the skin with 3-0 Polysorb (Ethicon) sutures. A collar will be placed around the neck of the animal to prevent subject interference with the stitches, and the rat will be placed in a clean cage and warmed with a heating lamp until consciousness is regained. The rats will be weighed on a daily basis until sacrificed.

Evaluation of Adhesions

Seven days after surgery the rats will be euthanized and the same evaluator who will be unaware of group assignment will score all adhesions. Prior to sacrifice the incision site will be visually checked for signs of inflammation or lack of wound healing. A cardiac puncture will be preformed to obtain blood for later analytic studies. Then the rats will be sacrificed using $CO_2$ asphyxiation and re-opened along the midline. The internal organs will be visually checked for abnormalities. The peritoneal wall will be inverted and adhesions between the four stitching points at the corners of the cecum (perimeter adhesions) will be assessed for strength according to a pre-defined scoring system. The perimeter adhesion strength will be scored as 0, no adhesions; 1, adhesions separable by blunt dissection; 2, adhesions not easily separable; and 3, dense adhesions with unavoidable tearing of tissue. A final value for the perimeter adhesions for each individual animal will be obtained by taking the mean of the adhesion strength of the four sides. The sutures will then be cut and the adhesions between the cecum and the sidewall will be assessed. In addition to strength, using the same scale as for the perimeter adhesions, the extent of cecal-sidewall adhesion formation will be quantified by dividing the area of the peritoneal defect into four areas, each 25% of the total area, and assigning a value according to the following scale: 0, no adhesions; 1, 1-25% of area; 2, 26-50% of area; 3, 51-75% of area; and 4, 76-100% of area covered. A final adhesion score for the cecal sidewall area will then be calculated by multiplying the strength of the adhesion by the value determined by the extent of the area. Statistical analysis will be performed using a Student's t-test analysis between each pair of groups. In all cases a p value<0.05 will be considered statistically significant.

Example 12

Evaluation of a Surgical Sealant by Application to the Rabbit Carotid Artery

In this study the safety and effectiveness of a surgical sealant are evaluated in vivo. This study is designed to assess the host response to application of the material in a carotid artery defect, as well as to assess the ability of the material to seal the site to prevent blood loss.

Surgery. A total of 24 New Zealand White rabbits weighing between 2.5 and 3.0 kg are used in this study. The rabbits are assigned to two groups; a treatment group using the sealant and a control (tamponade) group. The animals are anesthetized with a ketamine/Xylazine cocktail and maintained by inhalation of isofluorane. Immediately prior to surgery the rabbits are anticoagulated with an intravenous injection of 200 U/kg of heparin. The animals are prepared for surgery, and the right carotid artery is exposed through a lengthwise incision in the neck region. The surrounding tissue and adventitia were dissected free from the carotid artery. The carotid artery is clamped using atraumatic vascular clamps. A puncture hole is made in the artery using a 27 gauge hypodermic needle. The vessel is wiped cleaned with sterile saline soaked gauze and in the sealant group, the material is applied to the defect using a two component delivery device.

After the material is set for 30 seconds, the clamps are removed. The tamponade control group is treated similarly, except as noted. Bleeding is controlled in the tamponade control group by holding gauze over the defect with pressure, but no material is applied. The vessel remains clamped for the 30 second set time in the control animals for consistency.

The amount of blood lost and the time when blood flow stop are recorded. Blood loss is measured by using pre-weighted dry gauze to absorb leaking blood. The amount of material applied to the defect in the treatment group is also recorded. Once hemostasis is achieved, two sutures are placed around the vessel, at each end of the site and anchored to the fascia to help locate the area for histological removal. The fascia and skin are sutured closed. Animals are allowed to recover and observed daily for signs of distress, pain and health. The incision line is inspected daily for signs of dehiscence and bleeding.

Necropsy. Seven days post-operative one-half of the animals (n=12) are euthanised and necropsy is performed. The sites are observed grossly, and all observations including color, swelling, healing, hematoma formation, local collection of fluids, necrosis, and the presence or absence of lesions are also recorded. Two weeks post-operative the remaining animals are evaluated in the same manner.

Histology. The implants are surrounding tissue are fixed in 10% neutral buffered formalin and processed for histological evaluation. Once removed, a suture is placed at the distal end of the vessel to help maintain orientation. The samples are embedded in paraffin and stained with hematoxylin and eosin after sectioning. Histological evaluation includes fibrosis, necrosis, and inflammation at the surgical site. The presence of residual material was noted, as were any changes in surrounding tissue morphology, such as calcification.

Example 13

Bupivacaine-Loaded Hydrogel (In Situ Precipitate)

Bupivacaine-HCl, a compound selected from the group consisting of Formula II.1, Formula II.2, Formula II.3, and Formula VI, and a compound selected from the group consisting of Formula IV.1, Formula IV.2, Formula IV.3, Formula IV.4 and Formula IV.5 are dissolved in a pH 2.2 buffer up to a maximum of about 30 mg/mL. The solution is combined with an equal volume of carbonate buffer (pH 10.5-11.0) (e.g., using a dual compartment gel spray kit) to form a gel containing a uniform dispersion of the bupivacaine particles.

Example 14

Bupivacaine-Loaded Hydrogel (Nanosuspension)

Diluent A is prepared by dissolving a surfactant such as PLURONIC F127 (2%-4% w/v) in a carbonate buffer (pH 9.7). Bupivacaine-HCl is suspended in Diluent A and pH is adjusted to pH 10.5-11.0 with 5 M NaOH (Suspension B). Suspension B is micronized with a high shear mixer (such as an IKA high shear mixer) with speeds of up to 15,000 rpm to produce a fine suspension of bupivacaine particles, (typical size ~30-60 microns). The micronized bupivacaine particles are then further processed by high pressure homogenization to form sub-micron sized particles (500-800 nm). The sub-micron sized bupivacaine suspension is loaded into one syringe of a gel spray kit, and when combined with low pH HCl buffer (housed in a second syringe), forms a gel in-situ containing a uniform dispersion of the bupivacaine particles. Alternately, bupivacaine free base can be used as the starting material for generating the sub-micron particles, minimizing the need for any subsequent dilution of the original suspension with 5M NaOH.

Example 15

Preparation of Bupivacaine Nanosuspension (from HCl Salt)

A sub-micron sized suspension ("nanosuspension") of bupivacaine particles was prepared using bupivacaine-HCl as the starting material.

Diluent A was prepared by dissolving PLURONIC F127 (4% w/v) (Spectrum Chemical MFG. Corp.) in a phosphate/carbonate buffer (pH 9.7). Bupivacaine-HCl (Sigma Aldrich) was suspended in Diluent A with magnetic stirring and the pH adjusted with NaOH or HCl to the appropriate value, depending on given polymer system used to form the hydrogel. The suspension was micronized with a high shear homogenizer until the drug particle size was less than 10 μm and then processed by high pressure homogenization at between 15,000-20,000 psi for approximately 45 minutes to form sub-micron sized particles (300-800 nm). The final PLURONIC F127 concentration was between 3.3-4.0% and the drug concentration was 110-150 mg/mL. The nanosuspension (adjusted to pH 10.5-10.8 or pH 9.3-9.5) was transferred in ~6 mL aliquots to depyrogenated 10 mL serum vials, packed in foil pouches and irradiated with at least a 25 kGy dose of from an electron beam source (Iotron Technologies). The final product was stored at 2-8° C.

Example 16

Preparation of Bupivacaine Nanosuspension (from Free Base)

A nanosuspension of bupivacaine particles was prepared using bupivacaine (free base) as the starting material. Nanosuspensions prepared using bupivacaine (free base) may not need subsequent pH adjustment. When the free base was used as the starting material, a more stable polymorph of the drug may be maintained throughout the preparation of the nanosuspension and subsequent preparation of the cross-linked hydrogel.

Diluent B was prepared by dissolving PLURONIC F127 (4% w/v) in a phosphate/carbonate buffer (pH 9.3-9.5). Bupivacaine free base (Sequoia Research Products) was dry-micronized with a high pressure jet mill to form particles of less than 10 μm. The micronized bupivacaine particles are then suspended in Diluent B and further processed by high pressure homogenization to form sub-micron sized particles (300-800 nm). The final PLURONIC F127 concentration was between 3.0-4.0% and the drug concentration was 110-150 mg/mL. The nanosuspension was transferred in ~6 mL aliquots to depyrogenated 10 mL serum vials, packed in foil pouches and irradiated with at least a 25 kGy dose of from an electron beam source (Iotron Technologies). The final product was stored at 2-8° C.

Example 17A

Preparation of Bupivacaine-Loaded Hydrogels

Cross-linked hydrogels are prepared using 4-arm PEG succinimidyl carbonate, 4-arm PEG-sulfhydryl (PEG-SH), and a suspension of sub-micron sized bupivacaine particles.

The 4-arm PEG succinimidyl carbonate and 4-arm PEG-SH components and a pH 2.2 aqueous buffer are prepared separately in serum vials. 4-armPEG succinimidyl carbonate and 4-arm PEG-SH (SunBio) are weighed under inert atmosphere in 1:1 weight ratio into depyrogenated 2 mL serum vials, placed in foil pouches and irradiated on dry ice with at least a 25 kGy dose of from an electron beam source (Iotron Technologies). The pH 2.2 buffer is prepared by adding concentrated HCl to deionized water at a concentration of 6.3 mM. The buffer solution is then filtered through a 0.2 μm nylon filter into depyrogenated 10 mL serum vials, packed in foil pouches and irradiated with at least a 25 kGy dose of from an electron beam source (Iotron Technologies). The final products are stored at 2-8° C.

Immediately before administration, the polymers are dissolved with 0.3 mL of pH 2.2 buffer added via syringe and needle with vortexing. Using a fresh 1 mL syringe and needle, as much of the resulting solution as possible was drawn up (syringe A) and all air is removed. An equal volume of the bupivacaine nanosuspension (prepared from bupivacaine-HCl as described herein), adjusted to pH 10.5-10.8) is drawn up into a separate 1 mL syringe (syringe B) and all air was removed. The syringes are then attached to one another using a luer-loc connector and the contents of each were mixed together until the hydrogel formed and the drug is uniformly distributed. The entire formulation is then pushed into a single syringe (either A or B) and excess gel is expelled so that only 0.3 mL of the formulation was remaining in the syringe. A TEFLON cannula (Micromedics) is attached to the syringe, and the mass of the loaded syringe is recorded. After dispensing the formulation from the syringe, the mass of the empty syringe is recorded, and the final PEG solid concentration in the gel is calculated.

Example 17B

Preparation of Bupivacaine-Loaded Hydrogels

Cross-linked hydrogels were prepared using 4-arm PEG-N-hydroxy-succinimidyl glutarate ester (PEG-NHS), 4-arm PEG-sulfhydryl (PEG-SH), and a suspension of sub-micron sized bupivacaine particles.

The 4-arm PEG-NHS and 4-arm PEG-SH components and a pH 2.2 aqueous buffer were prepared separately in serum vials. 4-arm PEG-NHS (SunBio) and 4-arm PEG-SH (SunBio) were weighed under inert atmosphere in 1:1 weight ratio into depyrogenated 2 mL serum vials, placed in foil pouches and irradiated on dry ice with at least a 25 kGy dose of from an electron beam source (Iotron Technologies). The pH 2.2 buffer was prepared by adding concentrated HCl to deionized water at a concentration of 6.3 mM. The buffer solution was then filtered through a 0.2 μm nylon filter into depyrogenated 10 mL serum vials, packed in foil pouches and irradiated with at least a 25 kGy dose of from an electron beam source (Iotron Technologies). The final products were stored at 2-8° C.

Immediately before administration, the polymers were dissolved with 0.3 mL of pH 2.2 buffer added via syringe and needle with vortexing. Using a fresh 1 mL syringe and needle, as much of the resulting solution as possible was drawn up (syringe A) and all air was removed. An equal volume of the bupivacaine nanosuspension (prepared from bupivacaine-HCl as in Example 3, adjusted to pH 10.5-10.8) was drawn up into a separate 1 mL syringe (syringe B) and all air was removed. The syringes were then attached to one another using a luer-loc connector and the contents of each were mixed together until the hydrogel formed and the drug was uniformly distributed. The entire formulation was then pushed into a single syringe (either A or B) and excess gel was expelled so that only 0.3 mL of the formulation was remaining in the syringe. A TEFLON cannula (Micromedics) was attached to the syringe, and the mass of the loaded syringe was recorded. After dispensing the formulation from the syringe, the mass of the empty syringe was recorded, and the final PEG solid concentration in the gel was calculated. Hydrogels prepared according to the described method are summarized in Table 3. Two bland formulations were prepared having final PEG solids concentrations of 8% (Control A) and 10% (Control B) using the procedure outlined above, with the exception that a high pH 9.7 phosphate/carbonate buffer was used in lieu of the bupivacaine nanosuspension.

TABLE 3

Bupivacaine-Loaded Hydrogel Formulations

| Hydrogel Formulation | Weight of PEG-NHS (mg) | Weight of PEG-SH (mg) | Final PEG Solid Concentration (%) |
|---|---|---|---|
| A | 30 | 30 | 8 |
| B | 38 | 38 | 10 |

Example 17C

Preparation of Bupivacaine-Loaded COSEAL Hydrogels

Cross-linked hydrogels having differing final PEG concentrations were prepared using COSEAL Surgical Sealant (Baxter Healthcare Corporation) and a suspension of submicron sized bupivacaine particles is described. COSEAL hydrogels consist of a covalently cross-linked network of SG-PEG and HS-PEG.

A. Hydrogel C and Hydrogel D

Immediately before administration, a COSEAL kit was opened and the polymer (PEG) components dissolved with the provided low pH buffer. The contents were dispensed into a sterile scintillation vial. 0.2 mL of the PEG solution was drawn into a 1.0 mL syringe. 0.2 mL of the bupivacaine nanosuspension (prepared from bupivacaine-HCl as in Example 3, adjusted to pH 10.5-10.8), was drawn up in a separate syringe. The two syringes were then connected via a fluid dispensing connector and the contents exchanged until full gelation occurred and the drug was uniformly distributed throughout the gel matrix (Hydrogel C). All of the gel was then pushed into one of the syringes. The other syringe was disconnected, and the gel was dispensed to the 0.3 mL graduation. A cannula was attached to the syringe and the mass of the gel and syringe was recorded. The concentration of PEG solids in the gel was 20%. A similar formulation was prepared using the described method but with a bupivacaine nanosuspension adjusted to pH 9.3-9.5 (Hydrogel D).

B. Hydrogel E and Hydrogel F

Immediately before administration, a COSEAL kit was opened and the polymer component dissolved with the provided low pH buffer. The contents were dispensed into a sterile scintillation vial. 0.2 mL of the PEG solution was drawn into a 1.0 mL syringe. In a separate syringe, 0.2 mL the sterile low pH buffer was drawn up. The two syringes were then connected via a fluid dispensing connector and the contents exchanged until well mixed. All of the solution was then pushed into one of the syringes, the other syringe disconnected and then the contents expelled to the 0.2 mL graduation. A bupivacaine nanosuspension (prepared from bupivacaine-HCl as in Example 3, adjusted to pH 10.5-10.8), was drawn up to the 0.2 mL graduation in a separate 1 mL syringe. The two syringes were connected via a fluid dispensing connector and the contents mixed and dispensed as described in the preparation of Hydrogel C (Hydrogel E). The final concentration of PEG solids in the gel was 10%. A similar formulation was prepared using the described method but with a bupivacaine nanosuspension adjusted to pH 9.3-9.5 (Hydrogel F).

C. Hydrogel G

Immediately before administration, a COSEAL kit was opened and the polymer component dissolved with the provided low pH buffer. The contents were dispensed into a sterile scintillation vial. 0.2 mL of the PEG solution was drawn into a 1.0 mL syringe. 0.6 mL the sterile low pH buffer was drawn up in a separate syringe. The two syringes were then connected via a fluid dispensing connector and the contents exchanged until well mixed. All of the solution was then pushed into one of the syringes, the other syringe disconnected and then the contents expelled to the 0.2 mL graduation. In a separate 1 mL syringe, the bupivacaine nanosuspension (prepared from bupivacaine-HCl as in Example 3, adjusted to pH 9.3-9.5), was drawn up to the 0.2 mL graduation. The two syringes were connected via a fluid dispensing connector and the contents mixed and dispensed as described in the preparation of Hydrogel C. The final concentration of PEG solids in the gel was 5% (Hydrogel G). Table 4 shows various formulations prepared using COSEAL and bupivacaine nanosuspensions, using bupivacaine-HCl as the starting material.

TABLE 4

Bupivacaine-HCl Loaded COSEAL Formulations

| Hydrogel Formulation | pH of Nanosuspension | Final PEG Solid Concentration (%) |
|---|---|---|
| C | 10.5-10.8 | 20 |
| D | 9.3-9.5 | 20 |
| E | 10.5-10.8 | 10 |
| F | 9.3-9.5 | 10 |
| G | 9.3-9.5 | 5 |

Example 18A

Levobupivacaine-Loaded TC Gel (In situ Precipitate)

In a first vial, levobupivacaine-HCl (25 mg), 4-arm PEG succinimidyl carbonate (60 mg) and 4-arm PEG-SH (60 mg) were dissolved in 250 µL of pH 2.2 buffer. This solution was combined with an equal volume of carbonate buffer (pH 9.7) through a spray kit. Levobupivacaine precipitated within the gel upon mixing. The levobupivacaine-loaded TC gel swelled 2-2.5 times its original volume.

Example 18B

Levobupivacaine-Loaded Hydrogel (In situ Precipitate)

In a first vial, levobupivacaine-HCl (6, 12.5 or 25 mg), tetrafunctional PEG, pentaerythritol poly(ethylene glycol) ether tetra-N-hydroxy-succinimidyl glutarate (10,000 g/mol) (SG-PEG) (50 mg) and tetrafunctional PEG, pentaerythritol poly(ethylene glycol) ether tetra-sulfhydryl (10,000 g/mol) (PEG-SH) (50 mg) were dissolved in 250 µL of pH 2.2 buffer. This solution was combined with an equal volume of carbonate buffer (pH 9.7) using a spray kit. Levobupivacaine precipitated within the gel upon mixing. All levobupivacaine-loaded gels swelled 1.5-2 times their original volume except for the gel containing the highest amount of levobupivacaine, which swelled about 4 times its initial volume. In vitro release studies showed a steady release of levobupivacaine from the gel. At 9 days, 30% of the drug was released.

Example 19A

Mepivacaine-Loaded TC Gel (In situ Precipitate)

In a first vial, Mepivacaine-HCl (7.2 mg), 4-arm PEG succinimidyl carbonate (60 mg) and 4-arm PEG-SH (60 mg) were dissolved in 250 µL of pH 2.2 buffer. This solution was combined with an equal volume of carbonate buffer (pH 9.7) through a spray kit. Mepivacaine precipitated within the gel upon mixing. The Mepivacaine-loaded TC gel swelled 2-2.5 times its original volume.

Example 19B

Mepivacaine-Loaded Hydrogel (In situ Precipitate)

In a first vial, Mepivacaine-HCl (1.8, 3.7 or 7.4 mg), SG-PEG (50 mg) and PEG-SH (50 mg) were dissolved in 250 µL of pH 2.2 buffer. This solution was combined with an equal volume of carbonate buffer (pH 9.7) through a spray kit. Mepivacaine precipitated within the gel upon mixing All Mepivacaine-loaded gels swelled 1.5-2 times their original volume. In vitro release studies showed a slight burst of mepivacaine from the gel. At 9 days, 60% of the drug was released.

Example 20A

Ropivacaine-Loaded TC Gel (In situ Precipitate)

In a first vial, Ropivacaine-HCl (8.6 mg), 4-armPEG succinimidyl carbonate (60 mg) and 4-armPEG-SH (60 mg) were dissolved in 250 µL of pH 2.2 buffer. This solution was combined with an equal volume of carbonate buffer (pH 9.7) through a spray kit. Ropivacaine precipitates within the gel upon mixing. The Ropivacaine-loaded TC gel swelled 2-2.5 times its original volume.

Example 20B

Ropivacaine-Loaded Hydrogel (In situ Precipitate)

In a first vial, Ropivacaine.HCl (2.3, 4.4 or 8.6 mg), SG-PEG (50 mg) and PEG-SH (50 mg) were dissolved in 250 µL of pH 2.2 buffer. This solution was combined with an equal volume of carbonate buffer (pH 9.7) through a spray kit. Ropivacaine precipitated within the gel upon mixing. All Ropivacaine-loaded gels swelled 2-2.5 times their original volume. In vitro release studies showed a steady release of ropivacaine from the gel. At 9 days, 60% of the drug was released.

Example 21

Determination of the Efficacy of Bupivacaine-Loaded Hydrogel

The efficacy of analgesic-loaded hydrogel formulations can be evaluated using a rat model for postoperative pain (Brennan T J, Vandermeulen E P, and Gebhart G F. *Characterization of a rat model of incisional pain*. Pain 64; 493-501, 1996).

The model uses a plantar incision in the hind paw and is characterized by persistent, reduced withdrawal thresholds to mechanical stimuli, as is the case in patients after surgery. This model has several unique properties compared to other animal models of pain: it is caused by an incision; it is persistent; there is reduced withdrawal threshold suggesting mechanical hyperalgesia; and the time course of the pain behaviors displays characteristics similar to those noted in postoperative patients. This model is useful for screening test compounds that may be effective in reducing postoperative pain and for understanding pain mechanisms associated with incisions. In contrast to other pain models, no consistent flinching and licking behavior is observed after the immediate recovery period after surgery. Many laboratories have studied this model extensively, and the behavioral responses have been used widely in many pharmacological studies (Field M J, Holloman E F, McCleary S, Hughes J and Singh L. Evaluation of Gabapentin and S-(+)-3-*Isobutylgaba in a rat model of postoperative pain*. J Pharmacol Exp Therap 282: 1242-1246, 1997; Brennan T J, Zahn P K, Pogatzki-Zahn, E M. *Mechanisms of incisional pain*. Anesthesiology Clin N Am 23; 1-20, 2005; and Pogatzki E M, Vandermeulen E P, and Brennan T J. *Effect of plantar local anesthetic injection on dorsal horn neuron activity and pain behaviors caused by incision*. Pain 97; 151-161, 2002).

Determination of Test Article Efficacy:

Wistar rats, 350 to 500 g are used in this study. After anesthesia is induced the plantar aspect of one hind paw is cleaned and draped. A 1 cm longitudinal incision is made through the skin and fascia of the paw, beginning 0.5 cm from the proximal edge of the heel and extending towards the digits. The underlying plantar flexor muscle is elevated and incised longitudinally with the scalpel blade. After hemostasis is achieved the skin is apposed and sutured.

For this study there are four treatment groups: saline, bupivacaine alone, hydrogel alone, and bupivacaine-loaded hydrogel. Both test and control articles are infused into the surgical site just prior to closing. Determination of the withdrawal threshold to punctuate mechanical stimuli is made by the use of an electronic von Frey filament device which is applied to the surface of the injured hind paw just medial to the incision. The device measures the pressure required before the animal withdraws its paw. A force of 400 to 500 mN is usually required before a rat withdraws an uninjured paw, but this threshold is lowered to 10-50 mN after surgery and takes 6-7 days to regain postoperative values.

Thermal sensitivity is also increased postoperatively. This is measured by placing the rat on a hot plate that increases temperature slowly, at a steady rate. The rat lifts its injured paw when it becomes uncomfortable, and the temperature at which this occurs is noted. As with mechanical stimuli, the temperature at which the rat lifts its paw is lowest after surgery, and this thermal hyperalgesia persists for several day.

Model Description:

The plantar incision model was used to evaluate the analgesic efficacy of a bupivacaine-loaded hydrogel formulation. The PEG hydrogel formulation used in this study (referred to as a hydrogel formulation) consists of cross-linked 4-arm PEG N-hydroxy-succinimidyl glutarate ester (PEG-NHS) and 4-arm PEG-Thiol (PEG-SH). Rats underwent the surgical procedure and were administered either saline, MARCAINE (a bupivacaine saline solution), a bland hydrogel formulation, or a bupivacaine-loaded hydrogel formulation. Pain levels were evaluated for 7 days using established monitoring methods. In addition, at termination blood was obtained by cardiac puncture and treated paws were removed for later analytical measurements of bupivacaine tissue levels.

Materials

Control Articles

The control articles were 0.5 mL/rat of saline, 0.5 mL/rat of a commercially available formulation of 0.5% bupivacaine, obtained from Hospira (MARCAINE, 5 mg/mL, Lot #50285DD). and 0.2 mL/rat of a bland hydrogel formulation (Control A).

Test Article

The test article was 0.2 mL/rat of Hydrogel A (targeted dose between 8 and 10 mg per animal).

Test System

Male Wistar rats (Harlan, Indianapolis, Ind.) weighing approximately 366-475 g were used in this study. Animals were cared for using institutional procedures at the Angiotech Vivarium (Vancouver, BC).

Methods

Animal Preparation

Animals were weighed, anesthetized with isofluorane (5% induction and 1.5% maintenance). As perioperative antibiotic prophylaxis, each rat also received an intramuscular injection of duplocillin (7500 U/kg) in the flank. In addition the paw volume was measured prior to surgery using a plethysmograph (Model # 7140, UGO BASILE Biological Research Apparatus), to obtain a baseline reading.

Surgical Procedure

The rat was draped in a sterile fashion, with one hind paw exposed. The hind paw was cleaned with chlorhexidine and surgical grade iodine. A 1-cm longitudinal incision was made through the skin and fascia of the paw with a number 11 scalpel blade, beginning 0.5 cm from the proximal edge of the heel and extending toward the digits. The underlying plantar flexor muscle was elevated with small curved forceps and incised longitudinally with the scalpel blade, keeping the muscle origin and insertion intact. A small subcutaneous pocket was made between skin and muscle in the area between the distal end of the incision and the toes, to allow for the presence of the test articles.

Test and Control Article Administration

For the administration of the hydrogel and bupivacaine-loaded hydrogel formulations, the catheter of the delivery syringe was placed into the subcutaneous pocket, and approximately 0.2 mL of the test article was introduced. After hemostasis with gentle pressure, the skin was apposed with two mattress sutures of 5-0 PROLENE. In the bupivacaine group, after the incision was sutured, 0.1 mL of the 0.5% bupivacaine solution was injected at the medial and lateral aspect of the ankle, posterior to the malleoli to anesthetize the sural and tibial nerves. This was followed by subcutaneous infiltration of 0.3 mL in the tissues surrounding the incision site. The same injection procedure was followed for the saline injection group. A liquid bandage (OP-SITE) was then applied to the plantar surface of the paw in all groups. The subjects were then placed in a clean cage, under a heat lamp, and covered with towels to maintain body temperature during recovery. After surgery the rats were housed in cages with soft bedding and longer sip tubes and the incisions examined daily.

Experimental Design

A total of 21 control and 7 test article rats were used in this study.

| Group | No. of Rats | Test Article | Volume (mL)/rat |
|---|---|---|---|
| 1 | 7 | Saline | 0.5 |
| 2 | 7 | MARCAINE (0.5%) | 0.5 |
| 3 | 7 | Control Article (Control A) | 0.2 |
| 4 | 7 | Test Article (Hydrogel A) | 0.2 |

Data Collection Methods

In Life Observations

Animals were observed every day after surgery for the morbid signs of illness including difficulty in breathing and behavioral observations, such as abnormal gait or shaking; signs of weakness, such as ruffled fur, hunched posture while sitting or walking, or lethargy, or failure to respond to stimuli. A daily clinical score was assigned.

Assessment of Pain Levels

The analgesic efficacy of the test and control articles was determined by examination of mechanical hyperalgesia and measurement of pain-related weight distribution. Assessments were made one day before surgery (baseline testing), at 1, 2, and 4 hours post-surgery and then daily for 7 days. The degree of mechanical hyperalgesia was measured by the use of a dynamic plantar aesthesiometer. The rat was placed in a Plexiglas enclosure over an elevated plastic mesh floor with a grid size of 12×12 mm. After cessation of exploratory behavior, the touch-stimulator was positioned below the target area of the animal paw, which is just medial to the incision at the proximal part of the paw. The start key was pressed to lift a straight metal filament from the touch-stimulator which reached the plantar surface and began to exert an upward force. This force increased at a rate of 10 g per second, until the animal responded by withdrawing its paw, or until the cutoff force of 50 g was reached. Paw withdrawal reflex was automatically recorded using two metrics: the latency until withdrawal, in seconds, and the force at which the paw was withdrawn, in grams. Measurement of pain-related weight distribution was determined by placing the rat on an incapacitance meter, which is a dual channel scale that separately measures the weight the animal distributes to each hind paw. While normal rats distribute weight 50-50, the ratio of weight distribution between an injured and non-injured paw is a natural measure of the level of discomfort in the injured paw.

Paw Volume

Three days after surgery the rats were anesthetized with isofluorane and the injured paw volume was measured using a plethysmograph. At this time the stitches were removed.

Sacrifice and Tissue Harvesting

The rats were euthanized by $CO_2$ inhalation seven days after surgery. Blood was obtained by cardiac puncture from each rat and centrifuged. The plasma was extracted and frozen for later analysis. The treated paw from each rat was severed just proximal to the malleoli. For each group of seven rats, four of the treated paws were immediately placed on ice for later analysis of bupivacaine levels and the remaining three treated paws were placed in 10% buffered formalin for histology.

Histology

Fixed specimens were sent to Wax-It (Vancouver, Canada) for histological processing. The paws were decalcified, embedded in paraffin and stained with hematoxylin and eosin. After fixation and processing the slides were evaluated for tissue reactivity by light microscope using a quantitative histological rating system as follows:

A total biocompatibility score was then obtained that represented a summary of the tissue response to the presence of the test or control articles. In addition, the presence of any foreign material remaining in the implant site was noted. Representative micrographs were taken using Quick Capture Imaging Software.

Analytical Determinations

Bupivacaine levels in plasma and in rat paw were determined by liquid-liquid extraction followed by analysis by LC-MS/MS. The samples were treated as follows:

Rat Paws:

Whole rat paws were homogenized in a cryo-mill and then spiked with the internal standard, Ropivacaine. To this, 1 mL of deionized water and 0.2 mL of 0.2N NaOH was added to basify the mixture. Seven mL of hexane was used to extract the bupivacaine, which was then collected, and dried. The residue was reconstituted in 1.0 mL of 0.1% formic acid.

Plasma:

Plasma was spiked with the internal standard, Ropivacaine, and then combined with 0.2N NaOH to basify the mixture. Hexane was used to extract the bupivacaine, which was then collected and dried. The residue was reconstituted in 0.1% formic acid.

Chromatographic Conditions:

| Parameter | |
| --- | --- |
| Column | C18 ACE3 2.1 × 75 mm |
| Mobile Phase | 50 mM $NH_4OAc$/0.2% FA in MeOH (55/45) |
| Flow Rate | 0.3 mL/min |
| Injection Volume | 10 μL |
| Detection (MS/MS) | Ropivacaine 275 > 126 |
| | Bupivacaine 289 > 140 |

Results and Discussion

In Life Daily Observations

The in life daily observations for every rat were measured. The animals' behavior and gait did not appear to be affected by the surgical procedure or by administration of the test or control articles.

Assessment of Pain Levels

Mechanical Hyperalgesia

Figure 3:
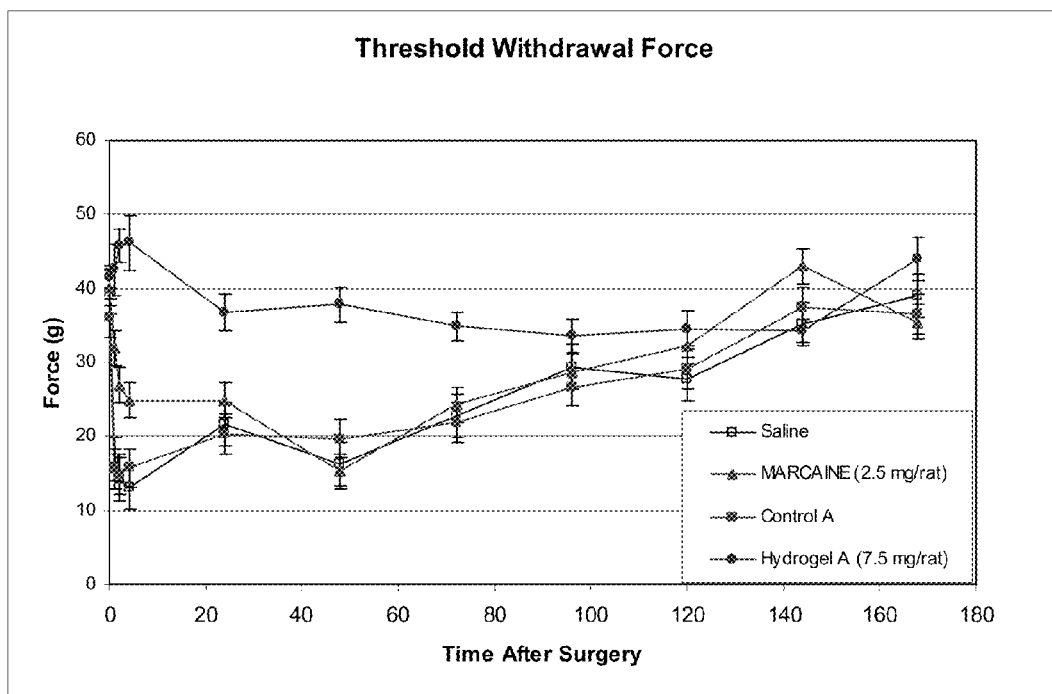
FIG. 3 is a graph showing the average threshold withdrawal force for each group of rats used in the study of Example 21. Each data point represents the mean±SE of the lowest value of three readings obtained per rat (n=7) at each time point.

Three tests using the plantar aesthesiometer to measure mechanical hyperalgesia were obtained at each time point for each rat. The lowest force from the 3 tests producing a response on the injured paw for each animal was considered the withdrawal threshold force. The mean±SEM of this value for each group is graphed in FIG. 3. A decrease in the average threshold withdrawal force of the injured paw was observed in the saline, MARCAINE and hydrogel formulation groups after surgery. However, in the MARCAINE group, the decrease was less than that observed in the saline or hydrogel formulation treated group for the first 4 hours. After 24 hours the withdrawal threshold of the MARCAINE, hydrogel formulation and saline treated groups were similar and increased gradually with time, reaching presurgery values between four and five days. In contrast, the average threshold withdrawal force in the bupivacaine-loaded hydrogel formulation did not decrease after surgery, remaining at or near presurgery levels for the length of the study. After four days, the average threshold withdrawal force for all four groups was nearly identical, due to healing of the injured paws.

Weight Bearing Ratio

The weight bearing ratio can be measured by placing a rat onto the incapacitance scale. A total of three readings are taken and recorded, and the ratio of the injured/uninjured hind limb weight bearing is calculated.

Paw Volume

Figure 4:
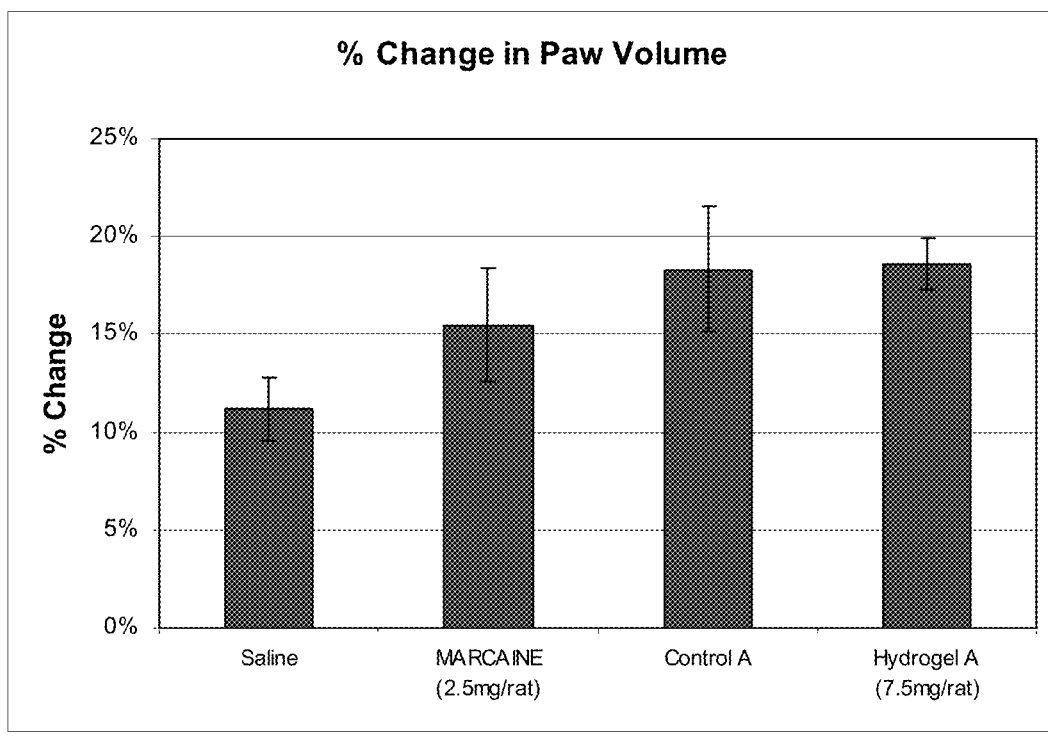
FIG. 4 is a graph showing the percent change in paw volume of rats used in the study of Example 21, from baseline to three days. Each column is the mean±SE of 7 rats.

The percent change in paw volume from baseline to three days is shown in FIG. 4. As expected, all groups showed some increase in paw volume which can be attributed to the surgical procedure itself. A slight increase over control values was observed in the MARCAINE group, but this was not significant (student's t-test, $p<0.05$). A significant difference however, was observed between the saline and the hydrogel and bupivacaine-loaded hydrogel formulation groups. The percent change in paw volume of the hydrogel and the bupivacaine-loaded hydrogel formulation groups however, was nearly identical (18.31%±0.02 versus 18.56%±0.01, respectively), suggesting that the presence of bupivacaine in the gel did not contribute to the increase observed.

Body Weights

Figure 5:
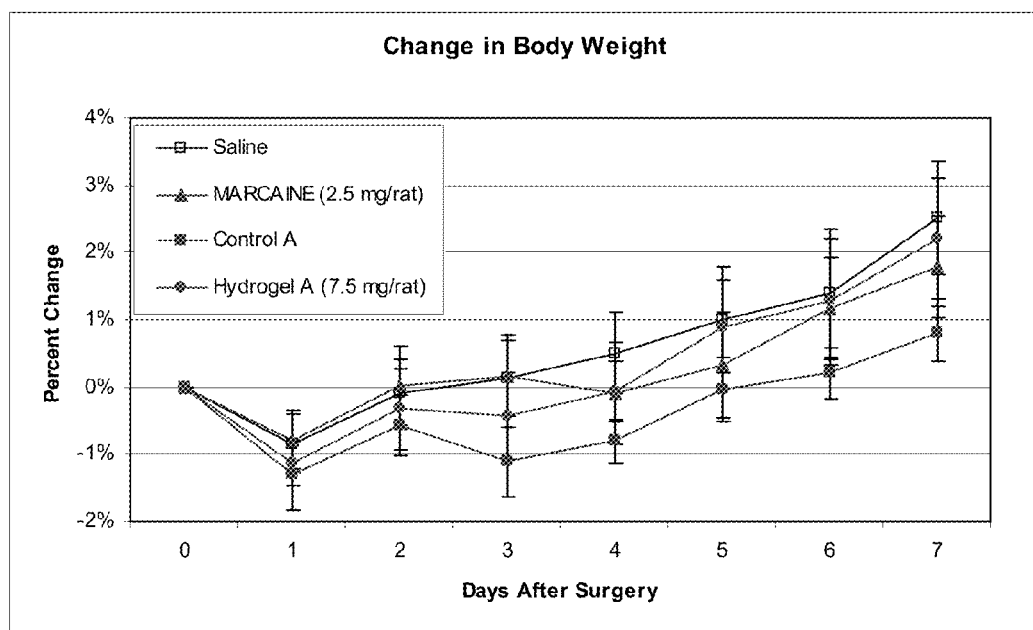
FIG. 5 is a graph showing the average percent change in body weight of rats used in the study of Example 21. Each data point is the mean±SE of 7 rats.

The average percent change in rat body weight is graphed in FIG. 5. All groups had an initial decrease in body weight of less than 2%. However, by Day 5 all groups had regained or exceeded their pre-surgery body weight.

Histology

The results of the histopathological evaluation of the treated paws are shown in Table 5. Each criterion is scored as follows:

0=Entity not present
0.5=Entity present to a slight degree (occasionally)
1=Entity present to a mild degree
2=Entity present to a moderate degree
3=Entity present to a marked degree All tissues examined were very similar histologically, with only minimal fibrosis, inflammation, cellular infiltration, and fibroendothelial proliferation observed. No residual foreign material was present in any of the specimens.

TABLE 5

Individual histology values and total biocompatibility scores

| Lot Number | Necrosis | Granuloma tissue | Fibrosis | Hemorrhage | Inflammation | Cellular Infiltrate | Fibro endothelial Proliferation | Fatty Infiltration | Total Biocompatiblity Score | Presence of Material |
| --- | --- | --- | --- | --- | --- | --- | --- | --- | --- | --- |
| Saline | 0 | 0 | 1 | 0 | 1 | 1 | 1 | 0 | 0.500 | 0 |
| | 0 | 0 | 1 | 0 | 1 | 1 | 1 | 0 | 0.500 | 0 |
| | 0 | 0 | 1 | 0 | 1 | 1 | 1 | 0 | 0.500 | 0 |
| MARCAINE | 0 | 0 | 1 | 0 | 1 | 1 | 1 | 0 | 0.500 | 0 |
| | 0 | 0 | 2 | 0 | 1 | 1 | 1 | 0 | 0.625 | 0 |
| | 0 | 0 | 1 | 0 | 1 | 1 | 1 | 0 | 0.500 | 0 |
| Control A | 0 | 0 | 1 | 0 | 1 | 1 | 1 | 0 | 0.500 | 0 |
| | 0 | 0 | 1 | 0 | 1 | 1 | 1 | 0 | 0.500 | 0 |
| | 0 | 0 | 1 | 0 | 1 | 1 | 1 | 0 | 0.500 | 0 |

TABLE 5-continued

Individual histology values and total biocompatibility scores

| Lot Number | Necrosis | Granuloma tissue | Fibrosis | Hemorrhage | Inflammation | Cellular Infiltrate | Fibro endothelial Proliferation | Fatty Infiltration | Total Biocompatiblity Score | Presence of Material |
|---|---|---|---|---|---|---|---|---|---|---|
| Hydrogel A | 0 | 0 | 1 | 0 | 1 | 1 | 1 | 0 | 0.500 | 0 |
|  | 0 | 0 | 1 | 0 | 1 | 2 | 2 | 0 | 0.750 | 0 |
|  | 0 | 0 | 1 | 0 | 1 | 1 | 1 | 0 | 0.500 | 0 |

Analytical Determinations

The total bupivacaine levels in the paws of rats in the MARCAINE and bupivacaine-loaded hydrogel formulation are shown in Table 6. The result obtained in both groups was highly variable, with a range of 1.9-28.5 ng/paw in the MARCAINE group (mean of 11.5±5.9) and a range of 0.5-184.4 ng/paw (mean of 55.9±43.1) in the bupivacaine-loaded hydrogel formulation group.

TABLE 6

Bupivacaine levels in rat paws

| Description | Bupivacaine (ng/mL) | Bupivacaine (ng/paw) | Mean (ng/paw) | SD |
|---|---|---|---|---|
| MARCAINE | 24.2 | 28.5 | 11.5 | 11.7 |
|  | 5.2 | 6.2 |  |  |
|  | 1.6 | 1.9 |  |  |
|  | 7.5 | 9.6 |  |  |
| Hydrogel A | 12.8 | 16.4 | 55.9 | 86.2 |
|  | 2.1 | 0.5 |  |  |
|  | 141.8 | 184.4 |  |  |
|  | 18.1 | 22.1 |  |  |

Conclusions

The mechanical hyperalgesia data show that the bupivacaine-loaded hydrogel formulation provides effective analgesia for at least four days after surgery in the rat plantar incision model. The presence of the hydrogel formulation in the paw resulted in a moderate increase in paw volume which was not aggravated by the presence of bupivacaine. No adverse effects were noted due to the presence of the bupivacaine-loaded hydrogel formulation in the paw, as determined by body weight and histological evaluation. Although variable, analytical determination of bupivacaine levels in rat paw indicates that more drug remains in the bupivacaine-loaded hydrogel formulation group than in the MARCAINE group.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition comprising a biocompatible hydrogel and an analgesic, wherein the analgesic is uniformly distributed in the hydrogel as in situ generated particles, and wherein the biocompatible hydrogel is produced by a method comprising:

mixing a first compound and a second compound to obtain a first mixture, adding an acidic aqueous solution and the analgesic to the first mixture to obtain a first solution, adding a basic aqueous solution to the first solution, wherein, the first compound is a compound of Formula I:

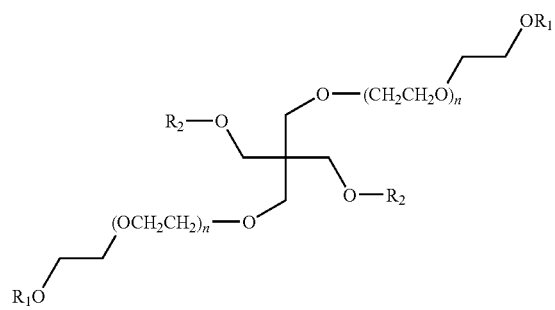

wherein each $R_1$ is independently selected from the group consisting of hydrogen, alkyl, —C(=O)$R_3$, and —C(=O)O$R_3$;

each $R_2$ is independently selected from the group consisting hydrogen, alkyl, and —(CH$_2$CH$_2$O)$_n$—$R_4$, $R_3$ is selected from the group consisting of hydrogen, halogen, amino, monoalkylamino, dialkylamino, alkyl, carbocyclyl, and heterocyclyl;

each $R_4$ is independently selected from the group consisting hydrogen, alkyl, —CH$_2$CH$_2$OH, and —CH$_2$CH$_2$O$R_1$;

each n is independently an integer greater than 1;

wherein at least one of $R_1$ is not hydrogen or alkyl; and the second compound is a compound of Formula III:

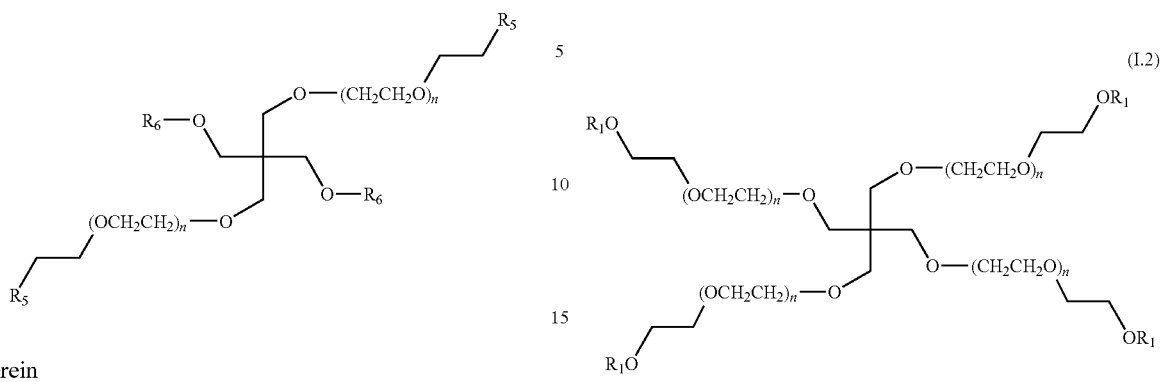

(III)

wherein each R₅ is independently selected from the group consisting of hydrogen, alkyl, —OR₇, —SR₇, and —N(R₇)₂;

each R₆ is independently selected from the group consisting hydrogen, alkyl, and —(CH₂CH₂O)ₙ—R₈;

each R₇ is independently selected from the group consisting of hydrogen, alkyl, carbocyclyl, and heterocyclyl;

each R₈ is independently selected from the group consisting hydrogen, alkyl, and —CH₂CH₂R₅;

each n is independently an integer greater than 1;

wherein at least one of —R₅ is not hydrogen or alkyl, and wherein the analgesic is a local anesthetic selected from the group consisting of bupivacaine, levobupivacaine, ropivacaine, lidocaine, mepivacaine, prilocaine, cinchocaine, etidocaine, articaine and salts thereof.

2. The composition of claim 1, wherein the compound of Formula I is a compound of Formula I.2:

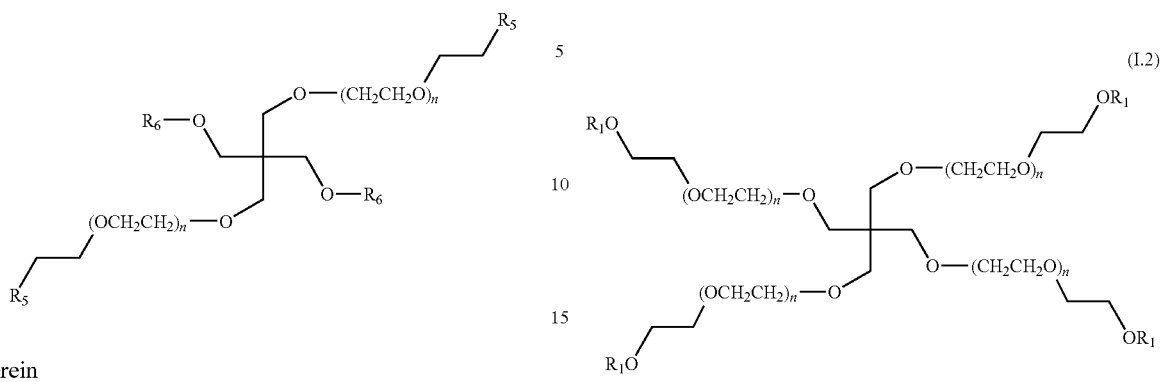

(I.2)

wherein at least one of —OR₁ is

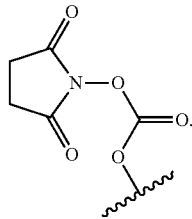 [SMILES: *OC(=O)ON1C(=O)CCC1=O]

3. The composition of claim 1, wherein the compound of Formula I is a compound of Formula II.3:

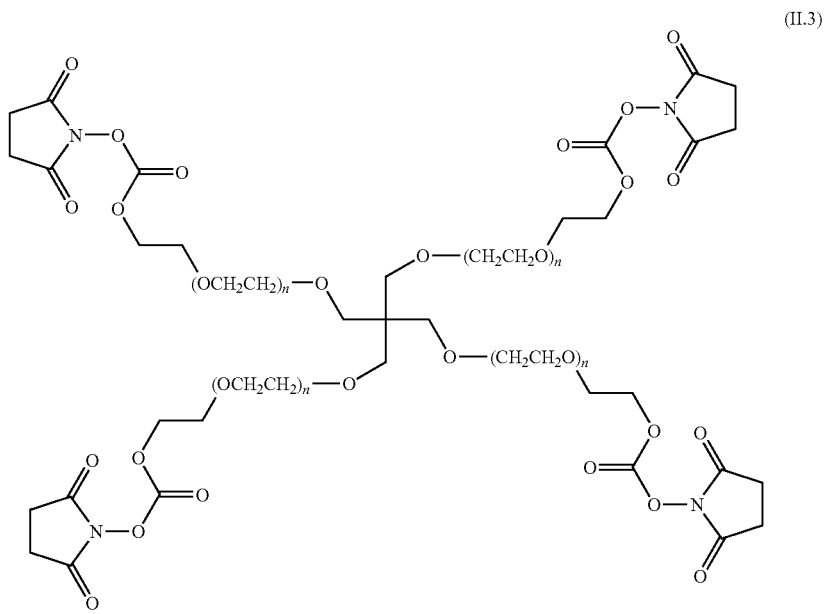

(II.3)

wherein each n is independently an integer greater than 1.

4. The composition of claim 1, wherein the compound of Formula III is a compound of Formula IV.1, Formula IV.2 Formula IV.3, Formula IV.4 or Formula IV.5:
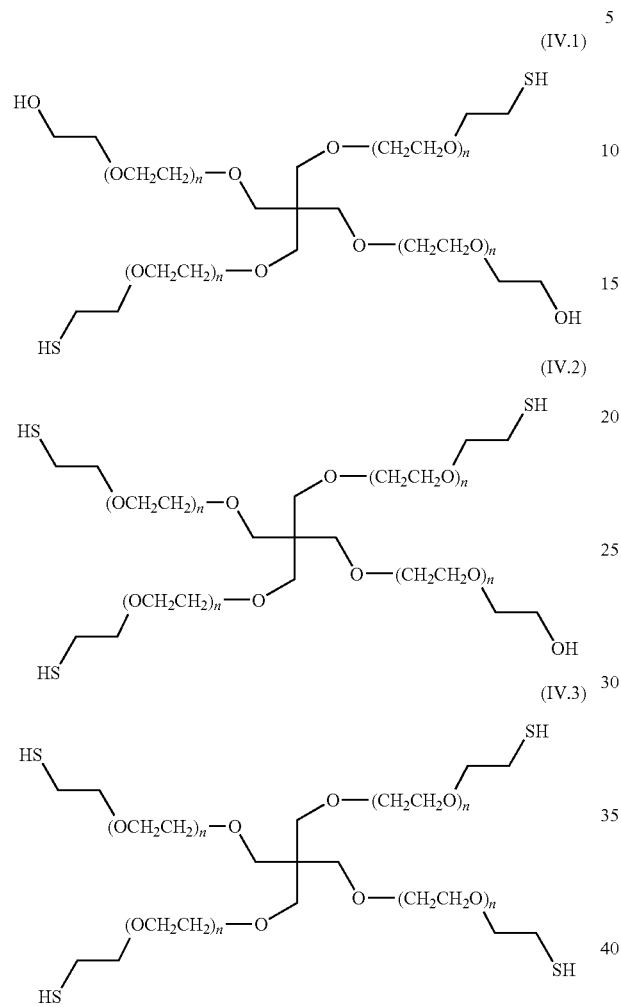
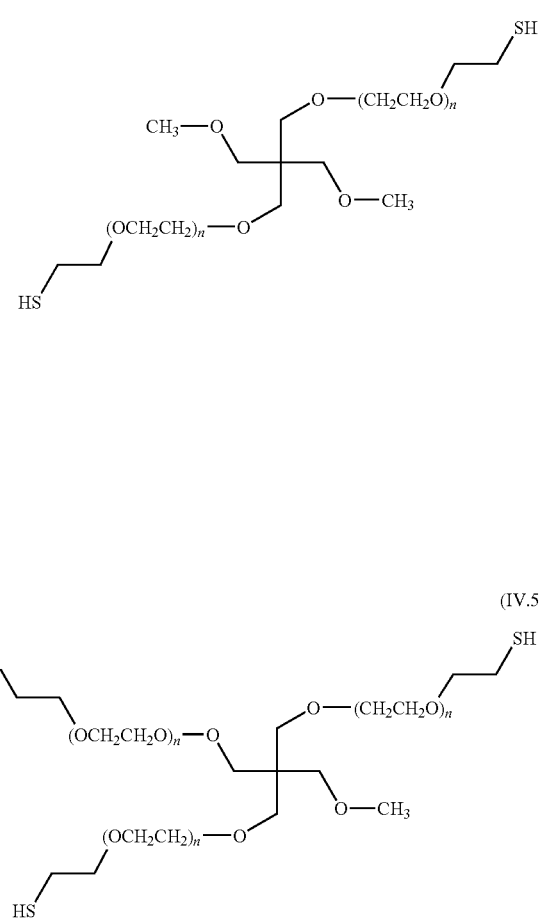
wherein each n is independently an integer greater than 1.
5. The composition of claim 1, wherein the particles of the analgesic are 1-50 microns in sizes.
* * * * *